US010975433B2

(12) United States Patent
Ito et al.

(10) Patent No.: US 10,975,433 B2
(45) Date of Patent: Apr. 13, 2021

(54) SHORT-CHAIN NUCLEIC ACID ELONGATION PRIMER SET, ASSAY KIT, AND SHORT-CHAIN NUCLEIC ACID ELONGATION, AMPLIFICATION AND DETECTION METHODS

(71) Applicant: KABUSHIKI KAISHA TOSHIBA, Minato-ku (JP)

(72) Inventors: Keiko Ito, Kawasaki (JP); Mika Inada, Tokyo (JP); Koji Hashimoto, Atsugi (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 47 days.

(21) Appl. No.: 16/017,367

(22) Filed: Jun. 25, 2018

(65) Prior Publication Data
US 2019/0127793 A1 May 2, 2019

(30) Foreign Application Priority Data

Jul. 11, 2017 (JP) .............................. JP2017-135726
Apr. 24, 2018 (JP) .............................. JP2018-083156

(51) Int. Cl.
*C12Q 1/6876* (2018.01)
*C12Q 1/6848* (2018.01)
(Continued)

(52) U.S. Cl.
CPC ........... *C12Q 1/6876* (2013.01); *C12N 15/10* (2013.01); *C12P 19/34* (2013.01); *C12Q 1/6848* (2013.01); *C12Q 2600/178* (2013.01)

(58) Field of Classification Search
CPC .................... C12Q 2525/207; C12Q 2531/119
See application file for complete search history.

(56) References Cited

U.S. PATENT DOCUMENTS 8,067,162 B2    11/2011   Hayashizaki et al.
9,586,987 B2     3/2017   Hayashizaki et al.
(Continued)

FOREIGN PATENT DOCUMENTS

JP         4370385      11/2009
JP       2013-143966     7/2013
(Continued)

OTHER PUBLICATIONS

Wan, G. et al., High-performance quantification of mature microRNAs by real-time RT-PCR using deoxyuridine-incorporated oligonucleotides and hemi-nested primersRNA, vol. 16, pp. 1436-1445 (Year: 2010).*

(Continued)

*Primary Examiner* — Teresa E Strzelecka
(74) *Attorney, Agent, or Firm* — Oblon, McClelland, Maier & Neustadt, L.L.P.

(57) ABSTRACT

According to one embodiment, a primer set for elongating a target short-chain nucleic acid containing a first sequence to obtain an elongated product is provided. The elongated product contains a second, a third, a fourth sequence, a complementary sequence of the 1'-th sequence and a sixth sequence. The complementary sequence of the 1'-th sequence is a loop primer sequence. The primer set contains a first elongation primer containing a first elongation primer sequence and a complementary sequence of the sixth sequence, and a second elongation primer containing a second elongation primer sequence, the fourth, the third, and the second sequence.

18 Claims, 29 Drawing Sheets

Specification includes a Sequence Listing.

(51) Int. Cl.
*C12P 19/34* (2006.01)
*C12N 15/10* (2006.01)

(56) References Cited

U.S. PATENT DOCUMENTS

| | | |
|---|---|---|
| 2010/0092971 A1 | 4/2010 | Okamoto et al. |
| 2014/0017692 A1 | 1/2014 | Komiya |
| 2018/0127814 A1 | 5/2018 | Hashimoto et al. |
| 2018/0274022 A1 | 9/2018 | Inada et al. |
| 2018/0363043 A1 | 12/2018 | Hashimoto et al. |

FOREIGN PATENT DOCUMENTS

| | | |
|---|---|---|
| JP | 2018-068258 | 5/2018 |
| JP | 2018-153157 | 10/2018 |
| JP | 2019-53 | 1/2019 |
| WO | WO 2012/077819 A1 | 6/2012 |

OTHER PUBLICATIONS

Li, C. et al., One-step ultrasensitive detection of microRNAs with loop-mediated isothermal amplification (LAMP), Chem. Comm., vol. 47, pp. 2595-2597 (Year: 2011).*

Wenfang Du, et al., "A litigation-based loop-mediated isothermal amplification (litigation-LAMP) strategy for highly selective microRNA detection," Chemical Communications, vol. 52, No. 86, 2016, 19 Pages.

Tsugunori Notomi, et al., "Loop-mediated isothermal amplification of DNA" Nucleic Acids Research, vol. 28, No. 12, 2000, pp. 7 pages.

Jiangyan Zhang, et al., "Ultrasensitive quantification of mature microRNAs by real-time PCR based on litigation of a ribonucleotide-modified DNA probe," Chemical Communications, vol. 47, No. 33, 2011 pp. 9465-9467.

\* cited by examiner

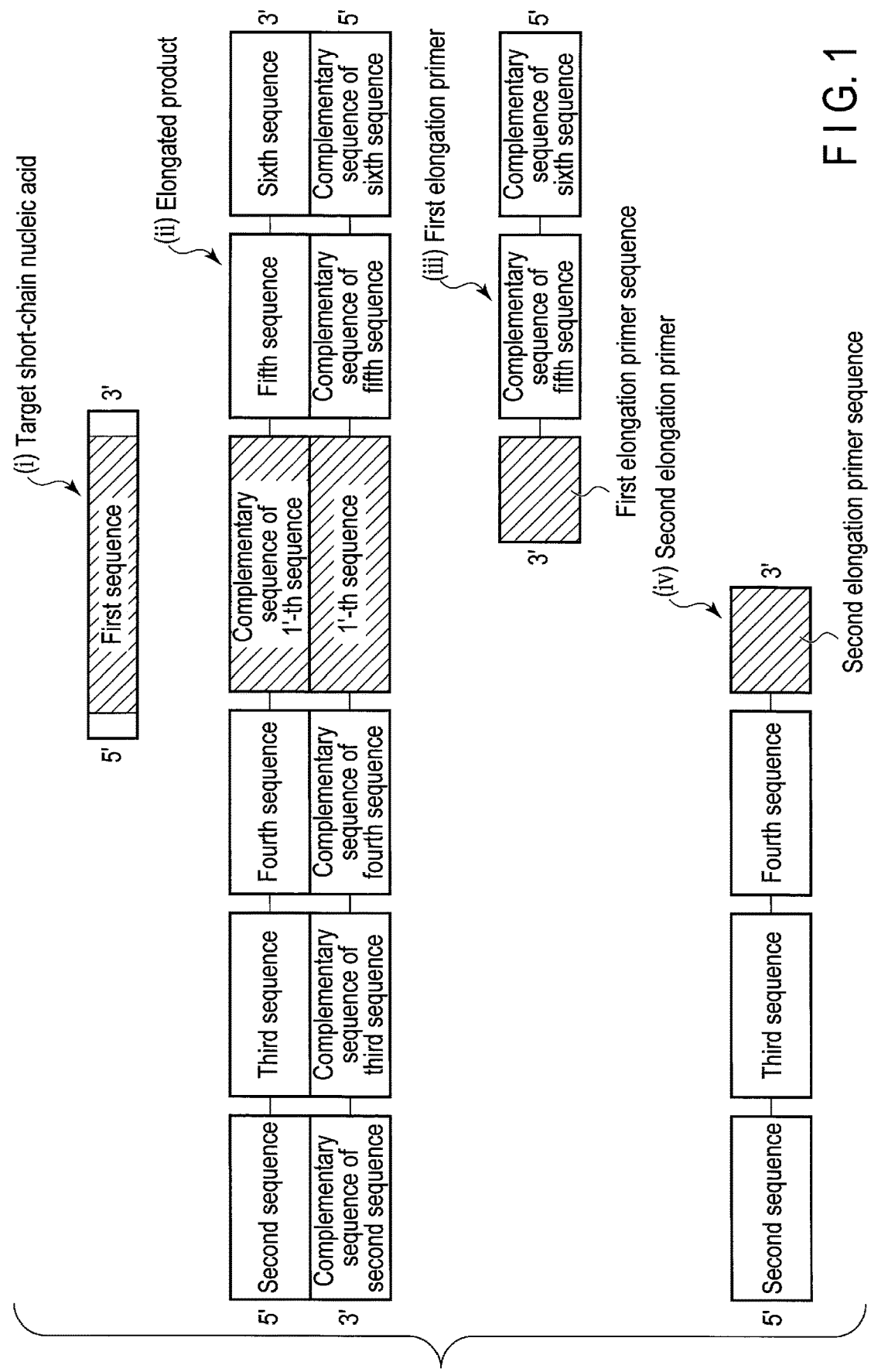
F I G. 1

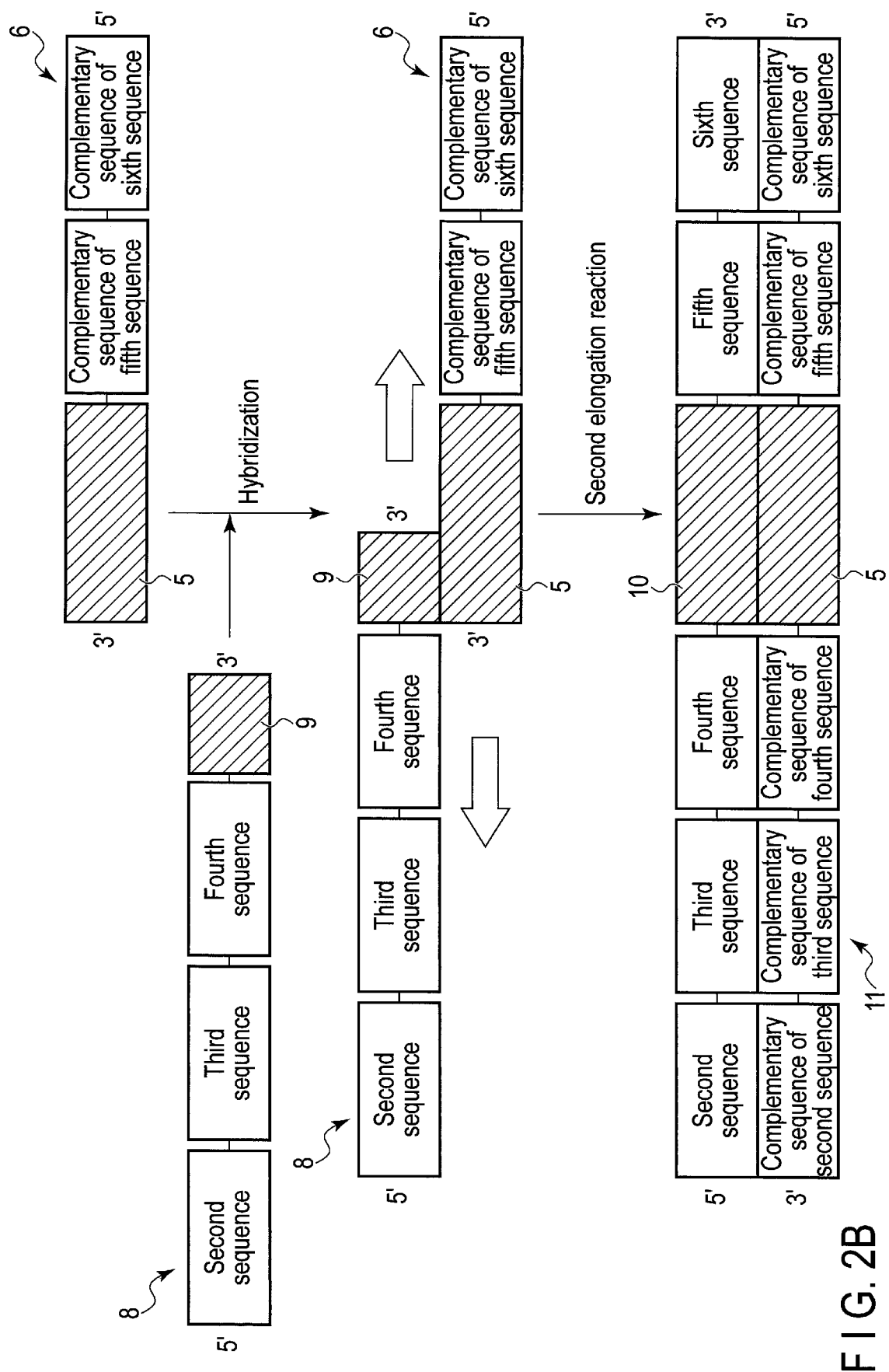
F I G. 2B

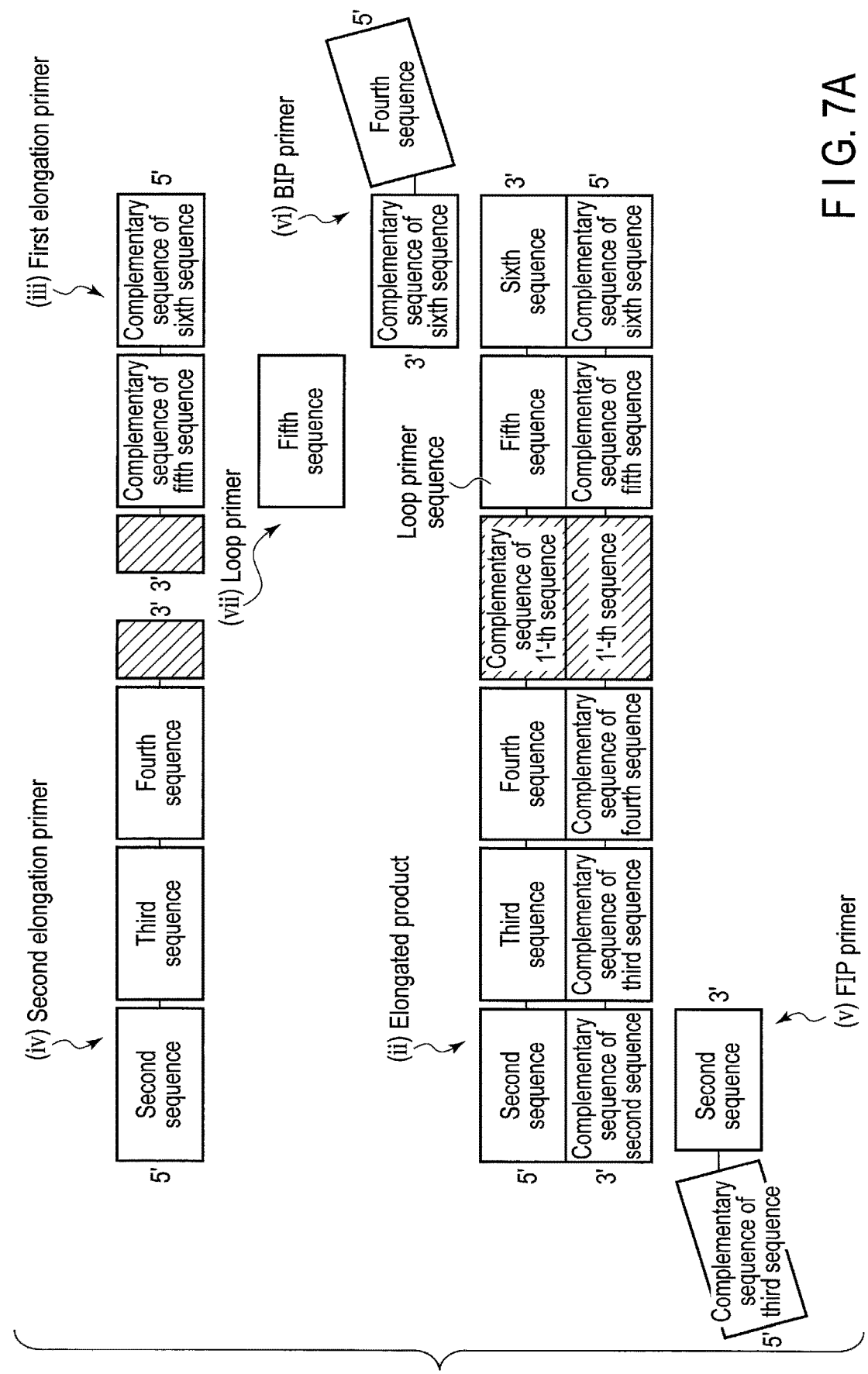
F I G. 7A

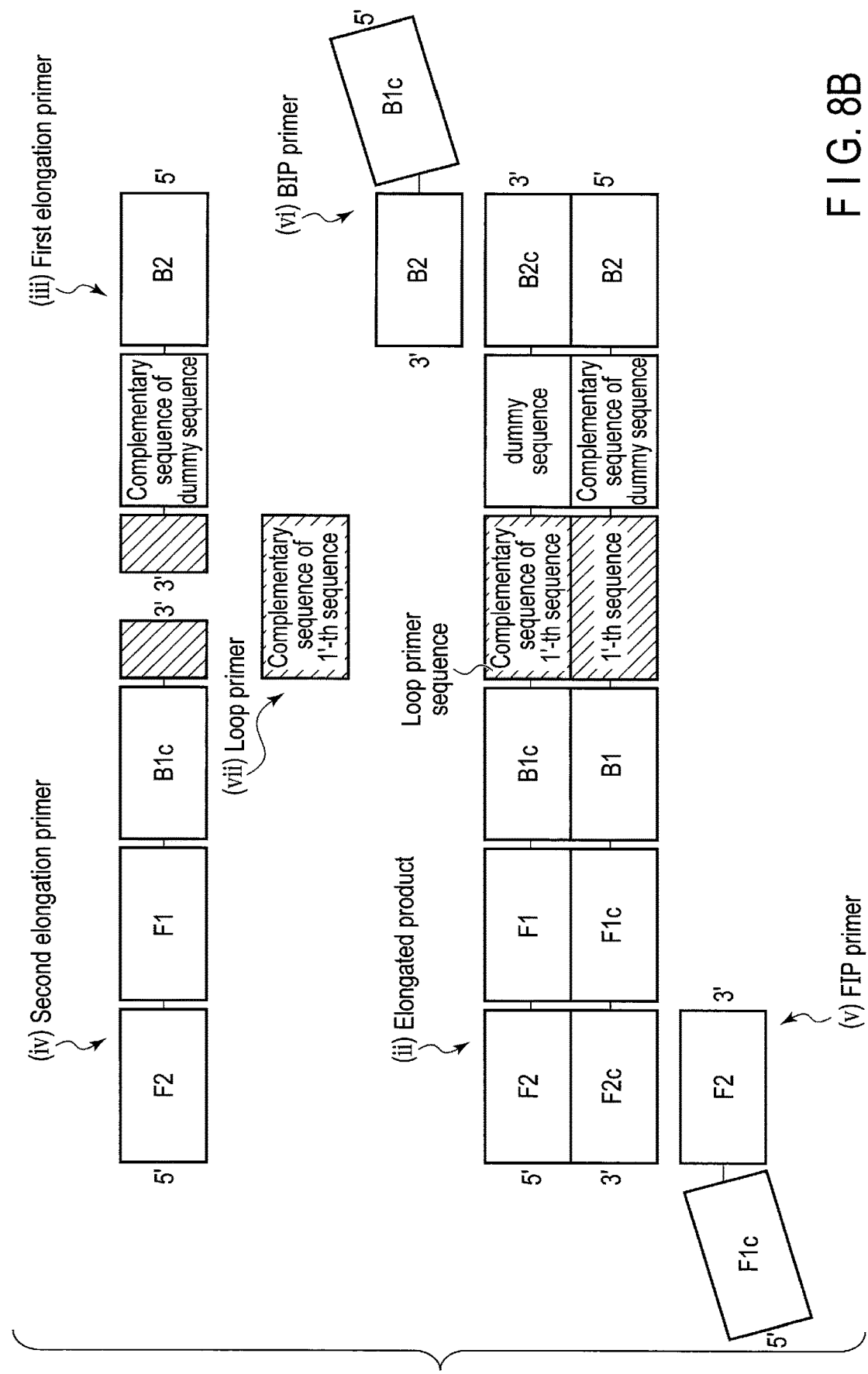
F I G. 8B

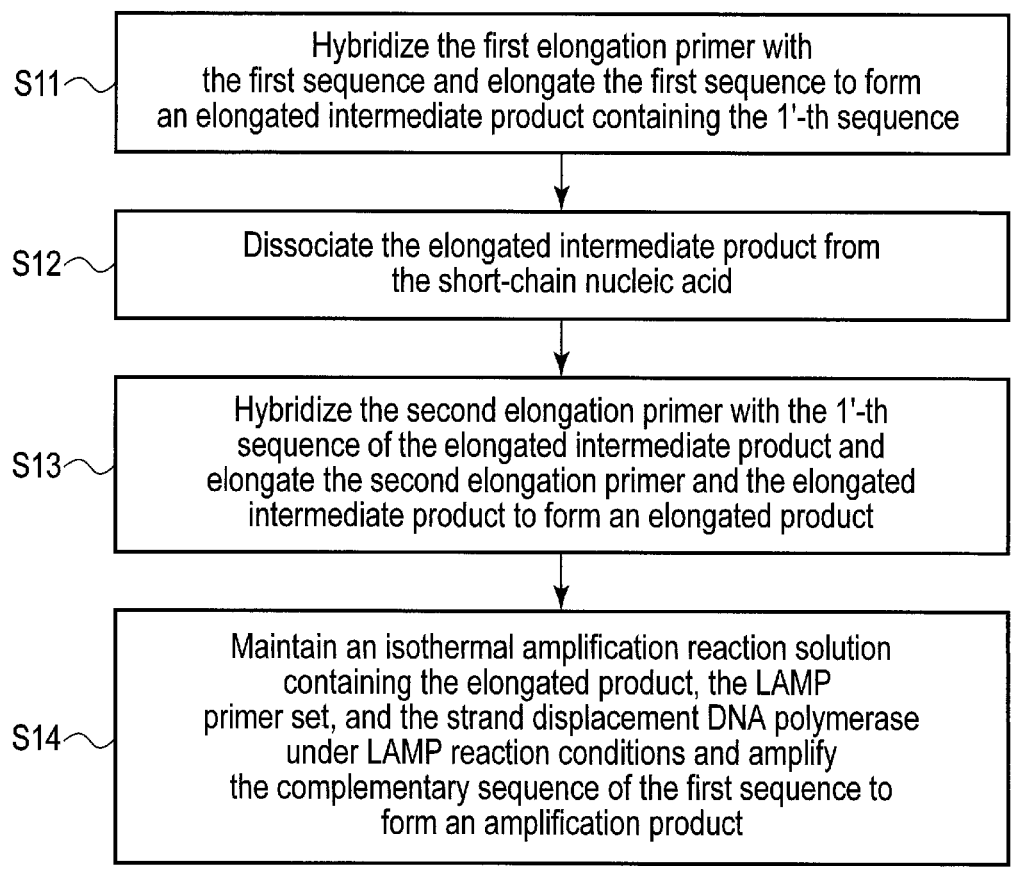
F I G. 10

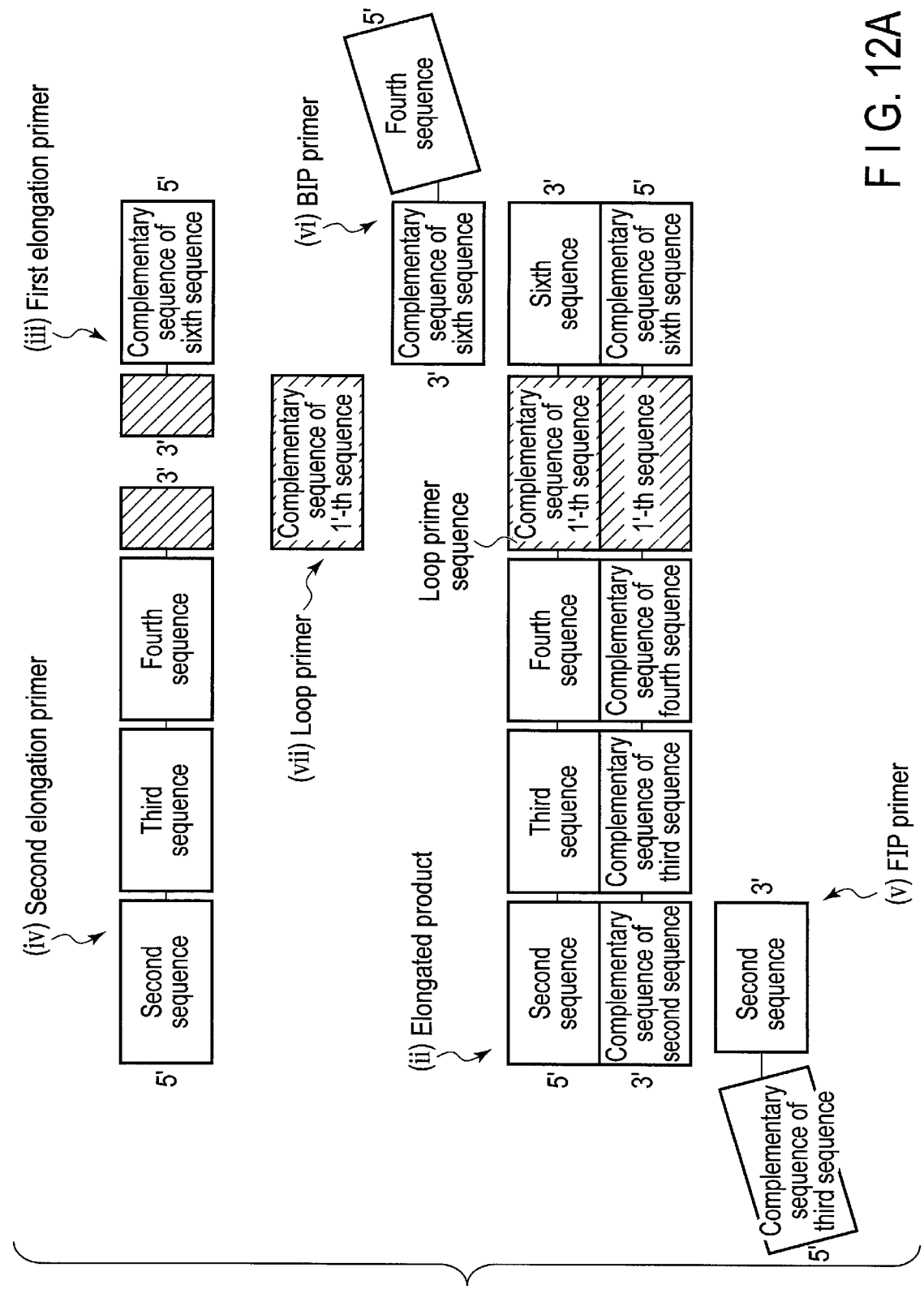
F I G. 12A

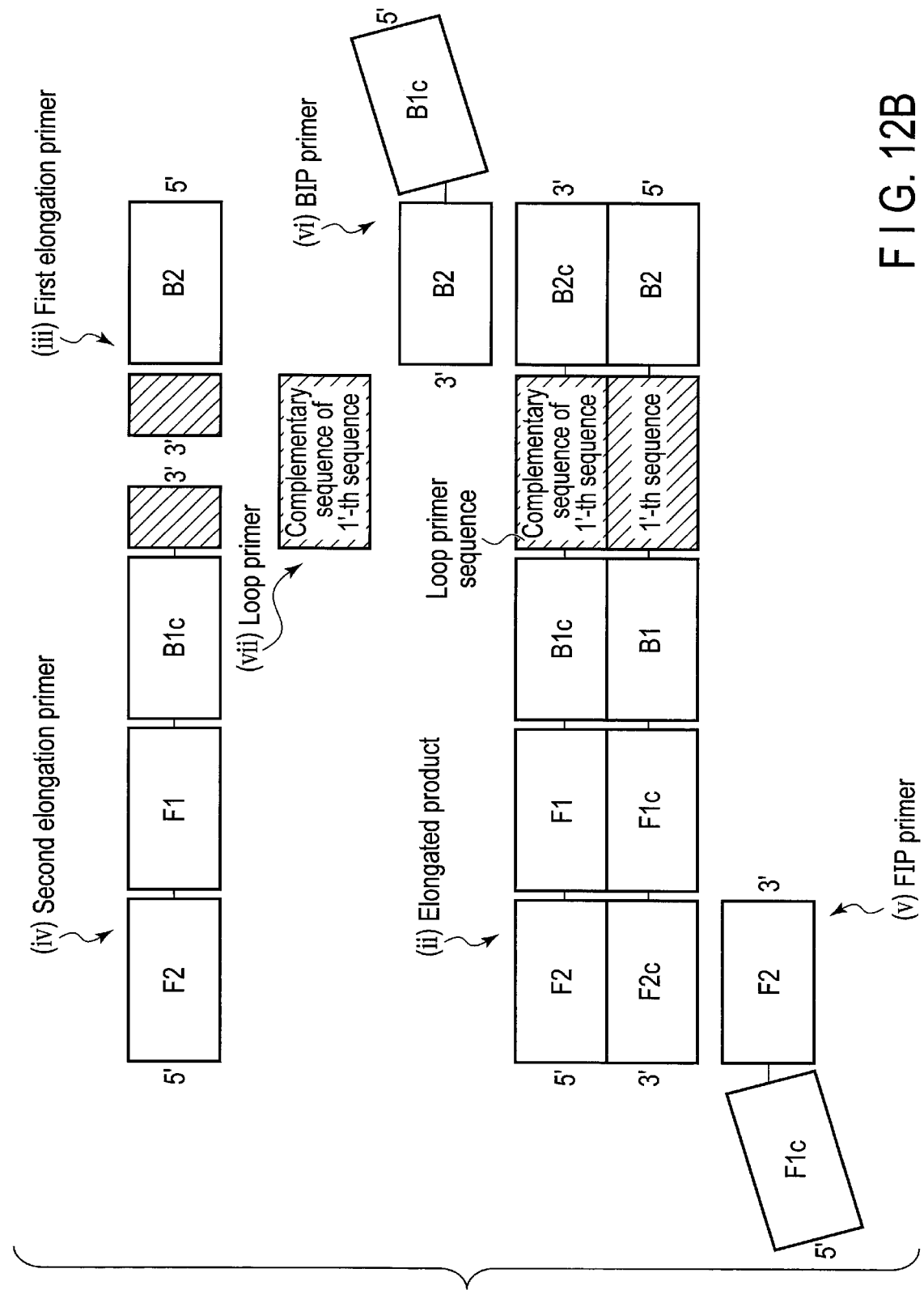
F I G. 12B

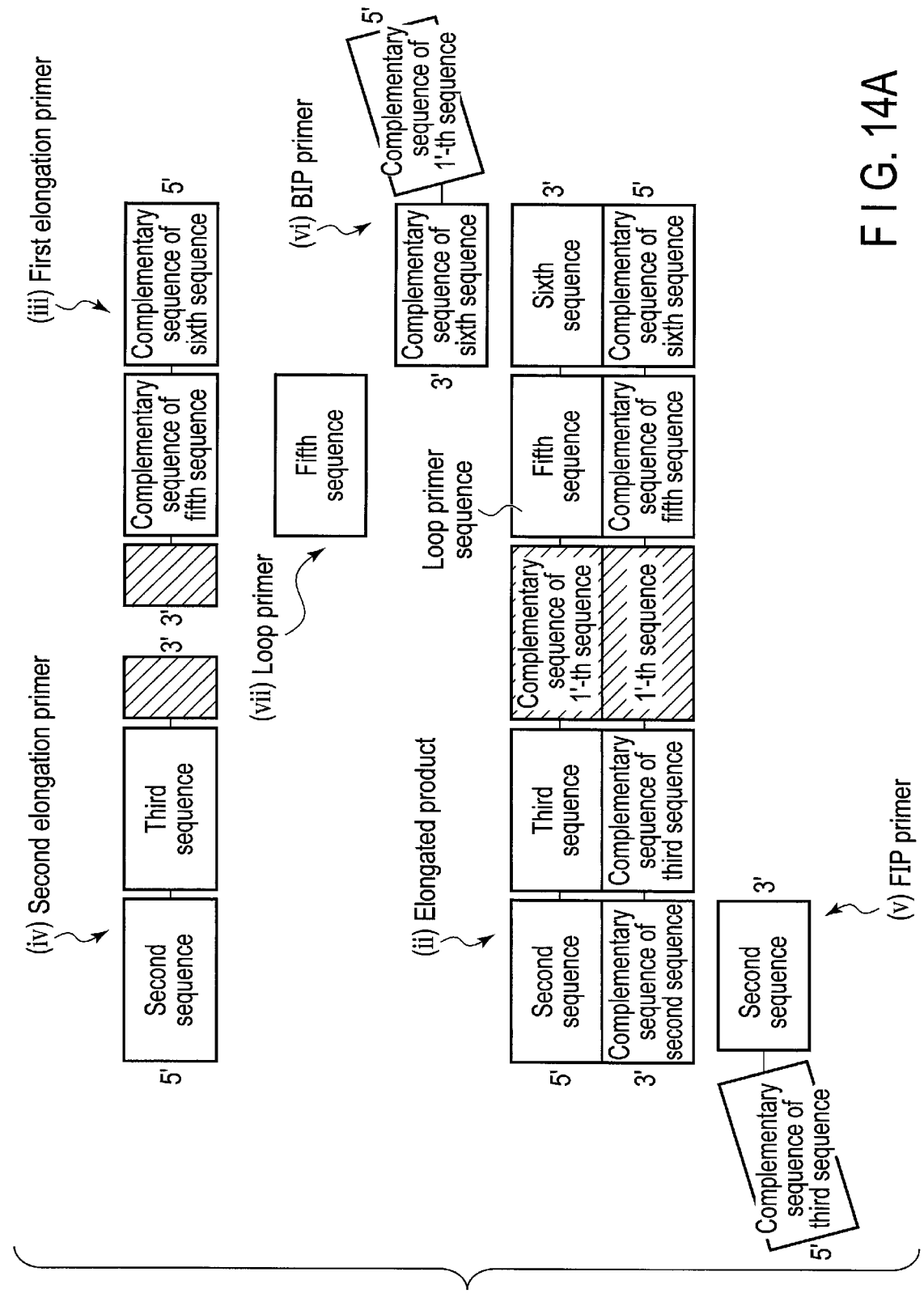
F I G. 14A

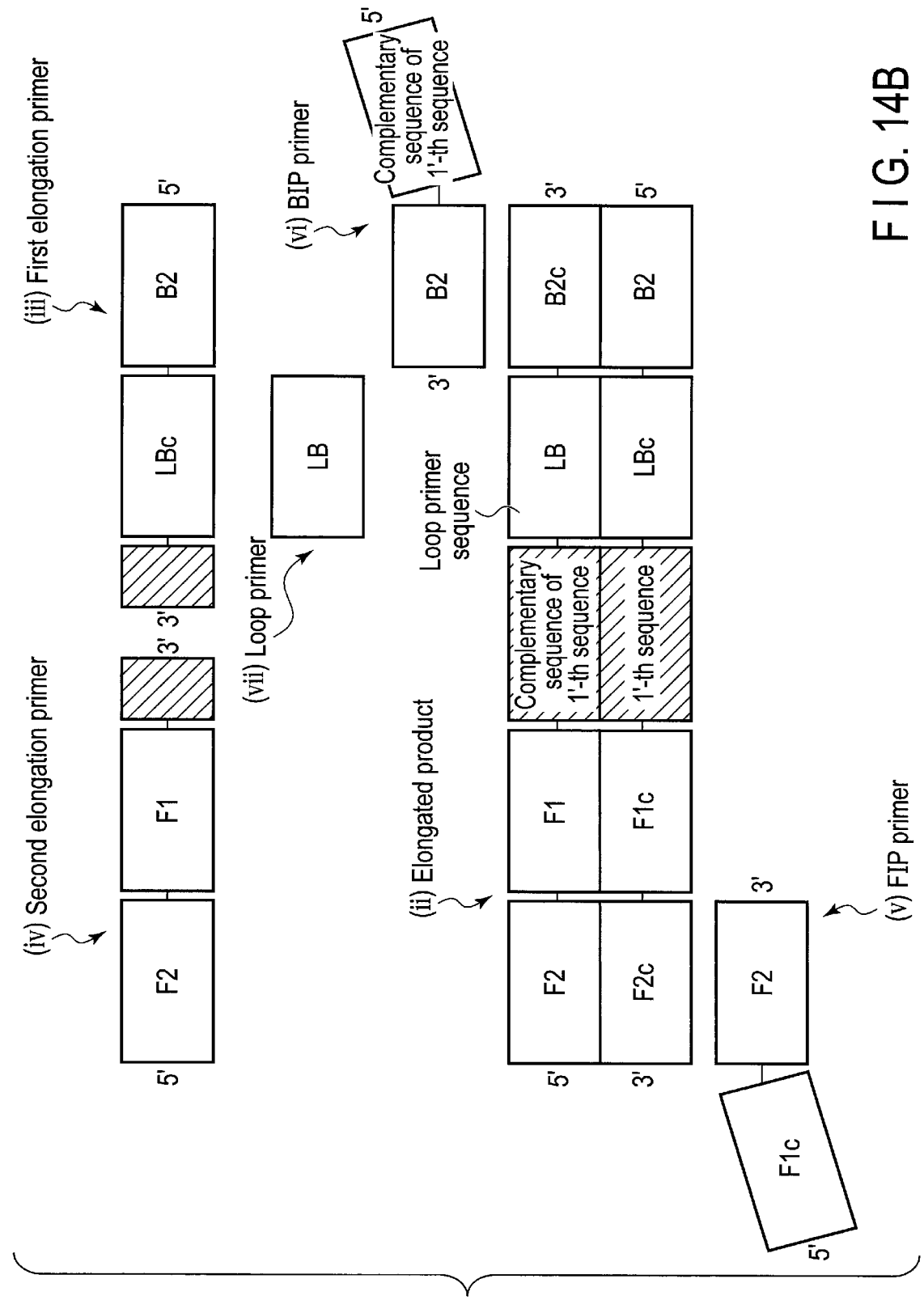
F I G. 14B

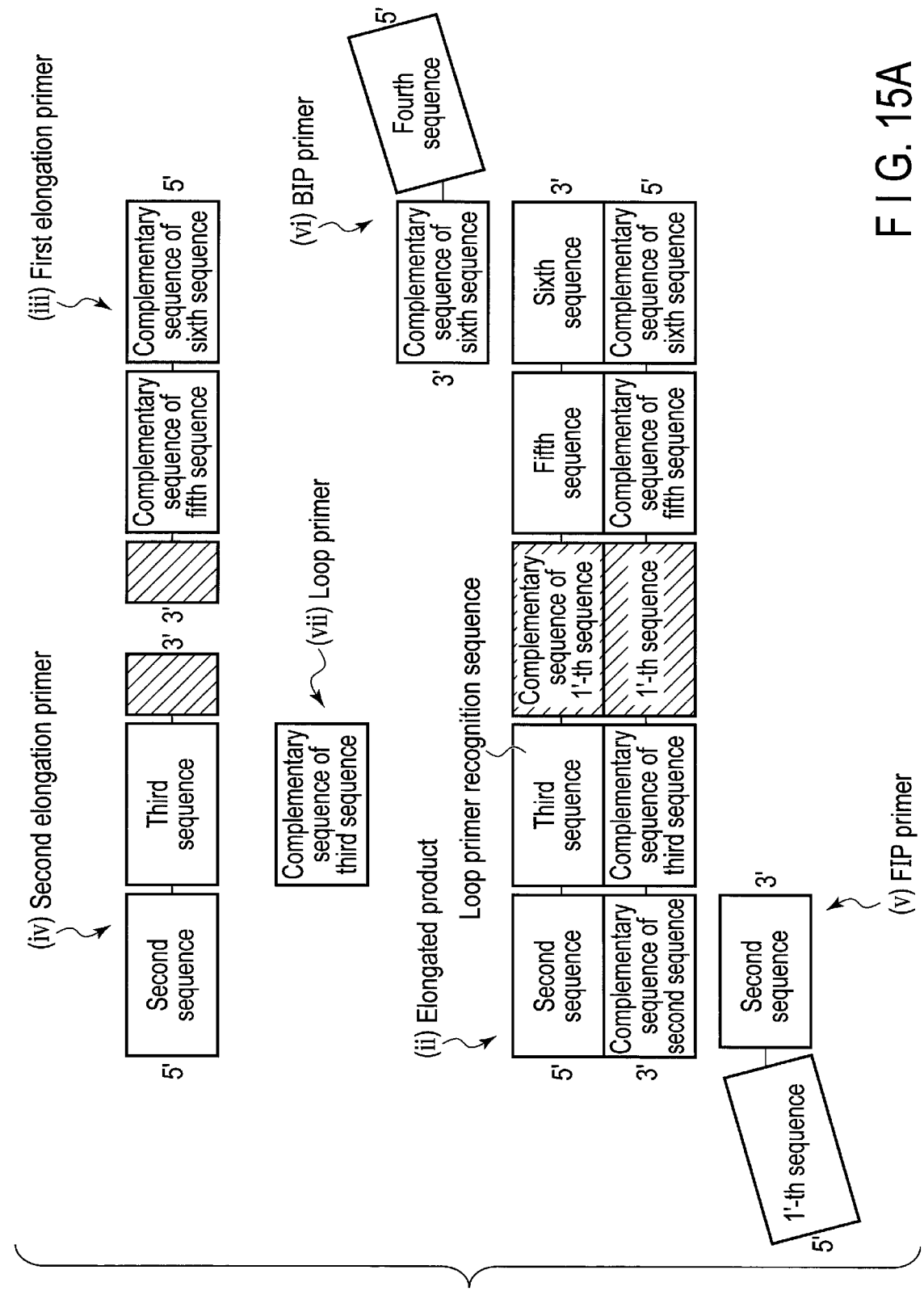
F I G. 15A

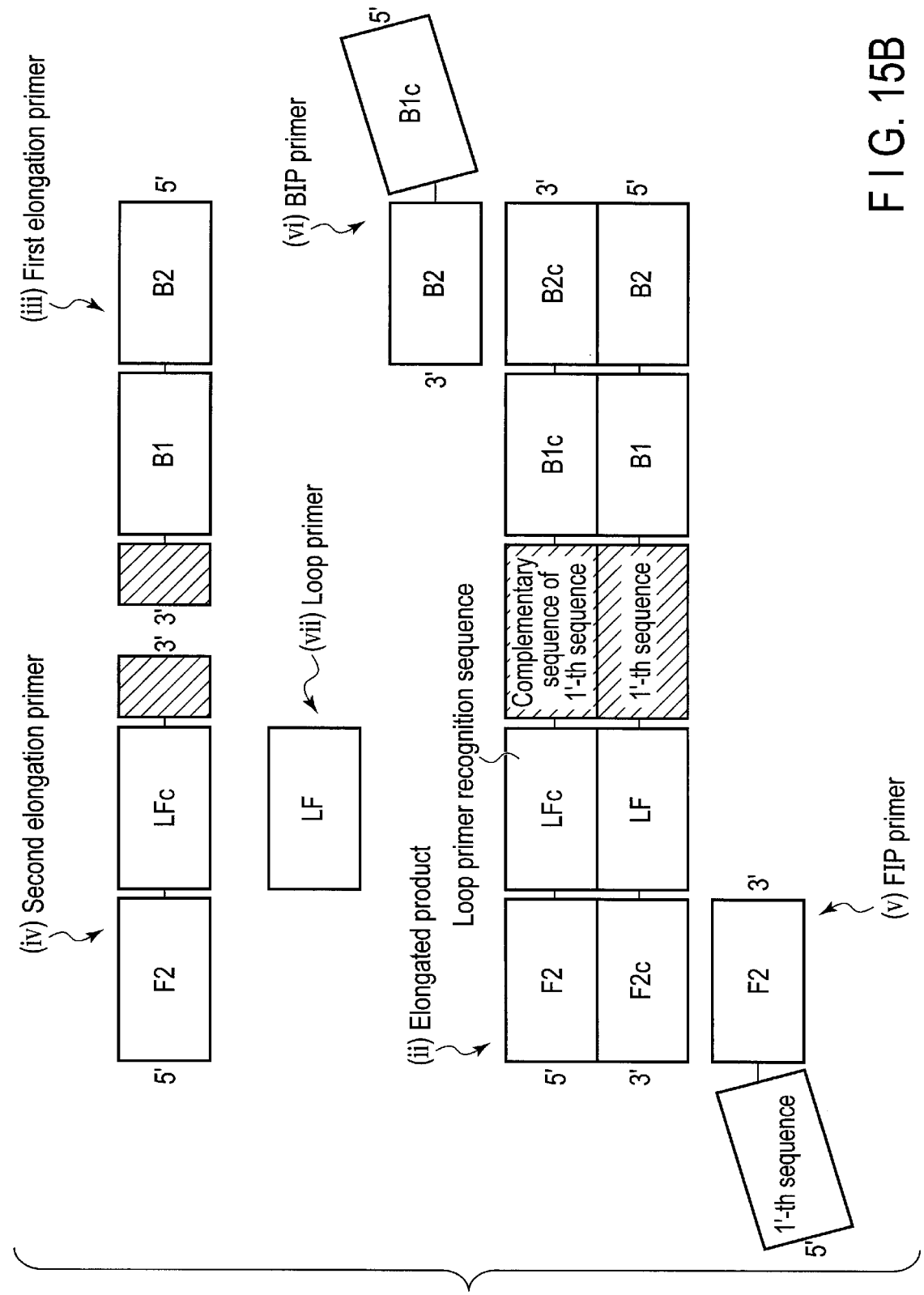
F I G. 15B

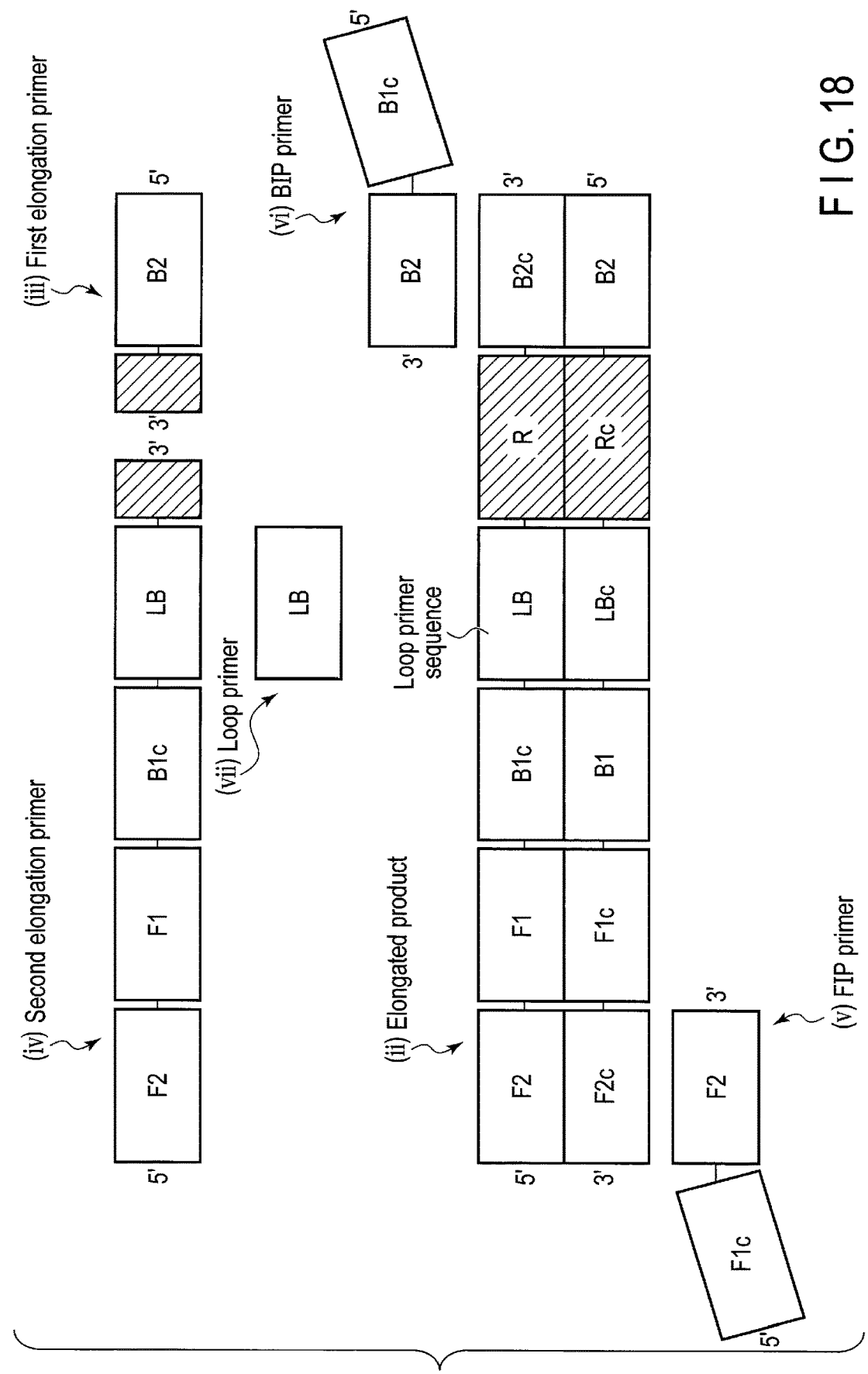
F I G. 18

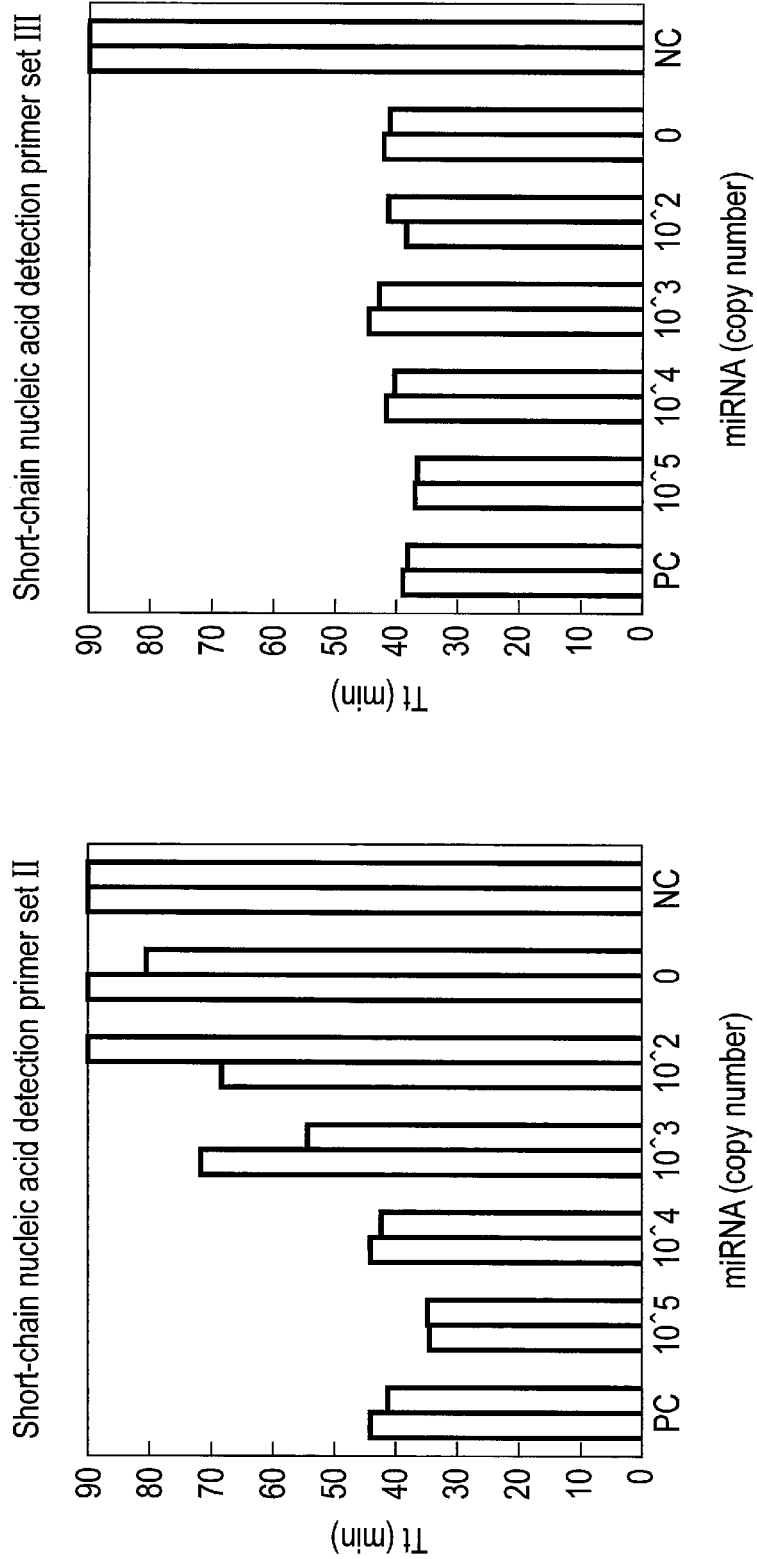
F I G. 19

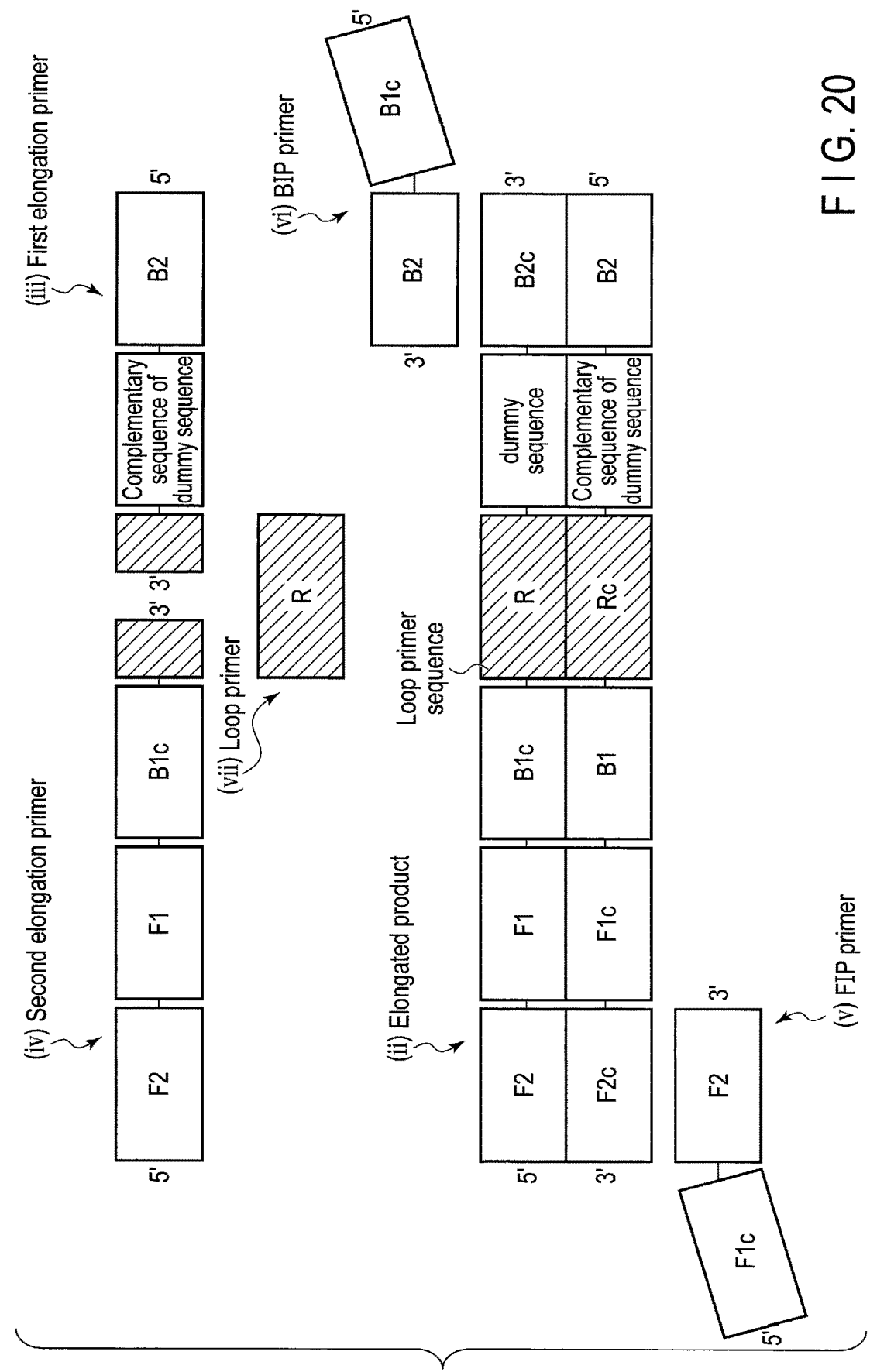
F I G. 20

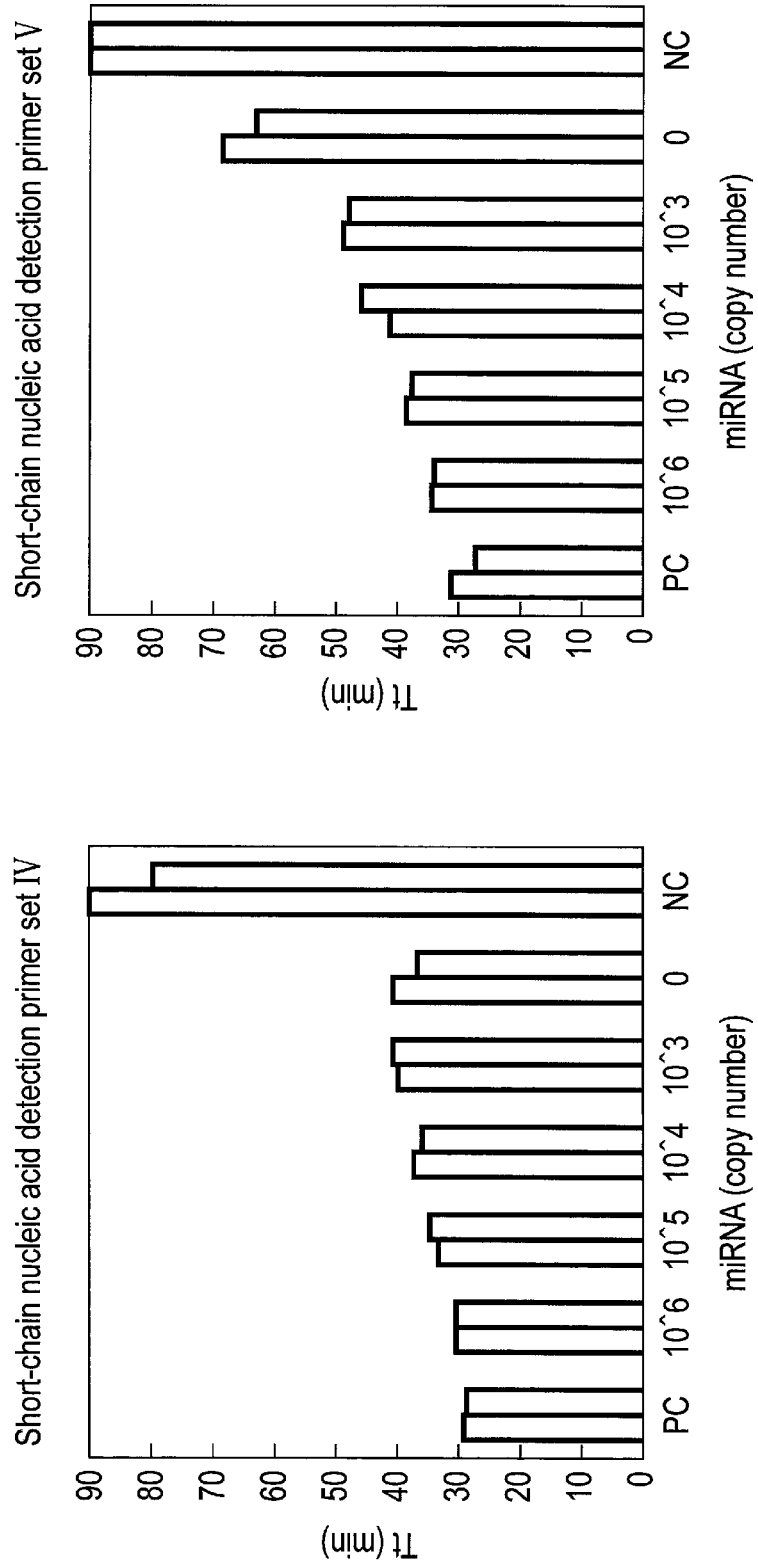
F I G. 21

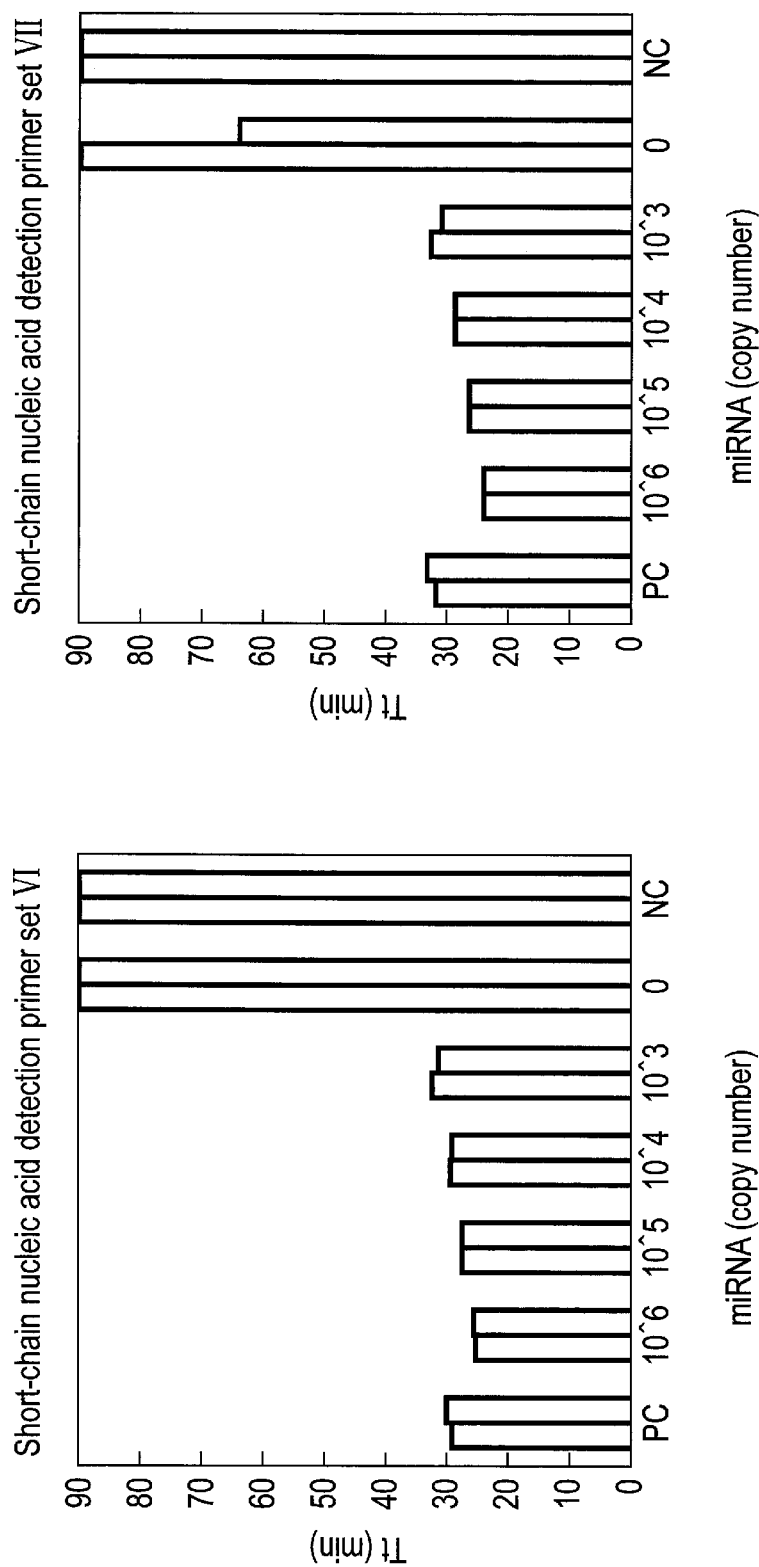
F I G. 23

SHORT-CHAIN NUCLEIC ACID ELONGATION PRIMER SET, ASSAY KIT, AND SHORT-CHAIN NUCLEIC ACID ELONGATION, AMPLIFICATION AND DETECTION METHODS

CROSS-REFERENCE TO RELATED APPLICATIONS

This application is based upon and claims the benefit of priority from Japanese Patent Applications No. 2017-135726, filed Jul. 11, 2017; and No. 2018-083156, filed Apr. 24, 2018, the entire contents of all of which are incorporated herein by reference.

FIELD

Embodiments described herein relate generally to a short-chain nucleic acid elongation primer set, an assay kit, and short-chain nucleic acid elongation, amplification and detection methods.

BACKGROUND

In various research fields, attention has been recently focused on short-chain RNA such as small interference RNA (siRNA) or microRNA (miRNA). siRNA is an artificially synthesized double stranded RNA of 21 to 23 bases and is used to suppress gene expression in vivo. It is known that miRNA is a single stranded RNA of about 17 to 25 bases, is present in cells, and has a function to regulate gene expression. Particularly, many reports have been made on the relationship between various diseases including cancer and the kind and expression level of miRNA. Further, since miRNA embedded in the exosome is present in serum, it is expected as a non-invasive diagnostic tool.

Such short-chain nucleic acid fragments are normally detected by Northern blotting, microarray analysis or real-time PCR. However, the sequence of the short-chain nucleic acid is short, it is difficult to ensure the primer annealing region. Therefore, there is difficulty in amplification, detection or sensitivity improvement. In order to clinically use the short-chain nucleic acid as a diagnostic tool, the development of the technology of detecting the short-chain nucleic acid is required.

BRIEF DESCRIPTION OF THE DRAWINGS

FIG. 1 is a pattern diagram illustrating an example of each of a target short-chain nucleic acid, an elongated product, and a short-chain nucleic acid elongation primer set of the first embodiment.

FIG. 2B is a pattern diagram illustrating an example of a step of obtaining an elongated product of the first embodiment.

FIG. 7A is a pattern diagram illustrating an example of each of an elongated product and a short-chain nucleic acid detection primer set of the first embodiment.

FIG. 8B is a pattern diagram illustrating an example of each of an elongated product and a short-chain nucleic acid detection primer set of the first embodiment.

FIG. 10 is a flow chart illustrating an example of a short-chain nucleic acid amplification method of the first embodiment.

FIG. 12A is a pattern diagram illustrating an example of each of an elongated product and a short-chain nucleic acid detection primer set of the second embodiment.

FIG. 12B is a pattern diagram illustrating an example of each of an elongated product and a short-chain nucleic acid detection primer set of the second embodiment.

FIG. 14A is a pattern diagram illustrating an example of each of an elongated product and a short-chain nucleic acid detection primer set of the third embodiment.

FIG. 14B is a pattern diagram illustrating an example of each of an elongated product and a short-chain nucleic acid detection primer set of the third embodiment.

FIG. 15A is a pattern diagram illustrating an example of each of an elongated product and a short-chain nucleic acid detection primer set of the third embodiment.

FIG. 15B is a pattern diagram illustrating an example of each of an elongated product and a short-chain nucleic acid detection primer set of the third embodiment.

FIG. 18 is a pattern diagram of a short-chain nucleic acid detection primer III set used in Example 2.

FIG. 19 is a graph showing experimental results in Example 2.

FIG. 20 is a pattern diagram of a short-chain nucleic acid detection primer set V used in Example 3.

FIG. 21 is a graph showing experimental results in Example 3.

FIG. 23 is a graph showing experimental results in Example 4.

DETAILED DESCRIPTION

Figure 2A:
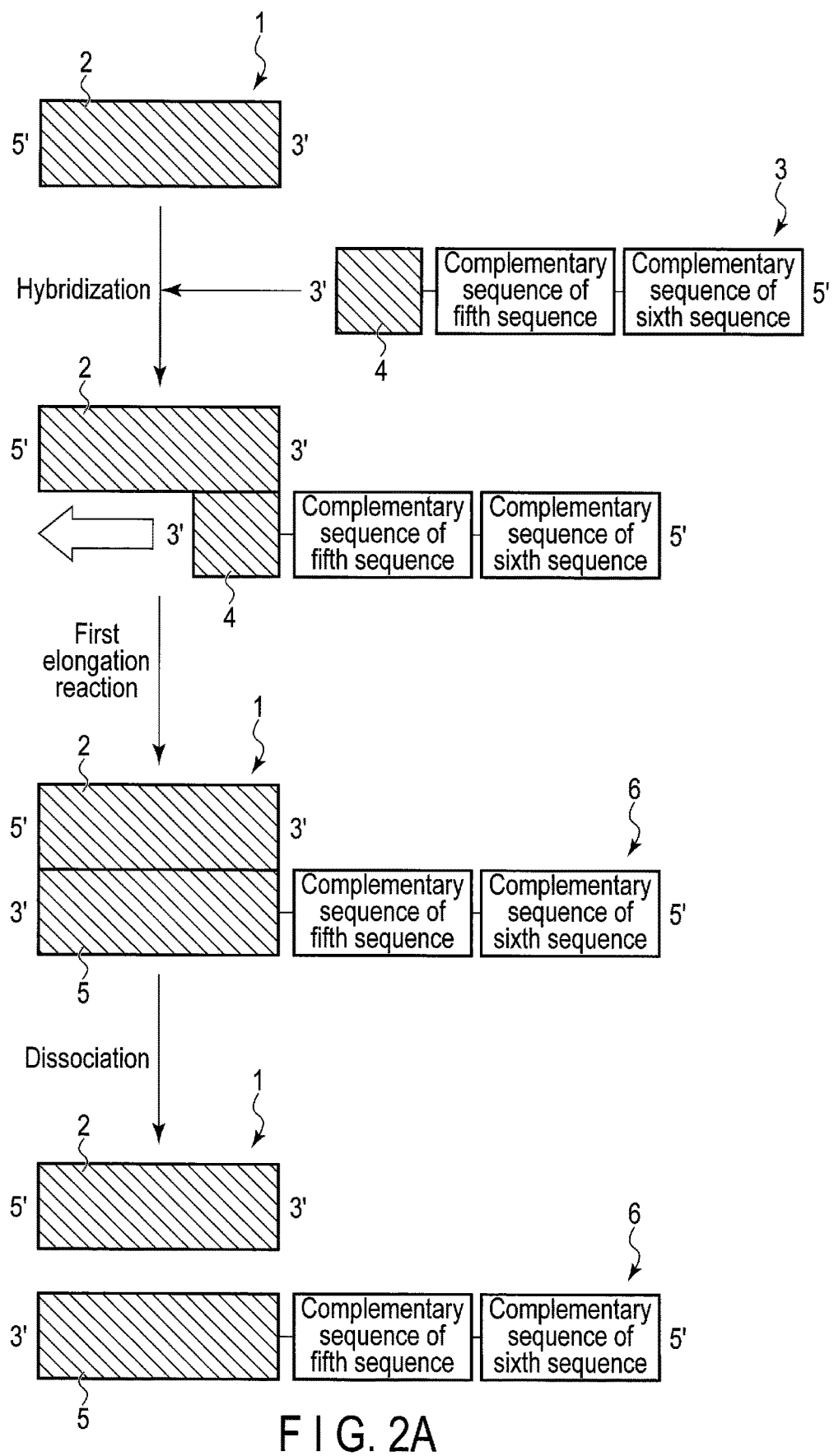
FIG. 2A is a pattern diagram illustrating an example of a step of obtaining an elongated intermediate product of the first embodiment.

In general, according to one embodiment, a short-chain nucleic acid elongation primer set is for elongating a target short-chain nucleic acid containing a first sequence to obtain an elongated product. The elongated product is a mutually complementary double-stranded nucleic acid, and one chain contains a second sequence, a third sequence, a fourth sequence, a sequence complementary to the complementary sequence of the first sequence (complementary sequence of the 1'-th sequence), and a sixth sequence in this order in a 3' to 5' direction. The complementary sequence of the 1'-th sequence is a loop primer sequence. The short-chain nucleic acid elongation primer set includes a first elongation primer containing a first elongation primer sequence which hybridizes with the first sequence and a complementary sequence of the sixth sequence in this order in the 3' to 5' direction and a second elongation primer containing a second elongation primer sequence which hybridizes with the 1'-th sequence, the fourth sequence, the third sequence, and the second sequence in this order in the 3' to 5' direction.

Hereinafter, various embodiments will be described with reference to the drawings. Each of the drawings is a pattern diagram for promoting explanation of the embodiments and their understanding. Although the shape, size, and ratio thereof are different from the actual shape, size, and ratio, the shape, size, and ratio thereof can be appropriately designed and changed taking into consideration the following descriptions and known technology.

First Embodiment

Short-Chain Nucleic Acid Elongation Primer Set

The short-chain nucleic acid elongation primer set according to the embodiment is a primer set which elongates a target short-chain nucleic acid in a sample to obtain an elongated product. For example, the elongated product is amplified, whereby the target short-chain nucleic acid in the sample can be detected or quantified.

FIG. 1 shows an example of each of the target short-chain nucleic acid, the elongated product, and the short-chain nucleic acid elongation primer set of the embodiment. A target short-chain nucleic acid (i) is a short-chain nucleic acid which is elongated using the short-chain nucleic acid elongation primer set in the short-chain nucleic acid elongation method of the embodiment to be described below. At least a part of the target short-chain nucleic acid (i) may be a nucleic acid containing a base sequence. The target short-chain nucleic acid is, for example, DNA, RNA, PNA, LNA, S-oligo or methyl phosphonate oligo. The target short-chain nucleic acid (i) may be a naturally occurring nucleic acid, or may be a partially or thoroughly artificially synthesized and/or designed nucleic acid. The target short-chain nucleic acid (i) has, for example, a length of about 50 bases or less.

For example, the target short-chain nucleic acid (i) is, for example, a short-chain RNA. The short-chain RNA may be, for example, a functional RNA, such as microRNA (miRNA), a small interfering RNA (siRNA), a small nuclear RNA (snRNA) or a small nucleolar RNA (snoRNA), or may not be a functional RNA. Alternatively, the short-chain RNA may be an artificial RNA or an RNA generated by fragmentation of RNA longer than 50 bases.

The target short-chain nucleic acid (i) contains a first sequence. As illustrated in FIG. 1, the first sequence is a consecutive sequence selected from the sequence over the entire length of the target short-chain nucleic acid (i). The first sequence may be an entire sequence of the target short-chain nucleic acid (i). The first sequence is a sequence which can serve as an indicator to detect or quantify the target short-chain nucleic acid (i). For example, the first sequence is preferably a sequence specific to the target short-chain nucleic acid (i) which is contained in the target short-chain nucleic acid (i). The first sequence is a sequence which should be elongated by the short-chain nucleic acid elongation primer set. It is preferable that the first sequence has, for example, a length of 3 to 10 bases, a length of from 10 to 20 bases, a length of from 20 to 30 bases, a length of from 30 to 40 bases or a length of from 40 to 50 bases. It is more preferable that the first sequence has a length of 10 to 50 bases. Note that a nucleic acid sequence having the same base sequence as that of complementary DNA (cDNA) of the first sequence (hereinafter, "a complementary sequence of the first sequence" referred to as "1'-th sequence") and the complementary sequence thereof should be amplified in the short-chain nucleic acid amplification method and the detection method of the embodiment to be described below.

Subsequently, the elongated product (ii) obtained by elongating the target short-chain nucleic acid (i) using the short-chain nucleic acid elongation primer set of the embodiment is described. The elongated product (ii) is a mutually complementary double-stranded nucleic acid. One chain of the elongated product contains the second sequence, the third sequence, the fourth sequence, the complementary sequence of the 1'-th sequence, the fifth sequence, and the sixth sequence in this order in the 3' to 5' direction. The other chain is a complementary sequence of the one chain and contains the complementary sequence of the second sequence, the complementary sequence of the third sequence, the complementary sequence of the fourth sequence, the 1'-th sequence, the complementary sequence of the fifth sequence, and the complementary sequence of the sixth sequence in the 3' to 5' direction.

The 1'-th sequence is a nucleic acid sequence which has the same base sequence as that of the complementary DNA of the first sequence. The 1'-th sequence may be, for example, the complementary DNA of the first sequence. Alternatively, the 1'-th sequence may be a nucleic acid sequence in which at least one nucleotide of the complementary DNA of the first sequence is replaced with a locked nucleic acid (LNA) and/or a peptide nucleic acid (PNA) having the same kind of base of the nucleotide.

The complementary sequence of the 1'-th sequence is a nucleic acid sequence having a base sequence corresponding to the base sequence of the first sequence. For example, when the target short-chain nucleic acid is an RNA, the base sequence of the complementary sequence of the 1'-th sequence is the same as the first sequence except that uracil (U) is thymine (T). Further, for example, when the target short-chain nucleic acid is a DNA, LNA or PNA, the base sequence of the complementary sequence of the 1'-th sequence is the same as the first sequence. The complementary sequence of the 1'-th sequence may be configured to be formed by only the DNA, or may contain the LNA and/or PNA.

Each of the second, third, fourth, fifth, and sixth sequences is a nucleic acid sequence having a base sequence different from the 1'-th sequence and the complementary sequence thereof. Further, each of the second, third, fourth, fifth, and sixth sequences has a mutually different base sequence. Each of the second, third, fourth, fifth, and sixth sequences may be configured to be formed by only the DNA, or may contain the LNA and/or PNA. For example, each of these sequences has preferably a length of 5 to 35 bases and more preferably a length of from 10 to 30 bases.

The base sequence of each of the second, third, fourth, fifth, and sixth sequences is preferably an artificial sequence. The artificial sequence is a base sequence which does not exist in nature. These sequences are artificial sequences, thereby preventing the sequences from binding to nucleic acids other than the target short-chain nucleic acid contained in the sample when producing the elongated product using the short-chain nucleic acid elongation primer set to be described below. This results in preventing the elongated product containing sequences other than the target short-chain nucleic acid from being produced. Thus, it is possible to prevent the detection result from being false positive.

The artificial sequence can be easily produced by, for example, creating four kinds of random number sequences and allocating each of the numbers to adenine (A), guanine (G), cytosine (C) or thymine (T). Further, it may be confirmed whether the thus produced artificial sequence exists in nature by BLAST search or the like. Then, sequences having no sequence that is the same as or similar to the artificial sequence are selected as the second sequence, the third sequence, sequence of the embodiment, thereby obtaining a more preferable artificial sequence.

Further, as the second, third, fourth, fifth, and sixth sequences, desired artificial sequences which are efficient as primer recognition sequences for LAMP may be produced or selected. In that case, the stability of amplification and the specificity during amplification of the elongated product are further improved.

Any one of the third sequence, the complementary sequence of the 1'-th sequence, and the fifth sequence is a loop primer sequence or a loop primer recognition sequence. The loop primer recognition sequence is a sequence to which the loop primer contained in the LAMP primer set to be described below is bound when amplifying the elongated product. The loop primer sequence is a complementary sequence of a loop primer recognition sequence. The loop primer sequence or the loop primer recognition sequence is contained, whereby the elongated product is rapidly and stably amplified.

One chain of the elongated product may contain a sequence except the second sequence, the third sequence, the fourth sequence, the complementary sequence of the first sequence, the fifth sequence, and the sixth sequence. For example, a spacer sequence may be present between the sequences of each of the second, third, fourth, or the complementary sequence of the 1'-th, fifth, and sixth sequences. The spacer sequence will be described for explanation of the first elongation primer and the second elongation primer.

The elongated product is obtained by elongating the first sequence using the first elongation primer and the second elongation primer which are contained in the short-chain nucleic acid elongation primer set to be described below. Accordingly, the configuration of the elongated product, i.e., the kind of nucleic acid and the base sequence are determined according to the configurations of the first elongation primer and second elongation primer.

The short-chain nucleic acid elongation primer set contains a first elongation primer (iii) and a second elongation primer (iv).

The first elongation primer (iii) is a single-stranded nucleic acid, and contains the first elongation primer sequence, the complementary sequence of the fifth sequence, and the complementary sequence of the sixth sequence in this order in the 3' to 5' direction.

The first elongation primer sequence is a nucleic acid sequence which hybridizes with the first sequence and serves as a primer for producing the complementary sequence (1'-th sequence) over the entire length of the first sequence. The first elongation primer sequence has, for example, at least five consecutive base sequences containing the 5' end of the 1'-th sequence. This sequence can hybridize with a consecutive base sequence containing the 3' end of the first sequence of the target short-chain nucleic acid.

The first elongation primer sequence may be configured to be formed by only the DNA, or may contain the LNA and/or PNA. The amount of LNA and/or PNA contained in the first elongation primer sequence is increased, thereby strengthening the binding force between the first elongation primer sequence and the first sequence. Therefore, the number of LNA and/or PNA to be contained may be determined according to a desired Tm value of the hybridization between the first sequence and the first elongation primer sequence. For example, the Tm value is increased by allowing the first elongation primer sequence to contain the LNA and/or PNA, whereby the first elongation reaction (described below) to be described below, which hybridizes the first sequence with the first elongation primer sequence to obtain an elongated intermediate product, can be performed at a higher temperature. Accordingly, it is possible to suppress a nonspecific binding and the complementary sequence of the first sequence is more specifically formed, and thus this is preferred. As a result, it is possible to detect the target short-chain nucleic acid with high accuracy.

For example, the first elongation primer sequence has preferably a length of from 5 to 20 bases, more preferably a length of from 6 to 15 bases, and still more preferably a length of from 7 to 12 bases.

The complementary sequence of the fifth sequence is a nucleic acid sequence complementary to the fifth sequence as described above. The complementary sequence of the sixth sequence is a nucleic acid sequence complementary to the sixth sequence as described above. The complementary sequence of the fifth sequence and the complementary sequence of the sixth sequence may be configured to be formed by only the DNA, or may contain the LNA and/or PNA.

A spacer sequence may be present between the first elongation primer sequence and the complementary sequences of the fifth sequence and a spacer sequence may be present between the complementary sequence of the fifth sequence and the complementary sequences of the sixth sequence. The spacer sequence is a nucleic acid sequence which is different from the second, third, fourth, 1'-th, fifth, and sixth sequences and the complementary sequences thereof and has no adverse effect on the amplification of the elongated product to be described below. The spacer sequence may be configured to be formed by only the DNA, or may contain the LNA and/or PNA. For example, the spacer sequence is preferably a poly T or poly A sequence or the like in order to prevent the first elongation primer from forming a secondary structure. For example, the spacer sequence preferably has a length of from 1 to 16 bases. However, it is preferable that the spacer sequence is not contained in the first elongation primer, because the first elongation primer can be designed to be shorter.

The first elongation primer preferably has an entire length of from 15 to 80 bases. The configuration over the entire length of the first elongation primer, namely, the base sequence may be selected and/or designed so as to obtain a desired elongated product. For example, the configuration of the elongated product to be obtained is first determined, and then the base sequence of the first elongation primer may be designed according to the configuration.

Subsequently, the second elongation primer (iv) will be explained. The second elongation primer (iv) is a single-stranded nucleic acid, and contains the second elongation primer sequence, the fourth sequence, the third sequence, and the second sequence in this order in the 3' to 5' direction.

The second elongation primer sequence is a nucleic acid sequence which serves as a primer for producing the complementary sequence over the entire length of the 1'-th sequence. For example, the second elongation primer sequence has at least five consecutive base sequences containing the 5' end of the complementary sequence of the 1'-th sequence. This sequence can hybridize with a consecutive base sequence containing the 3' end of the 1'-th sequence of the elongated intermediate product.

The second elongation primer sequence may be configured to be formed by only the DNA, or may contain the LNA and/or PNA. The amount of LNA and/or PNA contained in the second elongation primer sequence is increased, thereby strengthening the binding force between the second elongation primer sequence and the 1'-th sequence. Therefore, the number of LNA and/or PNA to be contained may be determined according to a desired Tm value of the hybridization between the 1'-th sequence and the second elongation primer sequence. For example, the Tm value is increased by allowing the second elongation primer to contain the LNA and/or PNA, whereby the second elongation reaction to be described below, which hybridizes the 1'-th sequence with the second elongation primer sequence to obtain an elongated product, can be performed at a higher temperature. Accordingly, it is possible to suppress a nonspecific binding, and thus this is preferred. As a result, it is possible to detect the target short-chain nucleic acid with high accuracy.

For example, the second elongation primer sequence has preferably a length of from 5 to 25 bases, more preferably a length of from 8 to 21 bases, and still more preferably a length of from 11 to 18 bases.

The second sequence, the third sequence, and the fourth sequence are the same nucleic acid sequences respectively as the second sequence, the third sequence, and the fourth sequence described above. Each of these sequences may be configured to be formed by only the DNA, or may contain the LNA and/or PNA.

A spacer sequence may be present between the second elongation primer sequence and the second sequence, between the second sequence and the third sequence, and/or between the third sequence and the fourth sequences. The spacer sequence is a DNA nucleotide sequence which is different from the second, third, fourth, 1'-th, fifth, and sixth sequences and the complementary sequences thereof and has no adverse effect on the LAMP of the elongated product to be described below. The spacer sequence may be configured to be formed by only the DNA, or may contain the LNA and/or PNA. For example, the spacer sequence is preferably a poly T or poly A sequence or the like in order to prevent the second elongation primer from forming a secondary structure. For example, the spacer sequence preferably has a length of from 1 to 16 bases. However, it is preferable that the spacer sequence is not contained in the second elongation primer, because the second elongation primer can be designed to be shorter.

In this regard, based on the reason that a binding force (Tm) when the second elongation primer hybridizes with the elongated intermediate product obtained using the first elongation primer is strengthened, it is preferable that the first extension reaction is performed using the M-MulV enzyme or an enzyme obtained by modifying M-MulV enzyme (e.g., SuperScript or MultiScribe), thereby allowing a spacer sequence to be present between the fourth sequence and the complementary sequence of the first sequence. In that case, the spacer sequence is preferably a poly G sequence.

The second elongation primer preferably has an entire length of from 25 to 130 bases. The configuration over the entire length of the second elongation primer, namely, the base sequence may be selected and/or designed so as to obtain a desired elongated product. For example, the configuration of the elongated product to be obtained is first determined, and then the base sequence of the second elongation primer may be designed according to the configuration.

An example of a step of elongating the target short-chain nucleic acid using the short-chain nucleic acid elongation primer set as described above to obtain an elongated product will be explained with reference to FIGS. 2A and 2B.

As illustrated in FIG. 2A, first, a first elongation primer sequence 4 of a first elongation primer 3 hybridizes with a first sequence 2 of a target short-chain nucleic acid 1. Next, the first DNA polymerase (not shown) to be described below elongates the first elongation primer sequence 4 of the 3' end in the 5' direction (indicated by an outlined arrow) using the first sequence 2 as a template. As a result, a 1'-th sequence 5 is produced (hereinafter, a series of the steps is referred to as "first elongation reaction").

When the target short-chain nucleic acid is an RNA, the first DNA polymerase is a reverse transcriptase in the first elongation reaction, and the 1'-th sequence is produced by reverse transcription of the first sequence using the first elongation primer.

Then, the target short-chain nucleic acid 1 is dissociated from the 1'-th sequence 5, thereby obtaining an elongated intermediate product 6 containing the 1'-th sequence 5, the complementary sequence of the fifth sequence, and the complementary sequence of the sixth sequence in this order.

After that, as illustrated in FIG. 2B, a second elongation primer sequence 9 of a second elongation primer 8 hybridizes with the 1'-th sequence 5 of the elongated intermediate product 6. Thereafter, the second DNA polymerase (not shown) to be described below elongates the second elongation primer 8 and the elongated intermediate product 6 using each other as the template. In other words, the 3' end of the second elongation primer 8 is elongated using the elongated intermediate product 6 as a template, and, the 3' end of the elongated intermediate product 6 is elongated using the second elongation primer 8 as a template (indicated by an outlined arrow). As a result, an elongated product 11 of double-stranded DNA is produced (hereinafter, a series of the steps illustrated in FIG. 2B is referred to as "second elongation reaction").

As explained above, according to the short-chain nucleic acid elongation primer set of the first embodiment, an elongated product of double-stranded nucleic acid containing six sequences is obtained using the first elongation primer having three sequences and the second elongation primer having four sequences.

Thus, the sequence length of the first elongation primer is designed shorter than that of the second elongation primer, whereby when the target short-chain nucleic acid is an RNA, it is possible to prevent the first elongation primer from forming a secondary in the reverse transcription reaction which may be performed at low temperature according to reverse transcriptase characteristics (first elongation reaction). Further, even if the longer second elongation primer has a secondary structure, the secondary structure is disassembled in the second elongation reaction to be performed at high temperature, thereby allowing for efficiently performing the second elongation reaction.

Further, the length of each of the base sequences of the first and second elongation primers of the first embodiment is designed shorter than that of the conventional short-chain nucleic acid elongation primer designed for LAMP. Thus, secondary structure formation of these primers and the elongated intermediate product hardly occurs compared to the conventional primers. As a result, the efficiency of the above-described first and second elongation reactions is improved, and further a nonspecific elongated intermediate product and a nonspecific elongated product are hardly produced. Further, the number of primer recognition sequences of the elongated product of the embodiment is smaller than that of the conventional elongated product for LAMP in which the short-chain nucleic acid is elongated, but the elongated product of the embodiment contains a loop primer sequence or a loop primer recognition region. Thus, it is possible that the elongated product is rapidly and stably amplified.

Further, when the elongated product of the embodiment is amplified, nonspecific amplification hardly occurs, and the elongated product is efficiently amplified even if the abundance of the short-chain nucleic acid is low. Therefore, the short-chain nucleic acid elongation primer set of the embodiment is used so that it is possible to detect and quantify the short-chain nucleic acid with high accuracy.

Figure 4:
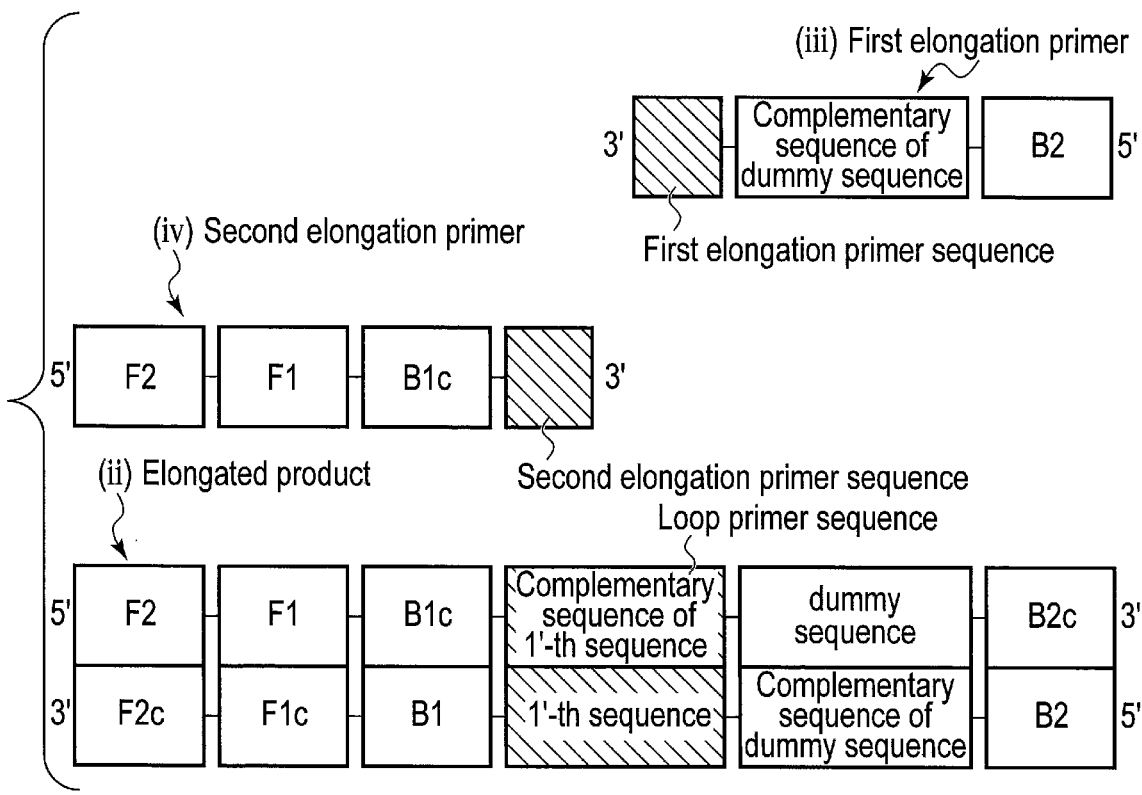
FIG. 4 is a pattern diagram illustrating an example of each of an elongated product and a short-chain nucleic acid elongation primer set of the first embodiment.
Figure 5:
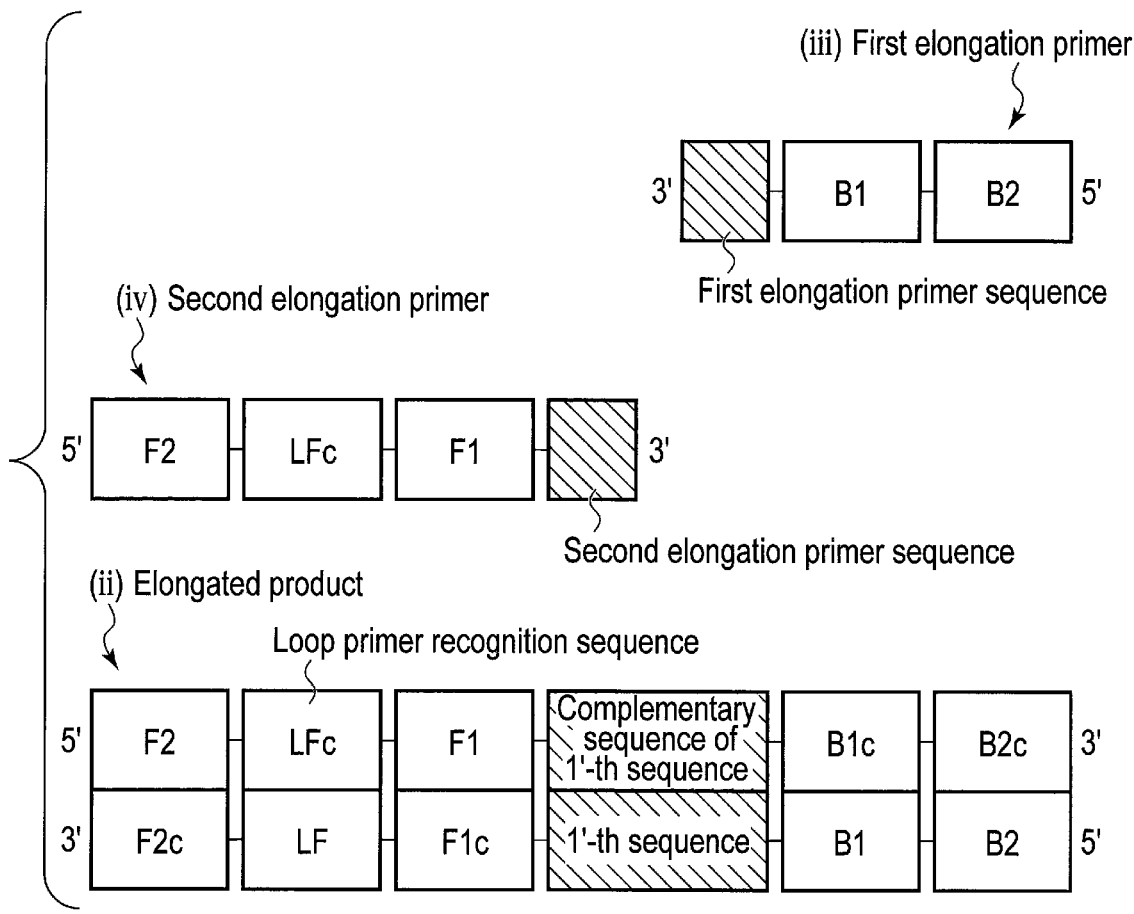
FIG. 5 is a pattern diagram illustrating an example of each of an elongated product and a short-chain nucleic acid elongation primer set of the first embodiment.

Each of the sequences included in the above-described short-chain nucleic acid elongation primer set and the elongated product may be a recognition sequence to which the LAMP primer binds. Examples thereof are illustrated in FIGS. 3 to 5.

Figure 3:
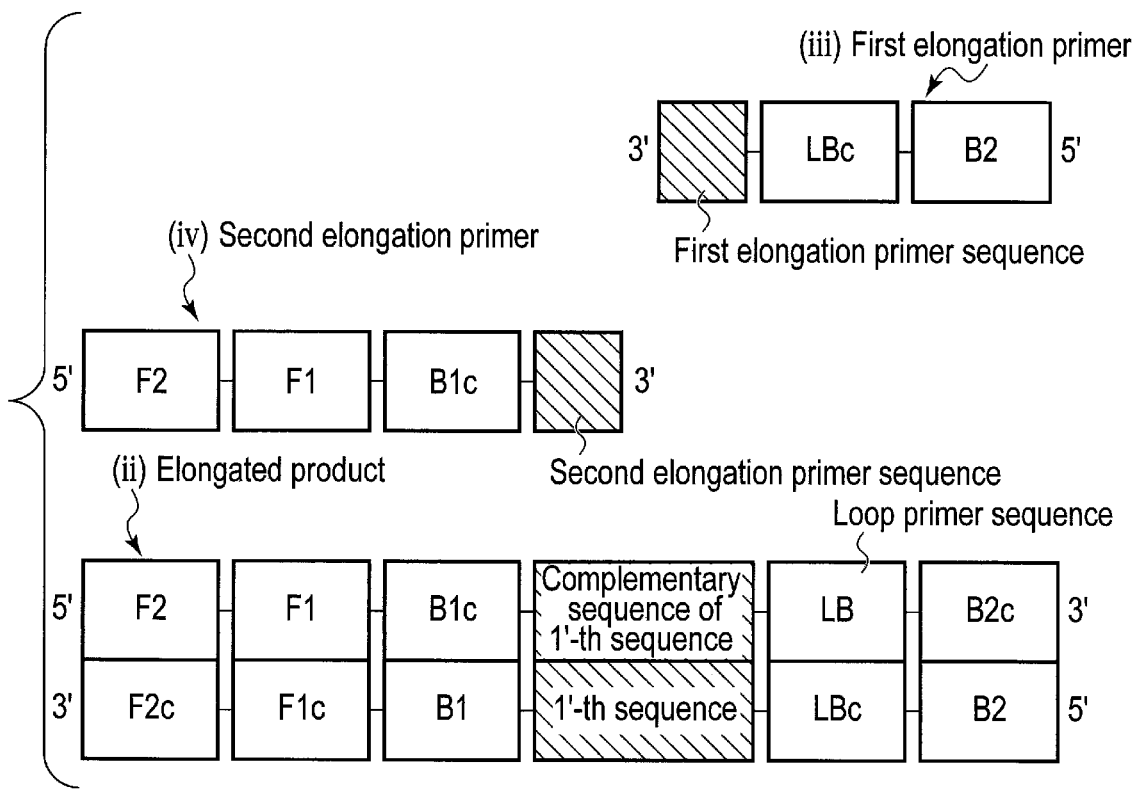
FIG. 3 is a pattern diagram illustrating an example of each of an elongated product and a short-chain nucleic acid elongation primer set of the first embodiment.

Regarding the short-chain nucleic acid elongation primer set and the elongated product to be obtained using the primer set illustrated in FIG. 3, the second sequence is an F2 sequence, the third sequence is an F1 sequence, the fourth sequence is a B1c sequence, the fifth sequence is a LB sequence, and the sixth sequence is a B2c sequence.

Therefore, the first elongation primer in this example contains the first elongation primer sequence, an LBc sequence, and a B2 sequence in this order in the 3' to 5' direction. The second elongation primer contains the second elongation primer sequence, a B1c sequence, an F1 sequence, and an F2 sequence in this order in the 3' to 5' direction. Regarding the elongated product, one chain contains the F2, F1, and B1c sequences, the complementary sequence of the 1'-th sequence, and the LB and B2c sequences in this order in the 3' to 5' direction, and the other chain contains the F2c, F1c, B1, 1'-th, LBc, and B2 sequences in this order in the 3' to 5' direction. Here, the F2 sequence is complementary to the F2c sequence, the F1 sequence is complementary to the F1c sequence, the B1 sequence is complementary to the B1c sequence, the B2 sequence is complementary to the B2c sequence, and the LB sequence is complementary to the LBc sequence (the same holds true for the following explanations). In this example, the fifth sequence, i.e., the LB sequence is the loop primer sequence.

According to the short-chain nucleic acid elongation primer set which has such a sequence, the short-chain nucleic acid can be elongated more specifically and efficiently.

Regarding the short-chain nucleic acid elongation primer set and the elongated product to be obtained using the primer set illustrated in FIG. 4, the second sequence is the F2 sequence, the third sequence is the F1 sequence, the fourth sequence is the B1c sequence, the fifth sequence is a dummy sequence, and the sixth sequence is the B2c sequence.

The dummy sequence is a nucleic acid sequence having a base sequence different from the 1'-th, F2, F1, B1, and B2 sequences and the complementary sequences thereof. Further, the dummy sequence is a nucleic acid sequence having a base sequence different from any of the recognition sequences contained in the LAMP primer in order to amplify the elongated product to be described below and the complementary sequences thereof.

Therefore, the first elongation primer in this example contains the first elongation primer sequence, a complementary sequence of the dummy sequence, and a B2 sequence in this order in the 3' to 5' direction. The second elongation primer contains the second elongation primer sequence, a B1c sequence, an F1 sequence, and an F2 sequence in this order in the 3' to 5' direction. Regarding the elongated product, one chain contains the F2, F1, and B1c sequences, the complementary sequence of the 1'-th sequence, and the dummy and B2c sequences in this order in the 3' to 5' direction, and the other chain contains the F2c, F1c, B1, and 1'-th sequences, the complementary sequence of the dummy sequence, and the B2 sequence in this order in the 3' to 5' direction. In this example, the complementary sequence of the 1'-th sequence is the loop primer sequence.

According to the short-chain nucleic acid elongation primer set which has such a sequence, the loop primer binds to the 1'-th sequence during amplification of the obtained elongated product, whereby the amplification reaction is accelerated and amplification products are stably produced. Therefore, when the elongation is not correctly performed, and the 1'-th sequence and the complementary sequence thereof are not produced, the amplification product is not stably produced. In other words, when a desired elongated product containing the 1'-th sequence and the complementary sequence thereof is produced, the amplification product is stably obtained and the nonspecific elongated product is hardly amplified. Thus, according to the above-described short-chain nucleic acid elongation primer set, the short-chain nucleic acid can be more specifically detected or quantified with high accuracy.

Regarding the short-chain nucleic acid elongation primer set and the elongated product to be obtained using the primer set illustrated in FIG. 5, the second sequence is an F2 sequence, the third sequence is an LFc sequence, the fourth sequence is an F1 sequence, the fifth sequence is a B1c sequence, and the sixth sequence is a B2c sequence.

Therefore, the first elongation primer contains the first elongation primer sequence and B1 and B2 sequences in this order in the 3' to 5' direction. The second elongation primer contains the second elongation primer sequence and the F1, LFc, and F2 sequences in this order in the 3' to 5' direction. Regarding the elongated product, one chain contains the F2, LFc, and F1 sequences, the complementary sequence of the 1'-th sequence, and the B1c and B2c sequences in this order in the 3' to 5' direction, and the other chain contains the F2c, LF, F1c, 1'-th, B1, and B2 sequences in this order in the 3' to 5' direction. Here, the LF sequence is complementary to the LFc sequence. In this example, the third sequence, i.e., the LFc sequence is the loop primer recognition sequence.

According to the short-chain nucleic acid elongation primer set which has such a sequence, the short-chain nucleic acid can be elongated more specifically and efficiently.

The base sequences of the sequences included in the short-chain nucleic acid elongation primer set may be determined based on the base sequences of the LAMP primer set.

For example, according to base sequences in the pre-determined LAMP primer set having excellent amplification efficiency, the base sequences in the short-chain nucleic acid elongation primer set are determined, whereby the elongated product to be produced using the short-chain nucleic acid elongation primer set is more efficiently amplified.

Short Chain Nucleic Acid Elongation Method

Figure 6:
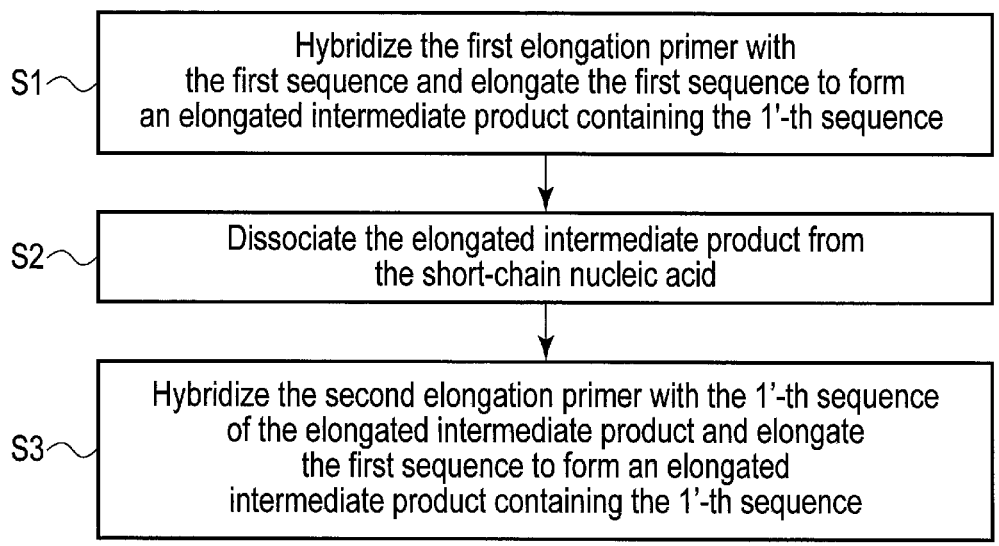
FIG. 6 is a flow chart illustrating an example of a short-chain nucleic acid elongation method of the first embodiment.

Hereinafter, the method of elongating a short-chain nucleic acid using the above-described short-chain nucleic acid elongation primer set will be explained. FIG. 6 is a schematic flow illustrating an example of a short-chain nucleic acid elongation method of an embodiment. The method is for elongating a target short-chain nucleic acid containing a first sequence in a sample, and includes the following steps (S1) to (S3):

hybridizing the first elongation primer with the first sequence and elongating the first sequence to obtain an elongated intermediate product containing the 1'-th sequence (S1);

dissociating the elongated intermediate product from the target short-chain nucleic acid (S2); and hybridizing the second elongation primer with the 1'-th sequence of the elongated intermediate product and elongating the second elongation primer and the elongated intermediate product to obtain an elongated product (S3).

Hereinafter, each step of the short-chain nucleic acid elongation method will be explained in detail.

In the step (S1), the first sequence is elongated by hybridizing the first elongation primer with the first sequence, and elongating the first sequence to obtain an elongated intermediate product containing the 1'-th sequence. The step (S1) can be performed by, for example, maintaining a first elongation reaction solution containing a sample, the first elongation primer set, and the first DNA polymerase under first elongation reaction conditions.

The sample is a sample to be analyzed and may contain the target short-chain nucleic acid. Examples of the sample may include substances such as blood, serum, white blood cells, lymph fluid, cerebrospinal fluid, urine, feces, sperm, sweat, saliva, mucous membrane in the oral cavity, sputum, tear fluid, mother milk, amniotic fluid, tissue, biopsy, isolated or cultured cells, which are extracted from animals; organs, isolated cells, cultured cells or extracts of plants; mixtures containing microorganisms, bacteria, fungi or viruses; environmental substances extracted from the environment; mixtures containing synthetic RNA; or materials of any of those mixtures. Alternatively, the sample may be a preparation obtained by preparing these materials.

The animals may be, for example, mammals, birds, amphibians, reptiles, fishes or arthropods, or may be other organisms belonging to the animal kingdom. The mammals may be any of mammals, for example, primates such as monkeys and humans, rodents such as mice and rats, companion animals such as dogs, cats, and rabbits, livestock such as horses, cows, and pigs.

It is preferable that the sample is in a state which does not block the amplification reaction. The sample is in such a state, whereby the target short-chain nucleic acid can be more efficiently amplified in the short-chain nucleic acid amplification method of the embodiment. The term "state which does not block the amplification reaction" means, for example, a state in which the kind of each of the components in the sample, the combination of the components or the concentration of the components does not reduce, delay or stop the amplification reaction rate.

When each of the above-described material is in the state which does not block the amplification reaction, the material may be directly used as the sample. Alternatively, the obtained material is pre-treated by, for example, any of the known means to obtain a sample in the state which does not block the amplification reaction or in a state more suitable for amplification. The pretreatment is, for example, chopping, homogenization, centrifugation, precipitation, extraction or separation.

For example, the extraction may be performed using a commercially available nucleic acid extraction kit. Examples of the nucleic acid extraction kit to be used include PureLink (registered trademark) miRNA Isolation Kit (manufactured by Thermo Fisher Scientific Inc.), MicroRNA Extractor (registered trademark) SP Kit (manufactured by Wako Pure Chemical Industries, Ltd.), NucleoSpin (registered trademark) miRNA (manufactured by TAKARA BIO INC.), MirPremier (registered trademark) microRNA Isolation Kit (manufactured by Sigma-Aldrich Co. LLC.), High Pure miRNA Isolation Kit (manufactured by Roche Life Science), PAXgene™ Blood miRNA Kit, miRNeasy Serum/Plasma Kit (both are manufactured by QIAGEN), MiRCURY (registered trademark) RNA Isolation Kit-Bifluids (manufactured by Exiqon), and Plasma/Serum RNA Purification Mini Kit (manufactured by Norgen Biotek Corp.), and the nucleic acid extraction kit is not limited thereto. Alternatively, these kits are not used, for example, a sample may be obtained by diluting materials with a buffer solution, subjecting the resulting diluted solution to heat treatment at 80 to 100° C., centrifuging the solution, and extracting the supernatant.

As the first elongation primer, for example, any of the above-described first elongation primers can be used.

The first DNA polymerase may be any of known DNA polymerases and is selected depending on the kind of the first elongation primer and/or the kind or sequence of the target short-chain nucleic acid. As the first DNA polymerase, for example, Klenow Fragment (Large Fragment $E.$ $coli$ DNA polymerase I), T4 DNA polymerase, phi29 DNA polymerase, Bst DNA polymerase, Csa DNA polymerase, 96-7 DNA Polymerase, Vent™(exo-) DNA polymerase, DeepVent™(exo-) DNA polymerase, GspSSD DNA polymerase or Tin exo-DNA polymerase can be used. Alternatively, other DNA polymerases which are commonly used for PCR amplification (such as Taq DNA polymerase) can be used. Alternatively, reverse transcriptases (such as M-MuLV reverse transcriptase and Transcriptor reverse transcriptase) with which amplification can be performed using DNA as a template can be used.

When the target short-chain nucleic acid is an RNA, the first DNA polymerase is, for example, a reverse transcriptase. As the reverse transcriptase, for example, M-MuLV reverse transcriptase, AMV reverse transcriptase, Transcriptor reverse transcriptase, Superscript (registered trademark) transcriptor reverse transcriptase, or MultiScribe™ reverse transcriptase can be used.

When the first elongation primer contains the LNA and/or PNA, a heat-resistant DNA polymerase is preferably used as the first DNA polymerase.

In addition to these components, the first elongation reaction solution may further contain a desired component necessary for the first elongation reaction. The component may be, for example, a salt, a substrate such as deoxynucleoside triphosphate (dNTPs), a thickener as a reaction reagent, a pH adjustment buffer, a surfactant, an ion for increasing the annealing specificity, and/or an ion serving as a cofactor of reverse transcriptase.

The above-described first elongation reaction solution is maintained under the first elongation reaction conditions, whereby the first elongation reaction occurs, and thus it is possible to obtain the above-described elongated intermediate product containing the 1'-th sequence, the complementary sequence of the fifth sequence, the complementary sequence of the sixth sequence. The first elongation reaction conditions may be selected depending on the kind of the first elongation primer, the kind of the elongated intermediate product and/or the kind of the DNA polymerase based on common knowledge of those skilled in the art. The reaction temperature of the first elongation reaction is, for example, from about 10 to 55° C. The first elongation reaction can be performed by keeping the reaction temperature at a constant level, keeping a plurality of temperature zones for a certain period of time, or repeating the temperature zones in a plurality of cycles. When the first elongation primer contains the LNA and/or PNA, the reaction temperature of the first elongation reaction is preferably from 20 to 65° C.

For example, the reaction temperature is kept as described above, whereby an elongated intermediate product being bound to the target short-chain nucleic acid is obtained in the step illustrated in FIG. 2A.

Then, in the step (S2), the elongated intermediate product is dissociated from the target short-chain nucleic acid. The dissociating can be performed by, for example, heating the first elongation reaction solution to 80 to 100° C. after the first elongation reaction.

When the target short-chain nucleic acid is an RNA, the target short-chain nucleic acid is dissociated by the heating, and at the same time, the reverse transcriptase (first DNA polymerase) may be inactivated. As a result, it is possible to prevent the reverse transcriptase from having an adverse effect on the subsequent steps after the step (S3).

Subsequently, in the step (S3), the second elongation primer hybridizes with the 1'-th sequence of the elongated intermediate product, and the second elongation primer and the elongated intermediate product are elongated to obtain an elongated product. The step (S3) can be performed by, for example, maintaining a second elongation reaction solution containing the elongated intermediate product obtained in the step (S2), the second elongation primer, and the second DNA polymerase under second elongation reaction conditions.

As the second elongation primer, for example, any of the above-described second elongation primer can be used.

The second DNA polymerase may be any of known DNA polymerases and is selected depending on the kind of the second elongation primer and/or the sequence of the elongated intermediate product. As the second DNA polymerase, Klenow Fragment (Large Fragment E. coli DNA polymerase I), T4 DNA polymerase, phi29 DNA polymerase, Bst DNA polymerase, Csa DNA polymerase, 96-7 DNA Polymerase, Vent™(exo-) DNA polymerase, DeepVent™(exo-) DNA polymerase, GspSSD DNA polymerase or Tin exo-DNA polymerase can be used. Alternatively, other DNA polymerases which are commonly used for PCR amplification (such as Taq DNA polymerase) can be used. Alternatively, reverse transcriptases (such as M-MuLV reverse transcriptase and Transcriptor reverse transcriptase) with which amplification can be performed using DNA as a template can be used. When the first elongation reaction and the second elongation reaction can be performed by the same kind of DNA polymerase, i.e., when the target short-chain nucleic acid is a DNA, LNA, PNA or the like, the first DNA polymerase may be used as the second DNA polymerase. In that case, it is not necessary to add the second DNA polymerase to the reaction solution before performing the second elongation reaction, and the second elongation reaction may be performed using a solution obtained by adding a component of the second elongation reaction solution except for DNA polymerase to the first elongation reaction solution.

When the second elongation primer contains the LNA and/or PNA, a heat-resistant DNA polymerase is preferably used as the second DNA polymerase.

In addition to these components, the second elongation reaction solution may further contain a desired component necessary for the second elongation reaction. The component may be, for example, a salt, a substrate such as dNTPs, a thickener as a reaction reagent, a pH adjustment buffer, a surfactant, an ion for increasing the annealing specificity, and/or an ion serving as a cofactor of reverse transcriptase.

The above-described second elongation reaction solution is maintained under the elongation reaction conditions, whereby the second elongation reaction occurs, and thus it is possible to obtain the elongated product. The elongated product is a mutually complementary double-stranded nucleic acid, and one chain contains the second, third, and fourth sequences, the complementary sequence of the 1'-th sequence, and the fifth and sixth sequences in this order in the 3' to 5' direction. Any one of the third sequence, the complementary sequence of the 1'-th sequence, and the fifth sequence is a loop primer sequence or a loop primer recognition sequence.

The second elongation reaction conditions may be selected depending on the kind of the second elongation primer, the kind of the elongated intermediate product and/or the kind of the DNA polymerase based on common knowledge of those skilled in the art. The reaction temperature of the second elongation reaction is, for example, from about 10 to 80° C. The second elongation reaction can be performed by keeping the reaction temperature at a constant level, keeping a plurality of temperature zones for a certain period of time, or repeating the temperature zones in a plurality of cycles. When the second elongation primer contains the LNA and/or PNA, the reaction temperature of the second elongation reaction is preferably from 20 to 90° C.

For example, the reaction temperature is kept as described above, whereby, for example, an elongated product is obtained in the step illustrated in FIG. 2B.

The above-described first and second elongation reactions can be performed in a reaction solution serving both as the first elongation reaction solution and as the second elongation reaction solution. In other words, for example, before performing the first elongation reaction, a component necessary for the second elongation reaction may be previously contained in the first elongation reaction solution. Or, after the first elongation reaction, a component necessary for the second elongation reaction is added to the reaction solution and used for the next reaction. Alternatively, after the first elongation reaction, the whole or part of the reaction solution is added to the solution containing a component necessary for the second elongation reaction, and the resulting mixture may be used as the second elongation reaction solution. For example, the first elongation primer and the second elongation primer may be previously contained in the first elongation reaction solution. Or the steps (S1) and (S2) are performed using the first elongation reaction solution not containing the second elongation primer, and the second elongation primer may be contained in the reaction solution before the step (S3).

According to the short-chain nucleic acid elongation method, the short-chain nucleic acid can be elongated more specifically and efficiently.

According to another embodiment, there is provided a method of elongating a plurality of kinds of the target short-chain nucleic acids having different base sequences in a sample. In that case, the first to n-th short-chain nucleic acid elongation primer sets are used. The first to n-th short-chain nucleic acid elongation primer sets respectively include the $1_1$-th to $1_n$-th elongation primers for elongating the $1_1$-th to $1_n$-th sequences respectively contained in the first to n-th target short-chain nucleic acids, and the $2_1$-th to $2_n$-th elongation primers. Here, n is an integer of 2 or more.

In this case, for example, the one sample is divided into n aliquots, the $1_1$-th to $1_n$-th elongation primers are respectively added to the aliquots to prepare the $1_1$-th to $1_n$-th reaction solutions, and after performing the first elongation reaction, the second elongation reaction may be performed using the $2_1$-th to $2_n$-th elongation primers in each of the reaction solutions. Or a first elongation reaction solution containing the sample and all the $1_1$-th to $1_n$-th elongation primers is prepared, the reaction solution is divided into n aliquots after performing the first elongation reaction, the $2_1$-th to $2_n$-th elongation primers are added to each of the reaction solutions to prepare the $2_1$-th to $2_n$-th reaction solutions, and the second elongation reaction may be performed. Alternatively, in a first elongation reaction solution containing the sample and the $1_1$-th to $1_n$-th elongation primers, the first elongation reaction is performed, and the second elongation reaction may be performed using the $2_1$-th to $2_n$-th elongation primers in the reaction solution without dividing the reaction solution. Although details will be described below, when the reaction solution is not divided in the above manner, the n kinds of the target sequences can be distinguished and detected by dividing the reaction solution into n aliquots in the subsequent step of amplifying the elongated product, or using an electrochemical detection device.

According to the short-chain nucleic acid elongation method, a plurality of kinds of the short-chain nucleic acids can be elongated more specifically and efficiently.

Short-Chain Nucleic Acid Detection Primer Set

Subsequently, the short-chain nucleic acid detection primer set including the short-chain nucleic acid elongation primer set and the LAMP primer set will be explained. The short-chain nucleic acid detection primer set is a primer set which elongates the target short-chain nucleic acid and amplifies the obtained elongated product.

The term "amplification" used herein means that the template nucleic acid is continuously replicated using the primer set and enzymes. The amplification method to be used in the embodiment is a loop-mediated isothermal amplification method (LAMP).

The short-chain nucleic acid detection primer set includes the short-chain nucleic acid elongation primer set and the LAMP primer set. The short-chain nucleic acid elongation primer set is any of the above-described short-chain nucleic acid elongation primer sets, and includes the first and second elongation primers. The LAMP primer set includes a FIP primer, a BIP primer, and a loop primer.

FIGS. 7A to 9B illustrate examples of association of the short-chain nucleic acid detection primer set with the elongated product.

FIG. 7A illustrates an example in which the fifth sequence of the elongated product (ii) is the loop primer sequence. The short-chain nucleic acid elongation primer set is the short-chain nucleic acid elongation primer set of FIG. 1. The LAMP primer set includes a FIP primer (v), a BIP primer (vi), and a loop primer (vii). The FIP primer (v) contains complementary sequences of the second and third sequences in this order in the 3' to 5' direction. The BIP primer (vi) contains the complementary sequence of the sixth sequence and the fourth sequence in this order in the 3' to 5' direction. The loop primer (vii) contains the fifth sequence.

Figure 7B:
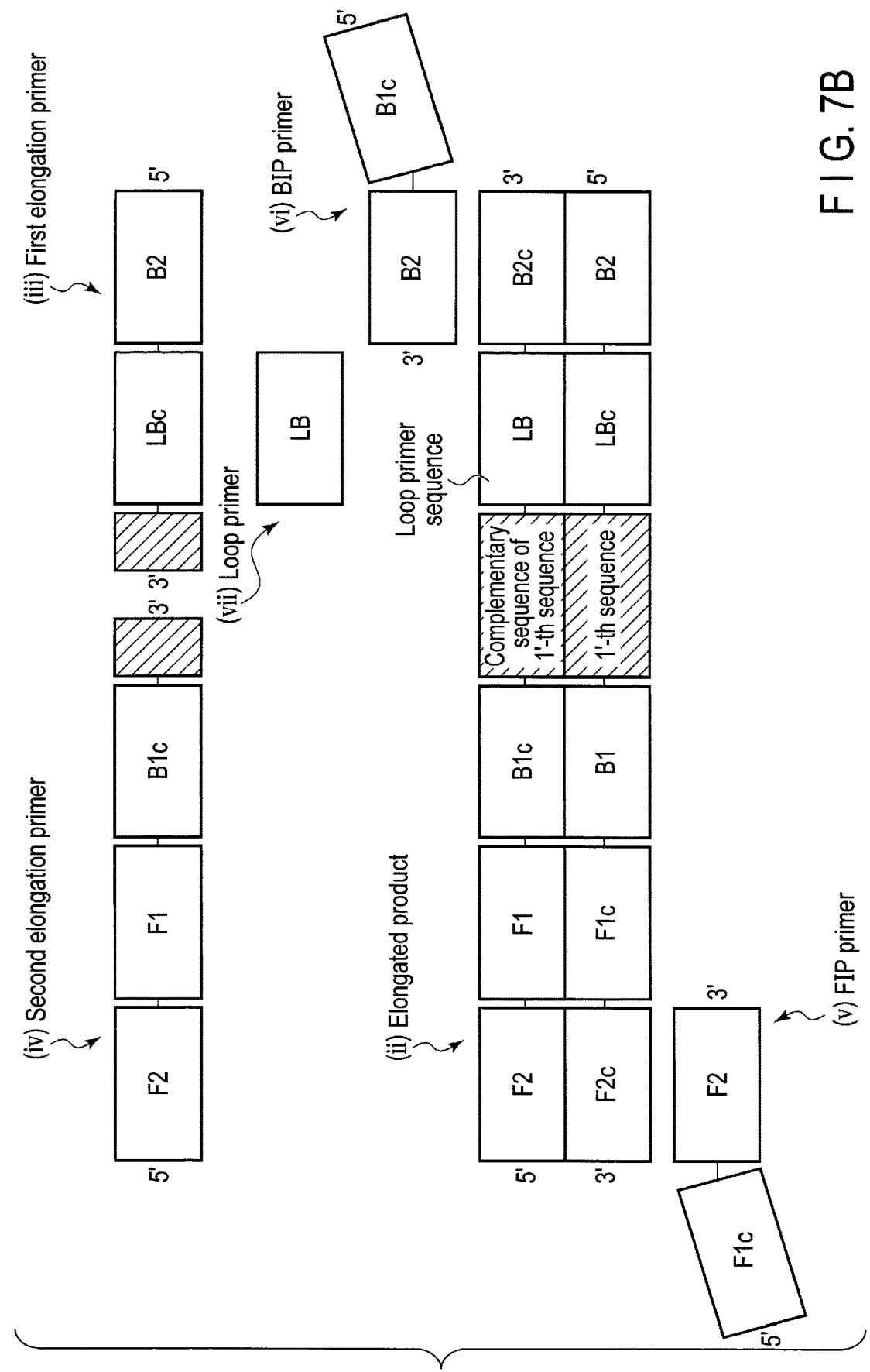
FIG. 7B is a pattern diagram illustrating an example of each of an elongated product and a short-chain nucleic acid detection primer set of the first embodiment.

For example, as the short-chain nucleic acid elongation primer in this example, the short-chain nucleic acid elongation primer set illustrated in FIG. 3 can be used. FIG. 7B illustrates an example of the short-chain nucleic acid detection primer set in that case. In this example, the LAMP primer set includes the FIP primer containing the F2 and F1c sequences in this order in the 3' to 5' direction, the BIP primer containing the B2 and B1c sequences in this order in the 3' to 5' direction, and the loop primer containing the LB sequence.

According to the short-chain nucleic acid detection primer set, the target short-chain nucleic acid can be elongated more specifically and efficiently, and the obtained elongated product can be rapidly and stably amplified.

Figure 8A:
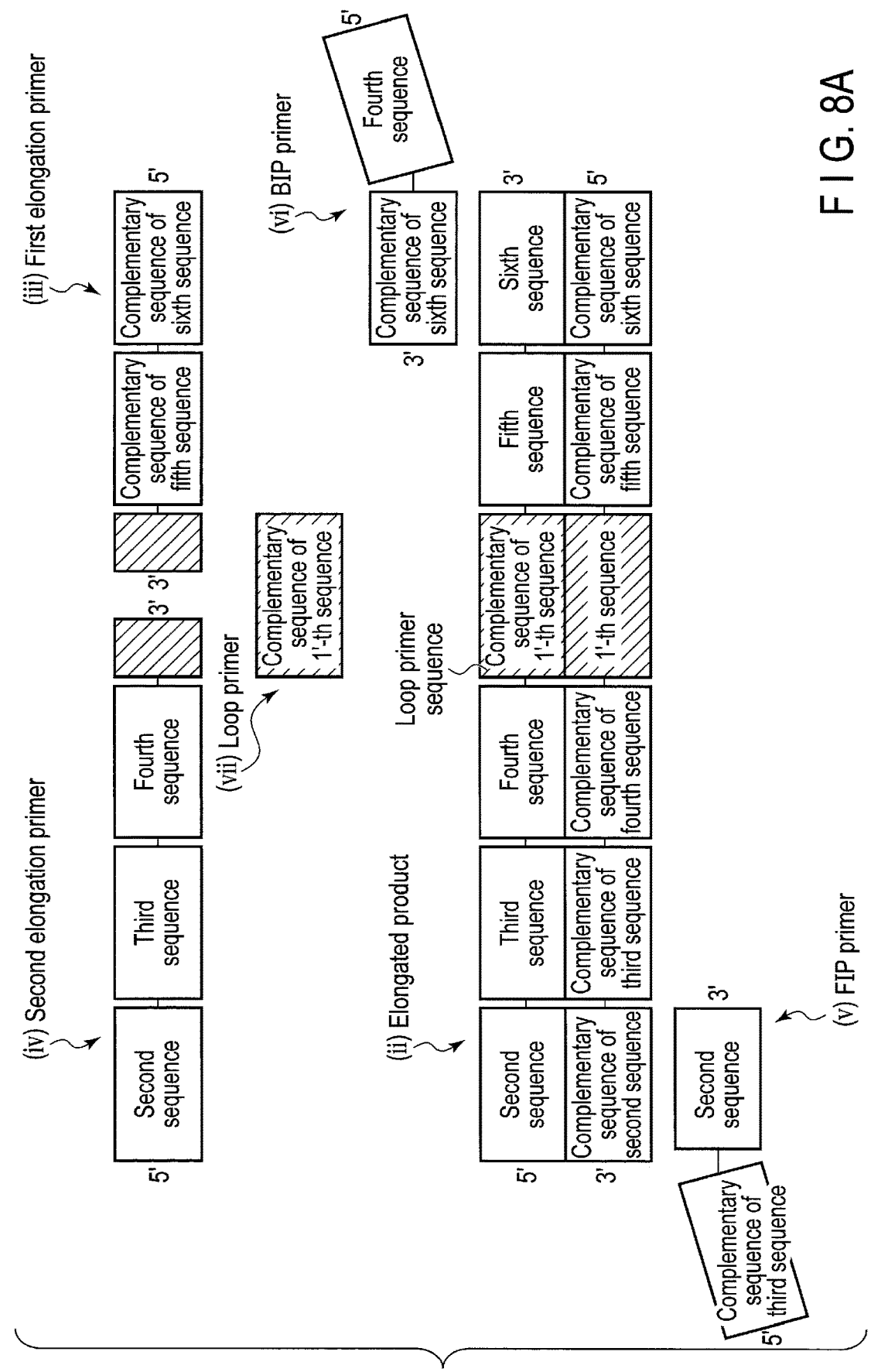
FIG. 8A is a pattern diagram illustrating an example of each of an elongated product and a short-chain nucleic acid detection primer set of the first embodiment.

FIG. 8A illustrates an example in which the complementary sequence of the 1'-th sequence of the elongated product (ii) is the loop primer sequence. In this example, the FIP primer (v) contains the second sequences and complementary sequences of the third sequences in this order in the 3' to 5' direction. The BIP primer (vi) contains the complementary sequence of the sixth sequence and the fourth sequence in this order in the 3' to 5' direction. The loop primer (vii) contains a complementary sequence of the 1'-th sequence.

For example, as the short-chain nucleic acid elongation primer in this example, the short-chain nucleic acid elongation primer set illustrated in FIG. 4 can be used. FIG. 8B illustrates an example of the short-chain nucleic acid detection primer set in that case. In this example, the LAMP primer set includes the FIP primer containing the F2 and F1c sequences in this order in the 3' to 5' direction, the BIP primer containing the B2 and B1c sequences in this order in the 3' to 5' direction, and the loop primer containing the complementary sequence of the 1'-th sequence.

According to the short-chain nucleic acid detection primer set, the target short-chain nucleic acid can be elongated more specifically and efficiently, and the obtained elongated product can be rapidly and stably amplified. Further, the use of the short-chain nucleic acid detection primer set results in the following condition: when a desired elongated product containing the 1'-th sequence and the complementary sequence thereof is produced, the loop primer hybridizes with the 1'-th sequence and the amplification product is stably obtained and the nonspecific elongated product is hardly amplified. Therefore, it is possible to more specifically amplify the short-chain nucleic acid.

Figure 9A:
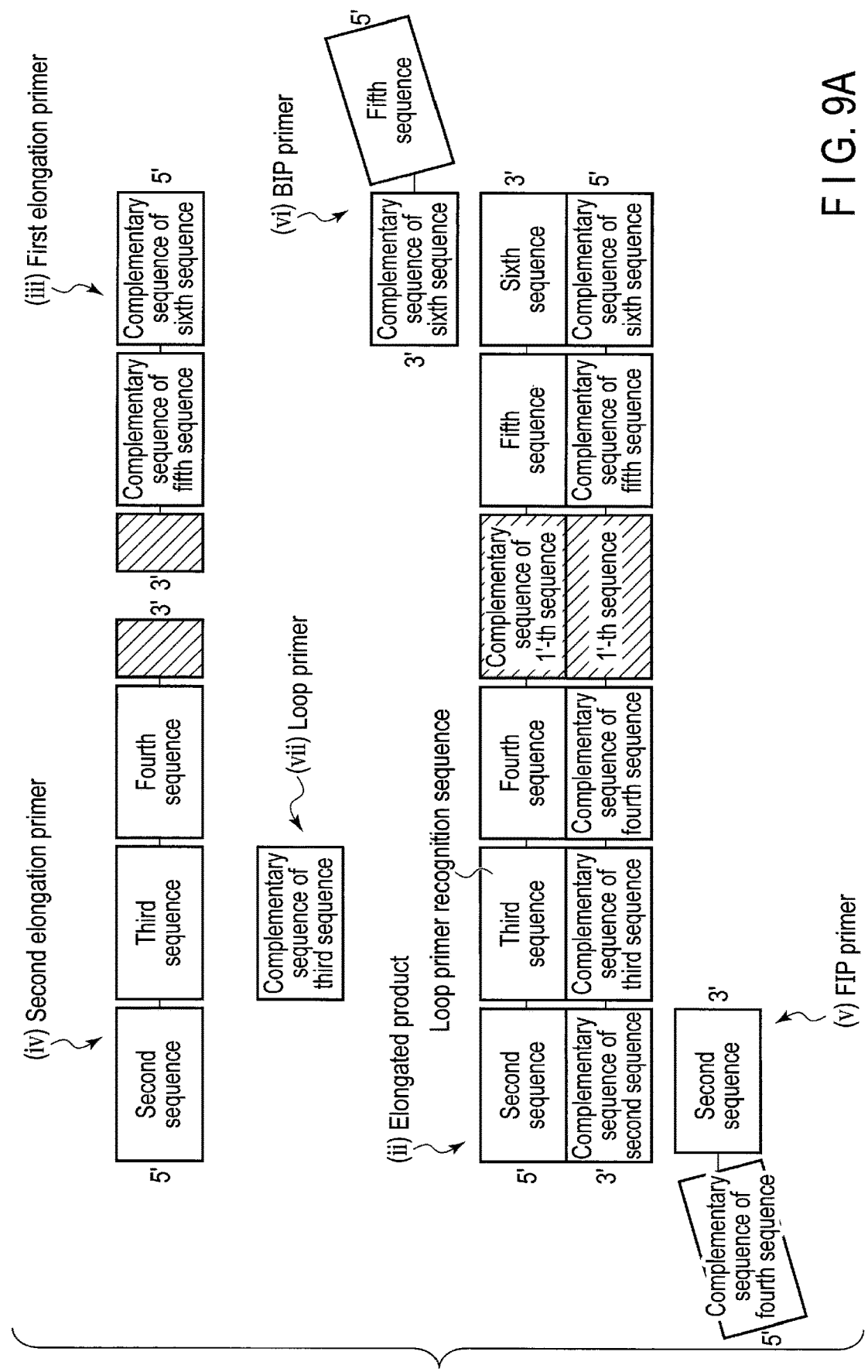
FIG. 9A is a pattern diagram illustrating an example of each of an elongated product and a short-chain nucleic acid detection primer set of the first embodiment.

FIG. 9A illustrates an example in which the third sequence of the elongated product (ii) is the loop primer recognition sequence. In this example, the FIP primer (v) contains complementary sequences of the second and fourth sequences in this order in the 3' to 5' direction. The BIP primer (vi) contains the complementary sequence of the sixth sequence and the fifth sequence in this order in the 3' to 5' direction. The loop primer (vii) contains a complementary sequence of the third sequence.

Figure 9B:
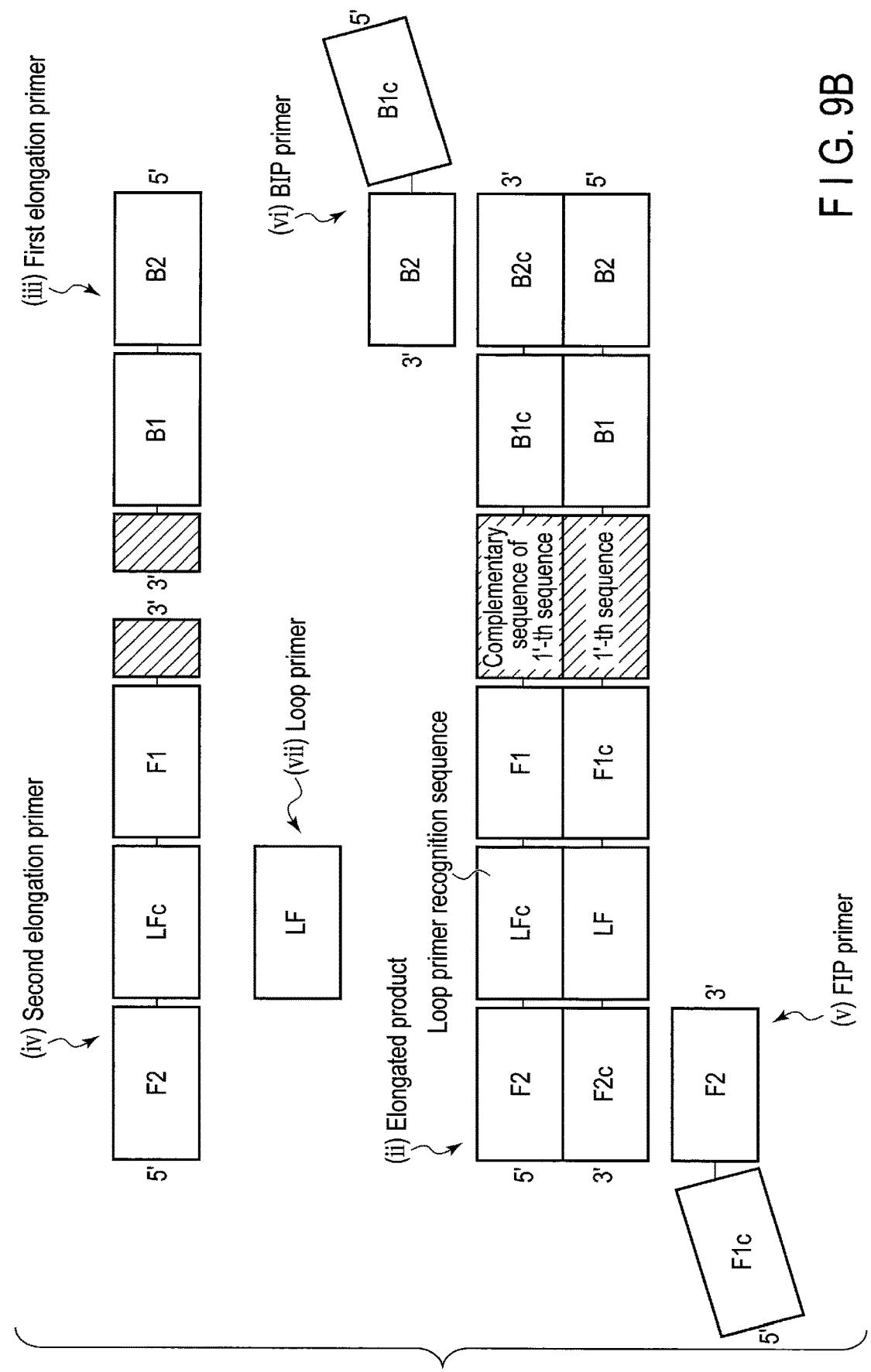
FIG. 9B is a pattern diagram illustrating an example of each of an elongated product and a short-chain nucleic acid detection primer set of the first embodiment.

For example, as the short-chain nucleic acid elongation primer in this example, the short-chain nucleic acid elongation primer set illustrated in FIG. 5 can be used. FIG. 9B illustrates an example of the short-chain nucleic acid detection primer set in that case. In this example, the LAMP primer set includes the FIP primer containing the F2 and F1c sequences in this order in the 3' to 5' direction, the BIP primer containing the B2 and B1c sequences in this order in the 3' to 5' direction, and the loop primer containing the LE sequence.

According to the short-chain nucleic acid detection primer set, the target short-chain nucleic acid can be elongated more specifically and efficiently, and the obtained elongated product can be rapidly and stably amplified.

Short Chain Nucleic Acid Amplification Method

Hereinafter, the method of amplifying a target short-chain nucleic acid using the above-described short-chain nucleic acid detection primer set will be explained.

FIG. 10 is a schematic flow illustrating an example of a short-chain nucleic acid amplification method of an embodiment. The method is a method of amplifying a target short-chain nucleic acid containing a first sequence in a sample and includes the following steps (S11) to (S14):

hybridizing the first elongation primer with the first sequence and elongating the first sequence to obtain an elongated intermediate product containing the 1'-th sequence (S11);

dissociating the elongated intermediate product from the target short-chain nucleic acid (S12);

hybridizing the second elongation primer with the 1'-th sequence of the elongated intermediate product and elongating the second elongation primer and the elongated intermediate product to obtain an elongated product (S13);

and maintaining an amplification reaction solution containing the elongated product, the LAMP primer set, and a strand displacement DNA polymerase under isothermal amplification reaction conditions, thereby amplifying the 1'-th sequence and/or the complementary sequence thereof using the elongated product as a template to obtain an amplification product (S14).

First, the steps (S11) to (S13) are executed. The steps (S11) to (S13) can be respectively performed by, for example, the same methods as those of the steps (S1) to (S3) of the above-described short-chain nucleic acid elongation method.

In the step (S14), an amplification reaction solution containing the elongated product obtained in the step (S13), the LAMP primer set, and a strand displacement DNA polymerase is maintained under isothermal amplification reaction conditions.

The LAMP primer set is any of the above-described primer sets for LAMP.

The strand displacement DNA polymerase is an enzyme for catalyzing an isothermal amplification reaction which amplifies the 1'-th sequence and the complementary sequence thereof using the elongated product be a template. Although the strand displacement DNA polymerase is not particularly limited, and examples thereof may include Bst, Bst2.0, Bst3.0, GspSSD, GspM, Tin, Bsm, Csa, 96-7, phi29, OmniAmp (registered trademark), Aac, BcaBEST (registered trademark), DisplaceAce (registered trademark), SD, StrandDisplace (registered trademark), TOPOTAQ, Isotherm2G, Taq, and a combination thereof.

The amplification reaction solution may further contain a desired component necessary for the amplification reaction, in addition to those components. The component may be, for example, a substrate such as deoxynucleoside triphosphate (dNTPs) or a salt compound for maintaining an appropriate amplification environment.

The isothermal amplification reaction conditions may be selected depending on the LAMP primer set and the kind of the strand displacement DNA polymerase based on common knowledge of those skilled in the art. The isothermal amplification reaction conditions include the followings: temperature: 50 to 75° C.; and time: 30 to 90 minutes, wherein the temperature is preferably from 60 to 70° C.

The amplification reaction solution is maintained under isothermal amplification reaction conditions, thereby amplifying the 1'-th sequence and/or the complementary sequence thereof using the elongated product as a template to obtain an amplification product containing the 1'-th sequence and/or the complementary sequence thereof.

According to the above-described short-chain nucleic acid amplification method, the target short-chain nucleic acid in the sample can be elongated more specifically and efficiently, and the obtained elongated product can be rapidly and stably amplified. Further, the short-chain nucleic acid detection primer sets illustrated in FIGS. 8A and 8B are used, whereby the target short-chain nucleic acid can be further specifically amplified.

In another embodiment, the second DNA polymerase used in the steps (S3) and (S13) may be a strand displacement DNA polymerase. In that case, the second DNA polymerase used in the steps (S3) and (S13) may be used as the strand displacement DNA polymerase in the step (S14). In that case, for example, after the completion of the second elongation reaction, the step (S14) may be performed without adding the strand displacement DNA polymerase to the amplification reaction solution. In that case, it is possible to reduce the amount of the enzyme to be used and cut costs. Further, it is possible to make the experimental procedure simpler.

The above-described first elongation reaction, second elongation reaction, and amplification reaction can be performed in a reaction solution which serves as the first elongation reaction solution, the second elongation reaction solution, and the amplification reaction solution. In other words, for example, before performing the first elongation reaction, components necessary for the second elongation reaction and the amplification reaction may be previously contained in the first elongation reaction solution. Alternatively, after each of the reactions, a component necessary for the next reaction is added to the reaction solution, and the resulting mixture may be used for the next reaction. Alternatively, after the each reaction, the whole or part of the reaction solution may be added to the solution containing a component necessary for the next reaction. In that case, the operation is simpler because it is not necessary to perform the following steps of: removing the nonspecific products produced by the first elongation reaction and the second elongation reaction; separating the elongated intermediate product from the second elongation reaction; and separating the elongated product for the amplification reaction. This is achieved by using the short-chain nucleic acid elongation primer set of the embodiment which can elongate the target short-chain nucleic acid specifically.

Short-Chain Nucleic Acid Detection Method

In another embodiment, there is provided a target short-chain nucleic acid detection method.

Figure 11:
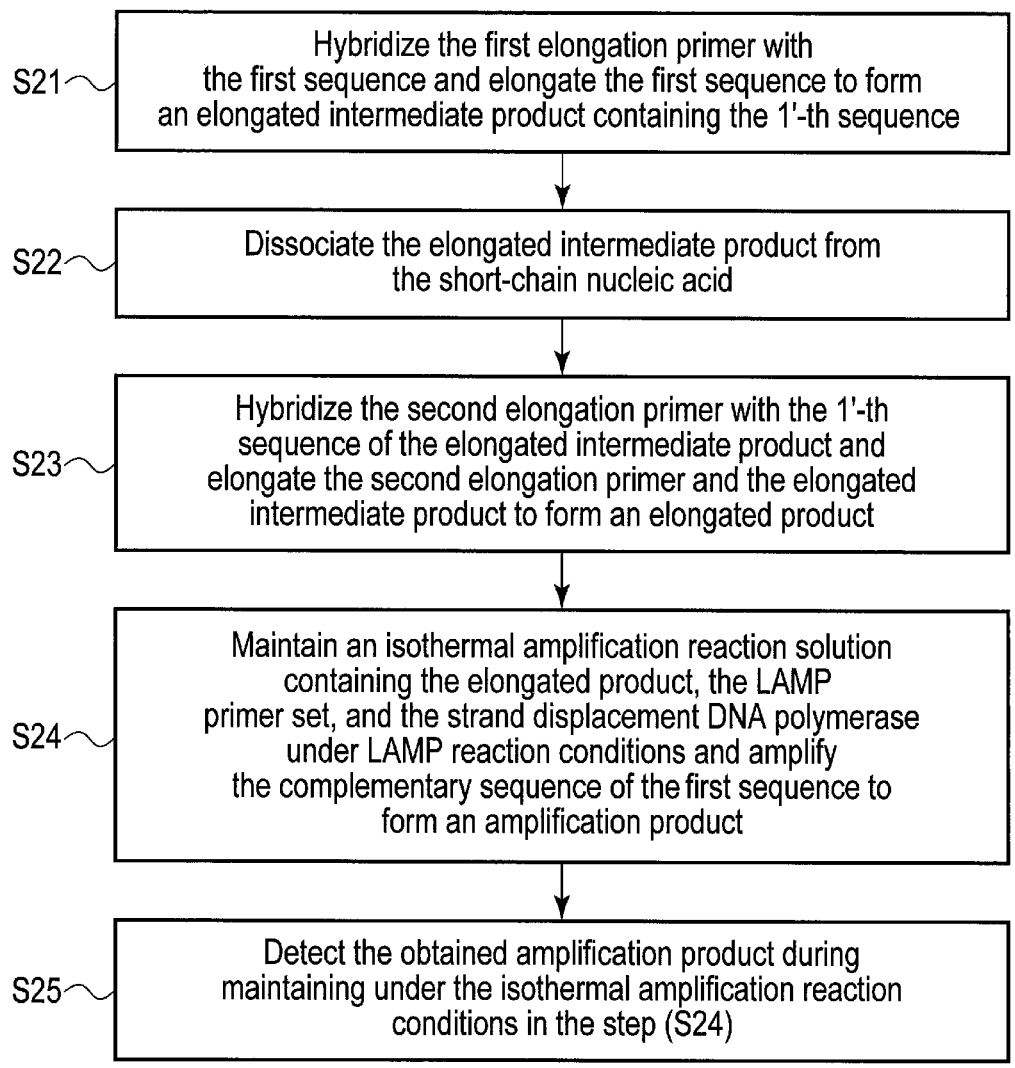
FIG. 11 is a flow chart illustrating an example of a short-chain nucleic acid amplification method of the first embodiment.

FIG. 11 is a schematic flow illustrating an example of a short-chain nucleic acid detection method of an embodiment. The method is a method of detecting a target short-chain nucleic acid containing a first sequence in a sample and includes the following steps (S21) to (S25):

hybridizing the first elongation primer with the first sequence and elongating the first sequence to obtain an elongated intermediate product containing the 1'-th sequence (S21);

dissociating the elongated intermediate product from the target short-chain nucleic acid (S22);

hybridizing the second elongation primer with the 1'-th sequence of the elongated intermediate product and elongating the second elongation primer and the elongated intermediate product to obtain an elongated product (S23);

maintaining an amplification reaction solution containing the elongated product, the LAMP primer set, and a strand displacement DNA polymerase under isothermal amplification reaction conditions, thereby amplifying the 1'-th sequence and/or the complementary sequence thereof using the elongated product as a template to obtain an amplification product (S24); and detecting the obtained amplification product during maintaining under the amplification reaction conditions of the step (S24) (S25).

The steps (S21) to (S24) can be respectively performed by, for example, the same methods as those of the steps (S11) to (S14) as described above.

In the step (S25), the obtained amplification product is detected during maintaining under amplification reaction conditions. The amplification product can be detected using turbidity, an optical signal or an electrochemical signal as an indicator.

When the amplification product is detected using turbidity as the indicator, the turbidity of the reaction solution may be detected. The turbid of the reaction solution is caused by, for example, magnesium pyrophosphate which is produced depending on the amplification product or the presence of the amplification reaction. Therefore, for example, the higher the abundance of the amplification product, the higher the turbidity. The detecting can be performed, for example, using a turbidimeter or an absorption spectrometer or visual observation.

When the amplification product is detected using an optical signal as an indicator, a marker substance which produces an optical signal (e.g., a fluorescence reagent containing calcein or an intercalator) can be used. Wherein the optical signal changes depending on the presence of the amplification product or the amplification reaction. The marker substance is previously contained in the amplification reaction solution and the optical signal from the marker substance may be detected during maintaining under the amplification reaction conditions. The detecting can be performed, for example, using any of known photo sensors or visual observation.

When the amplification product is detected using an electrochemical signal as an indicator, for example, a marker substance which generates an electrochemical signal from an oxidation-reduction reaction or the like can be used. Wherein the electrochemical signal changes depending on an increase in the amplification product. The marker substance is previously contained in the amplification reaction solution, and the electrochemical signal from the marker substance may be detected during maintaining under the amplification reaction conditions. The detecting can be performed, for example, using the electrochemical detection device including an electrode for detecting the electrochemical signal to be described below.

The electrochemical signal generating marker substance is, for example, an oxidizing agent whose oxidation reduction potential can serve as an electrochemical signal. Examples of the electrochemical signal generating marker substance include ferricyanide ions, ferrocyanide ions, iron complex ions, ruthenium complex ions, and cobalt complex ions. Each of these marker substances is obtained by dissolving potassium ferricyanide, potassium ferrocyanide, an iron complex, a ruthenium complex or a cobalt complex in a reaction solution.

For example, when ferricyanide ion ($Fe(CN)_6^{4-}$) is used as the marker substance, electrons are released by an oxidation reaction in which $Fe(CN)_6^{4-}$ is converted to $Fe(CN)_6^{3-}$. Each of these marker substances is rebound to an amplification product having a negative charge and is away from the amplification product. Thus, in the electrode in which the amplification products are present in the vicinity, a current (electrochemical signal) to be detected with an increase in the amplification product decreases.

Alternatively, the electrochemical signal generating marker substance may be a redox probe. The redox probe is, for example, a substance having an oxidation reduction potential of from −0.5 V to 0.5 V, and electrostatically binds to an amplification product in a reaction solution. The redox probe bound to the amplification product is oxidized or reduced by applying a voltage to the electrode, and the reaction results in release of electrons. Accordingly, for example, in the electrode in which the amplification products are present in the vicinity, the current (electrochemical signal) to be detected with an increase in the amplification product increases or a peak potential of oxidation-reduction to be detected shifts to a negative direction. Therefore, in addition to the electrochemical signal, the peak potential of oxidation-reduction is detected, whereby the measurement can be performed with high accuracy.

The redox probe is, for example, a metal complex. Regarding the metal complex used as the redox probe, a central metal is, for example, ruthenium (Ru), rhodium (Rh), platinum (Pt), cobalt (Co), chromium (Cr), cadmium (Cd), nickel (Ni), zinc (Zn), copper (Cu), osmium (Os), iron (Fe) or silver (Ag). The metal complex is, for example, an amine complex, a cyano complex, a halogen complex, a hydroxy complex, a cyclopentadienyl complex, a phenanthroline complex or a bipyridine complex. Further, redox probes such as methylene blue, Nile blue, and crystal violet can be used.

For example, the electrochemical signal generating marker substance is ruthenium hexane amine (RuHex). In that case, when the amplification product is present, $RuHex^{3+}$ bound to the amplification product is reduced to $RuHex^{2+}$ by applying a voltage to the electrode and electrons are released. The electrons flow into the electrode, whereby the amplification product can be detected.

The electrochemical detection device includes a chip. The chip includes a substrate having at least one electrode on one surface. The electrode can be obtained by, for example, forming a metallic pattern having a desired shape, such as a circular shape or a square shape on a substrate. It is preferable that the metal is, for example, gold because the sensitivity thereof is favorable. When the amplification reaction solution is brought onto the one surface, the electrode comes into contact with the amplification reaction solution, thereby detecting the electrochemical signal from the marker substance in the amplification reaction solution. The substrate may further include a pad. The pad is electrically connected to the electrode, and information on the electrochemical signal obtained from the electrode can be retrieved from the pad. Further, the substrate may include a reference electrode and a counter electrode.

The electrochemical detection device may include a measurement unit that receives a detection signal from the electrode of the chip, a control unit that controls the measuring unit, generates measurement data from the detected signal, and stores the measurement data in a memory, a quantification unit that quantifies the target short-chain nucleic acid in the sample based on the measurement data, a liquid-feed unit that feeds the amplification reaction solution to the chip and takes out it by control by the control unit, and/or a temperature control unit that controls the temperature of the chip by control by the control unit. These units may be computers.

The turbidity, optical signal, and electrochemical signal explained above may be detected within a specified time from the start of the amplification reaction or may be temporarily detected. The temporarily may mean continuously, or may mean to detect intermittently (i.e., at a desired time interval) at a plurality of points of time. In such detecting, as the abundance of the target short-chain nucleic acid present in the sample is higher, a rise of change of the signal is observed in a shorter time. For example, the target short-chain nucleic acid can be detected or quantified from the time to threshold in the following manner. A plurality of standard samples containing the short-chain nucleic acid at different known concentrations is used to create a calibration curve of the time to threshold of the detection signal relative to the abundance of the short-chain nucleic acid. Then, the calibration curve is compared to the measurement results of the time to threshold in the target short-chain nucleic acid. Based on this, the abundance of the target short-chain nucleic acid in the sample can be calculated.

In another embodiment of the short-chain nucleic acid detection method, the 1'-th sequence and the complementary sequence thereof are separated from other sequences by fragmenting the amplification product with a specific restriction enzyme, and the 1'-th sequence and the complementary sequence thereof may be detected. In that case, the first elongation primer, the second elongation primer, and a primer set which binds to the elongated product is designed so that the amplification product contains the sequence which can be cut with the specific restriction enzyme. In that case, after the amplification reaction, the amplification product is treated with the corresponding restriction enzyme. Then, for example, the amplification product is analyzed by electrophoresis. When the target short-chain nucleic acid is present in the sample, and the sequence containing the 1'-th sequence and the complementary sequence thereof, as a result of electrophoresis, amplification products appear as a band in a specific position. Based on this, the presence or absence of the target short-chain nucleic acid in the sample can be clearly determined.

According to the short-chain nucleic acid detection method of the above-described embodiment, the target short-chain nucleic acid in the sample is elongated more specifically and efficiently, and the obtained elongated product can be rapidly and stably amplified. Thus, the target short-chain nucleic acid can be detected accurately and specifically.

Further, when the target short-chain nucleic acid is, for example, a short-chain nucleic acid which is expressed or whose expression level increases or decreases in cells with a specific disease, it is possible to accurately and specifically determine whether the living body from which the sample is collected has the specific disease by detecting the target short-chain nucleic acid by the detection method of the embodiment. Examples of the specific disease include cancers such as breast cancer, colon cancer or lung cancer, and other diseases. For example, when the target short-chain nucleic acid is a short-chain nucleic acid which is expressed or whose expression level increases or decreases in a specific bacterium or virus, it is possible to accurately and specifically determine the presence of the specific bacteria or virus in the sample or to determine whether the living body from which the sample is collected is infected with a specific bacterium or virus by detecting the target short-chain nucleic acid by the detection method of the embodiment.

According to another embodiment, there is provided a method of detecting a plurality of kinds of the target short-chain nucleic acids having different base sequences contained in one kind of sample. In that case, the first to n-th primer sets for short-chain nucleic acid detection are used. The first to n-th short-chain nucleic acid detection primer sets respectively include the first to n-th short-chain nucleic acid elongation primer sets for elongating the $1_1$-th to $1_n$-sequences respectively contained in the first to n-th target short-chain nucleic acids; and the first to n-th LAMP primer sets for amplifying the first to n-th elongated products obtained using the first to n-th short-chain nucleic acid elongation primer sets. Here, n is an integer of 2 or more.

For example, when the n kinds of the reaction solutions containing the n kinds of the elongated products respectively are produced in the above-described short chain nucleic acid elongation method, in each of the reaction solutions, the first to n-th amplification products are obtained using the first to n-th LAMP primer sets and the abundance of each of amplification products is detected, whereby the n kinds of the target sequences can be distinguished and detected.

Alternatively, when one reaction solution containing the n kinds of the elongated products is produced in the above-described short chain nucleic acid elongation method, the n kind of the elongated products can be distinguished and detected, for example, using the electrochemical detection device. The electrochemical detection device includes a chip Including a substrate with at least n electrodes on one surface. The first to n-the LAMP primer sets are releasably immobilized on the one surface near each of the electrodes. To the reaction solution containing the n kinds of the elongated products, any of the above-described electrochemical signal producing marker substances is added. This reaction solution is brought onto the one surface of a substrate, and a reaction solution is maintained on isothermal amplification conditions, whereby, in each of the electrodes, the corresponding elongated product is amplified using the first to n-th LAMP primer sets. Therefore, the time to threshold of the electrochemical signal of each of the electrodes is measured, whereby the n kinds of the target short-chain nucleic acids can be detected and quantified.

According to the above method, a plurality of kinds of the target short-chain nucleic acids can be detected and quantified accurately and specifically.

Assay Kit

According to another embodiment, there is provided an assay kit for detecting the short-chain nucleic acid. The kit includes a short-chain nucleic acid detection primer set, a nucleic acid elongation reagent, and an LAMP reagent.

The short-chain nucleic acid detection primer set contained in the assay kit is any of the above-described short-chain nucleic acid detection primer sets. The short-chain nucleic acid elongation primer set included in the short-chain nucleic acid detection primer set and the LAMP primer set may be accommodated in the separate containers.

The nucleic acid elongation reagent contains the first DNA polymerase and the second DNA polymerase. The nucleic acid elongation reagent may further contain other components necessary for the above-described first and second elongation reactions, such as a salt, a substrate such as deoxynucleoside triphosphate (dNTPs), a thickener as a reaction reagent, a pH adjustment buffer, a surfactant, an ion for increasing the annealing specificity, and/or an ion serving as a cofactor of reverse transcriptase, in addition to those components.

The LAMP reagent contains any of the above-described strand displacement DNA polymerases. The LAMP reagent may contain other components necessary for the above-described isothermal amplification reaction, such as a substrate (e.g., deoxynucleoside triphosphate (dNTPs)) or a salt compound for maintaining an appropriate amplification environment.

The assay kit may further include a marker substance generating an electrical signal which changes with an increase in the amplification product, and an electrochemical detection device for detecting the electrical signal. As the marker substance and the electrochemical detection device, for example, the above-described marker substance and electrochemical detection device can be used.

According to another embodiment, the assay kit may be for detecting a plurality of kinds of the target short-chain nucleic acids having different base sequences. For example, when the assay kit is for detecting n-kinds of the target short-chain nucleic acids having different base sequences, the assay kit includes the first to n-th short-chain nucleic acid detection primer sets. The first to n-th short-chain nucleic acid detection primer sets include the first to n-th short-chain nucleic acid elongation primer sets respectively for elongating the $1_1$-th to $1_n$-sequences contained in the first to n-th target short-chain nucleic acids respectively; and the first to n-th LAMP primer sets. Here, n is a natural number.

In the above example, the first to n-th primer sets for short-chain nucleic acid elongation and the first to n-th primer sets for LAMP may be accommodated in separate containers.

The above assay kit may include a chip including a substrate with at least n electrodes on one surface and the above-described electrochemical detection device in which the first to n-th LAMP primer sets are freely immobilized on the one surface near each of the electrodes.

According to the assay kit, the target short-chain nucleic acid can be detected and quantified accurately and specifically.

Second Embodiment

In another embodiment, the first elongation primer may not necessarily contain the fifth sequence. FIGS. 12A to 13B each show an example of such a short chain nucleic acid elongation primer set, an elongation product produced with use thereof, and a LAMP primer set for amplifying an elongation product.

In the example of FIG. 12A, as to an elongation product (ii), one chain contains the second, third, and fourth sequences, the complementary sequence of the 1'-th sequence, and the sixth sequence in this order in the 5' to 3' direction. The other chain is a complementary sequence of the above-mentioned one chain and contains the complementary sequence of the second sequence, the complementary sequence of the third sequence, the complementary sequence of the fourth sequence, the 1'-th sequence and the complementary sequence of the sixth sequence in this order in the 3' to 5' direction. In this example, the complementary sequence of the 1'-th sequence is a loop primer sequence.

The short chain nucleic acid elongation primer set contains the first elongation primer (iii) and the second elongation primer (iv). The first elongation primer (iii) contains the first elongation primer sequence and the complementary sequence of the sixth sequence in this order in the 3' to 5' direction. The second elongation primer (iv) contains the second elongation primer sequence, the fourth sequence, the third sequence and the second sequence in this order in the 3' to 5' direction.

The LAMP primer set contains an FIP primer (v), a BIP primer (vi) and a loop primer (vii). The FIP primer (v) contains the second sequence and the complementary sequence of the third sequence in this order in the 3' to 5' direction. The BIP primer (vi) contains the complementary sequence of the sixth sequence and the fourth sequence in this order in the 3' to 5' direction. The loop primer (vii) contains the complementary sequence of the 1'-th sequence.

Here, as the second sequence, the third sequence, the fourth sequence, the complementary sequence of the 1'-th sequence and the sixth sequence, mentioned above, materials similar to those described in the first embodiment can be used. Moreover, as in the first embodiment, each primer and elongation product may also contain a sequence other than those set forth above, for example, a spacer sequence.

FIG. 12B shows an example in which each sequence in the example of FIG. 12A is a recognition sequence to which a LAMP primer may hybridize. In this example, the second sequence is an F2 sequence, the third sequence is an F1 sequence, the fourth sequence is a B1c sequence and the sixth sequence is a B2c sequence.

Therefore, as to the elongation product (ii), one chain contains the F2 sequence, the F1 sequence, the B1c sequence, the complementary sequence of the 1'-th sequence and the B2c sequence in this order in the 5' to 3' direction, whereas the other chain contains the F2c sequence, the F1c sequence, the B1 sequence, the 1'-th sequence and the B2 sequence in this order in the 3' to 5' direction. The first elongation primer (iii) contains the first elongation primer sequence and the B2 sequence in this order in the 3' to 5' direction. The second elongation primer (iv) contains the second elongation primer sequence, the B1c sequence, the F1 sequence and the F2 sequence in this order in the 3' to 5' direction.

The FIP primer (v) contains the F2 sequence and the F1c sequence in this order in the 3' to 5' direction. The BIP primer (vi) contains the B2 sequence and the B1c sequence in this order in the 3' to 5' direction. The loop primer (vii) contains the complementary sequence of the 1'-th sequence.

Figure 13A:
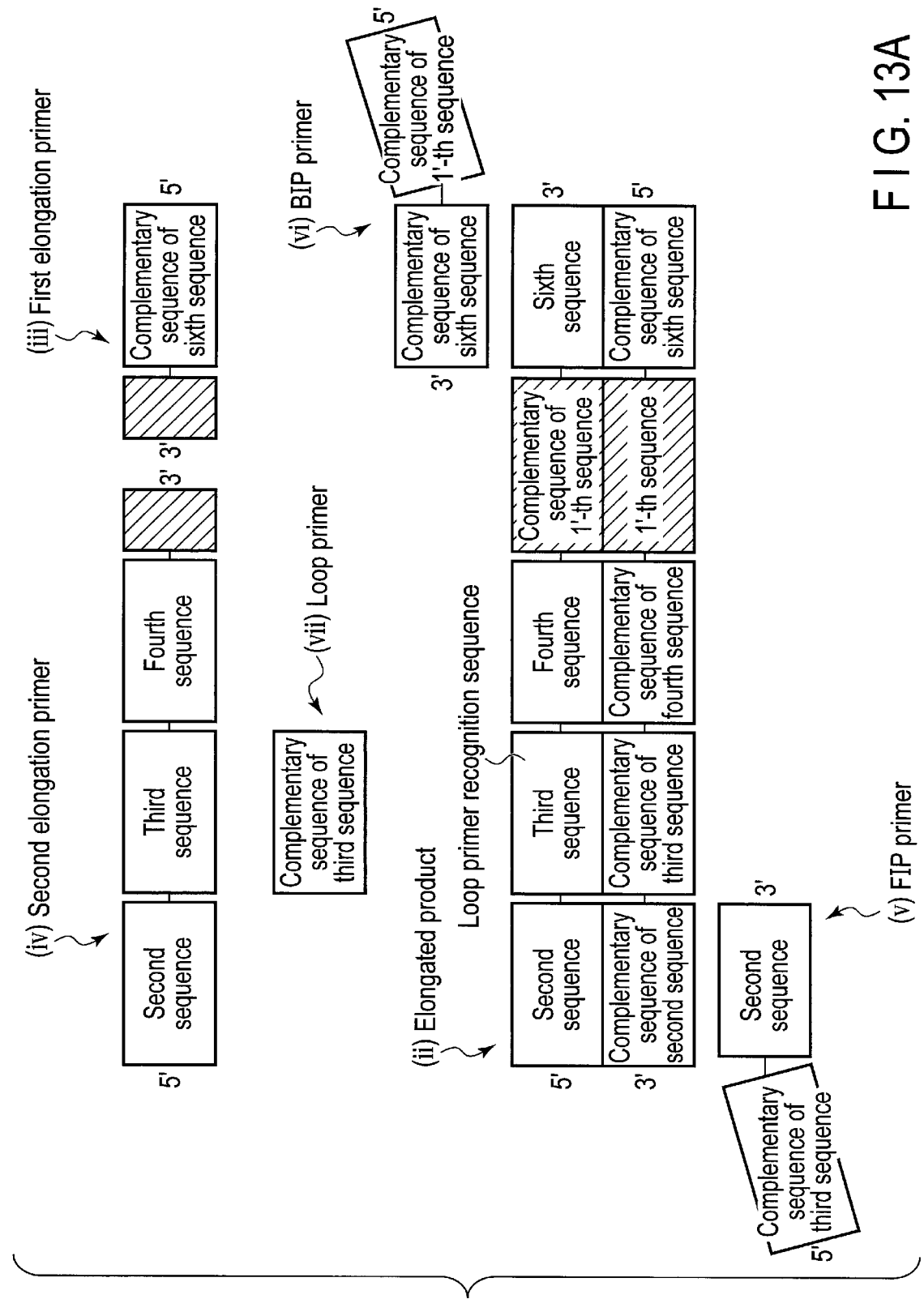
FIG. 13A is a pattern diagram illustrating an example of each of an elongated product and a short-chain nucleic acid detection primer set of the second embodiment.

FIG. 13A shows an example in which the sequences of the elongation product (ii), the first elongation primer (iii) and the second elongation primer (iv) are arranged in the same order as that of FIG. 12A, but the third sequence is a loop primer recognition sequence.

The FIP primer (v) contains the second sequence and the complementary sequence of the fourth sequence in this order in the 3' to 5' direction. The BIP primer (vi) contains the complementary sequence of the sixth sequence and the complementary sequence of the 1'-th sequence in this order in the 3' to 5' direction. The loop primer (vii) contains the complementary sequence of the third sequence.

Figure 13B:
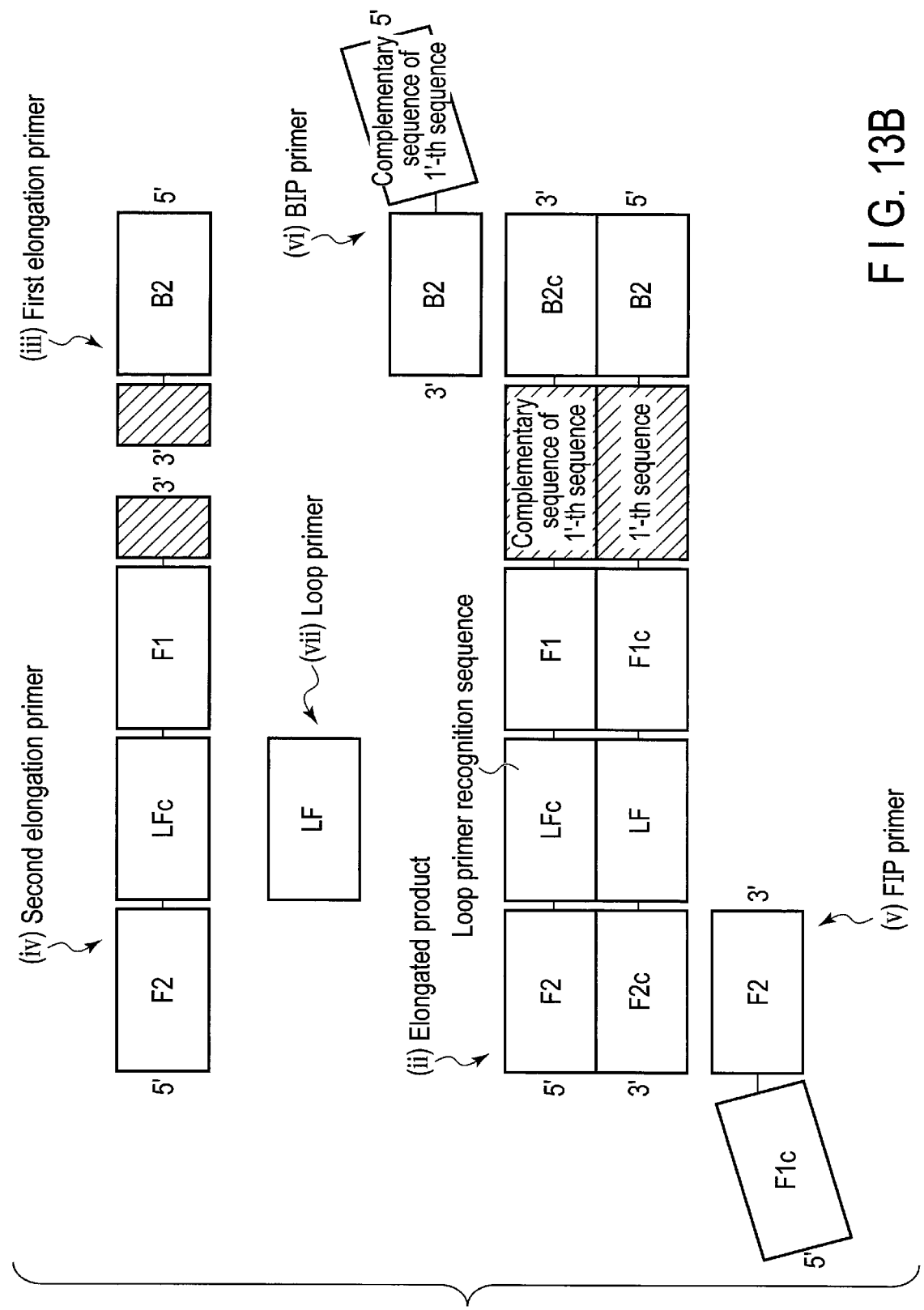
FIG. 13B is a pattern diagram illustrating an example of each of an elongated product and a short-chain nucleic acid detection primer set of the second embodiment.

FIG. 13B shows an example in which each sequence in the example of FIG. 13A set forth above is a recognition sequence to which a LAMP primer may hybridize. In this example, the second sequence is an F2 sequence, the third sequence is an LFc sequence, the fourth sequence is an F1 sequence and the sixth sequence is a B2c sequence.

Therefore, as to the elongation product (ii), one chain contains the F2, LFc, F1 sequences, the complementary sequence of the 1'-th sequence and the B2c sequence in this order in the 5' to 3' direction, whereas the other chain contains the F2c, LF, F1c, the 1'-th and B2 sequences in this order in the 3' to 5' direction. The first elongation primer (iii) contains the first elongation primer sequence and the B2 sequence in this order in the 3' to 5' direction. The second elongation primer (iv) contains the second elongation primer sequence, the F1, LFc and F2 sequences in this order in the 3' to 5' direction.

The FIP primer (v) contains the F2 sequence and the F1c sequence in this order in the 3' to 5' direction. The BIP primer (vi) contains the B2 sequence and the complementary sequence of the 1'-th sequence in this order in the 3' to 5' direction. The loop primer (vii) contains the LF sequence. In this example, the complementary sequence of the 1'-th sequence functions as a B1c sequence.

As described above, according to the second embodiment, a short chain nucleic acid elongation primer set which does not contain the fifth sequence and also a short chain nucleic acid detection primer set which contains the above-described LAMP primer set are provided. Further, an assay kit which contains a short chain nucleic acid detection primer set described in the first embodiment is also provided. Moreover, the short chain nucleic acid elongation primer set and the short chain nucleic acid detection primer set according to the second embodiment can be used similarly in the short chain nucleic acid elongation method, the short chain nucleic acid amplification method and the short chain nucleic acid detection method described in the first embodiment.

According to the second embodiment, the first elongation primer contains two sequences. Thus, the first elongation primer is shorter, and therefore when used for the short chain nucleic acid elongation method, it is possible to further prevent the first elongation primer and elongated intermediate product from being formed into a secondary structure. Moreover, the manufacturing cost of the first elongation primer can be further reduced.

In addition, the elongated product produced using the short chain nucleic acid elongation primer set of the second embodiment contains less primer recognition sequences in number than the conventional elongated product for the LAMP, but contains a loop primer sequence or a loop primer recognition region as in the case of the first embodiment. Therefore, with use of the short chain nucleic acid amplification method and the short chain nucleic acid detection method, it is possible to stably and quickly amplify the elongated product. In addition, even if the quantity of short chain nucleic acid is small, it can be amplified efficiently. Thus, with use of the short chain nucleic acid detection primer set of the second embodiment, it is possible to detect or quantify short chain nucleic acid more precisely.

The first and second elongation primers according to the second embodiment, if they have such a structure that the complementary sequence of the 1'-th sequence as shown in FIG. 12A or 12B is a loop primer recognition sequence, a loop primer may hybridize with the 1'-th sequence to produce an amplification product when an elongated product is produced. Therefore, the nonspecific elongated product is hardly amplified. Thus, it is possible to amplify short chain nucleic acid more specifically. Moreover, this structure is advantageous because the designing of both elongation primers is easier.

The first and second elongation primers according to the second embodiment, if they have such a structure that the complementary sequence of the 1'-th sequence as shown in FIG. 13A or 13B is a B1c sequence, a BIP primer may hybridize with the 1'-th sequence to produce an amplification product when an elongated product is produced. Therefore, the nonspecific elongated product is hardly amplified. Thus, it is possible to amplify short chain nucleic acid more specifically.

Third Embodiment

In a further embodiment, the second elongating primer may not necessarily contain the fourth sequence. FIGS. 14A to 15B each show an example of such a short chain nucleic acid elongation primer set, an elongation product produced with use thereof, and a LAMP primer set for amplifying an elongated product.

In the example of FIG. 14A, as to the elongated product (ii), one chain contains the second sequence, the third sequence, the complementary sequence of the 1'-th sequence, the fifth sequence and the sixth sequence in this order in the 5' to 3' direction. The other chain is the complementary sequence of the above-mentioned one chain and contains the complementary sequence of the second sequence, the complementary sequence of the third sequence, the 1'-th sequence, the complementary sequence of the fifth sequence and the complementary sequence of the sixth sequence in this order in the 3' to 5' direction. In this example, the fifth sequence is a loop primer sequence.

The first elongation primer (iii) contains the first elongation primer sequence, the complementary sequence of the fifth sequence and the complementary sequence of the sixth sequence in this order in the 3' to 5' direction. The second elongation primer (iv) contains the second elongation primer sequence, the third sequence and the second sequence in this order in the 3' to 5' direction.

The LAMP primer set contains an FIP primer (v), a BIP primer (vi) and a loop primer (vii). The FIP primer (v) contains the second sequence, the complementary sequence of the third sequence in this order in the 3' to 5' direction. The BIP primer (vi) contains the complementary sequence of the sixth sequence and the complementary sequence of the 1'-th sequence in this order in the 3' to 5' direction. The loop primer (vii) contains the fifth sequence.

Here, as the second sequence, the third sequence, the complementary sequence of the 1'-th sequence, the fifth sequence and the sixth sequence, mentioned above, materials similar to those described in the first embodiment can be used. Moreover, as in the first embodiment, each primer and elongation product may also contain a sequence other than those set forth above, for example, a spacer sequence.

FIG. 14B shows an example in which each sequence in the example of FIG. 14A set forth above is a recognition sequence to which a LAMP primer may hybridize. In this example, the second sequence is an F2 sequence, the third sequence is an F1 sequence, the fifth sequence is an LB sequence and the sixth sequence is a B2c sequence.

Therefore, as to the elongated product (ii), one chain contains the F2 sequence, the F1 sequence, the complementary sequence of the 1'-th sequence, the LB sequence and the B2c sequence in this order in the 5' to 3' direction, whereas the other chain contains the F2c sequence, the F1c sequence, the 1'-th sequence, the LBc sequence and the B2 sequence in this order in the 3' to 5' direction. The first elongation primer (iii) contains the first elongation primer sequence, the LBc sequence and the B2 sequence in this order in the 3' to 5' direction. The second elongation primer (iv) contains the second elongation primer sequence, the F1 sequence and the F2 sequence in this order in the 3' to 5' direction.

The FIP primer (v) contains the F2 sequence and the F1c sequence in this order in the 3' to 5' direction. The BIP primer (vi) contains the B2 sequence and the complementary sequence of the 1'-th sequence in this order in the 3' to 5' direction. The loop primer (vii) contains the fifth sequence. In this example, the complementary sequence of the 1'-th sequence functions as a B1c sequence.

FIG. 15A shows an example in which the sequences of the elongation product (ii), the first elongation primer (iii) and the second elongation primer (iv) are arranged in the same order as that of FIG. 14A, but the third sequence is a loop primer recognition sequence.

The FIP primer (v) contains the second sequence and the 1'-th sequence in this order in the 3' to 5' direction. The BIP primer (vi) contains the complementary sequence of the sixth sequence and the fifth sequence in this order in the 3' to 5' direction. The loop primer (vii) contains the complementary sequence of the third sequence.

FIG. 15B shows an example in which each sequence in the example of FIG. 15A set forth above is a recognition sequence to which a LAMP primer may hybridize. In this example, the second sequence is an F2 sequence, the third sequence is an LFc sequence, the fifth sequence is a B1c sequence and the sixth sequence is a B2c sequence.

Therefore, as to the elongated product (ii), one chain contains the F2 sequence, the LFc sequence, the complementary sequence of the 1'-th sequence, the B1c sequence and the B2c sequence in this order in the 5' to 3' direction, whereas and the other chain contains the F2c sequence, the LF sequence, the 1'-th sequence, the B1 sequence and the B2 sequence in this order in the 3' to 5' direction. The first elongation primer (iii) contains the first elongation primer sequence, the B1 sequence and the B2 sequence in this order in the 3' to 5' direction. The second elongation primer (iv) contains the second elongation primer sequence, the LFc sequence and the F2 sequence in this order in the 3' to 5' direction.

The FIP primer (v) contains the F2 sequence and the 1'-th sequence in this order in the 3' to 5' direction. The BIP primer (vi) contains the B2 sequence and the B1c sequence in this order in the 3' to 5' direction. The loop primer (vii) contains an LF sequence. In this example, the complementary sequence of the 1'-th sequence functions as an F1 sequence.

As described above, according to the third embodiment, a short chain nucleic acid elongation primer set which does not contain the fourth sequence and also a short chain nucleic acid detection primer set which contains the above-described LAMP primer set are provided. Further, an assay kit which contains a short chain nucleic acid detection primer set described in the first embodiment is also provided. Moreover, the short chain nucleic acid elongation primer set and the short chain nucleic acid detection primer set according to the second embodiment can be used similarly in the short chain nucleic acid elongation method, the short chain nucleic acid amplification method and the short chain nucleic acid detection method described in the first embodiment.

According to the third embodiment, the second elongation primer contains three sequences. Thus, the second elongation primer is shorter, and therefore when used for the short chain nucleic acid elongation method, it is possible to further prevent the first elongation primer and elongated intermediate product from being formed into a secondary structure. Moreover, the manufacturing cost of the second elongation primer can be further reduced.

In addition, the elongated product produced using the short chain nucleic acid elongation primer set of the third embodiment contains less primer recognition sequences in number than the conventional elongated product for the LAMP, but contains a loop primer sequence or a loop primer recognition region as in the case of the first embodiment. Therefore, with use of the short chain nucleic acid amplification method and the short chain nucleic acid detection method, it is possible to stably and quickly amplify the elongated product. In addition, even if the quantity of short chain nucleic acid is small, it can be amplified efficiently. Thus, with use of the short chain nucleic acid detection primer set of the third embodiment, it is possible to detect or quantify short chain nucleic acid more precisely.

The first and second elongation primers according to the third embodiment, if they have such a structure that the complementary sequence of the 1'-th sequence as shown in FIG. 14A or 14B is a B1c sequence, a BIP primer may hybridize with the 1'-th sequence to produce an amplification product when an elongated product is produced. Therefore, the nonspecific elongated product is hardly amplified. Thus, it is possible to amplify short chain nucleic acid more specifically.

The first and second elongation primers according to the third embodiment, if they have such a structure that the complementary sequence of the 1'-th sequence as shown in FIG. 15A or 15B is an F1 sequence, an FIP primer may hybridize with the complementary sequence of the 1'-th sequence to produce an amplification product when an elongated product is produced. Therefore, the nonspecific elongated product is hardly amplified. Thus, it is possible to amplify short chain nucleic acid more specifically.

EXAMPLES

Example 1

The example in which miRNA was elongated using the short-chain nucleic acid detection primer set of the embodiment, LAMP was performed, the presence of quantification and the specificity were evaluated will be shown hereinbelow.

Production of Short-Chain Nucleic Acid Detection Primer Set I (Example)

Figure 16:
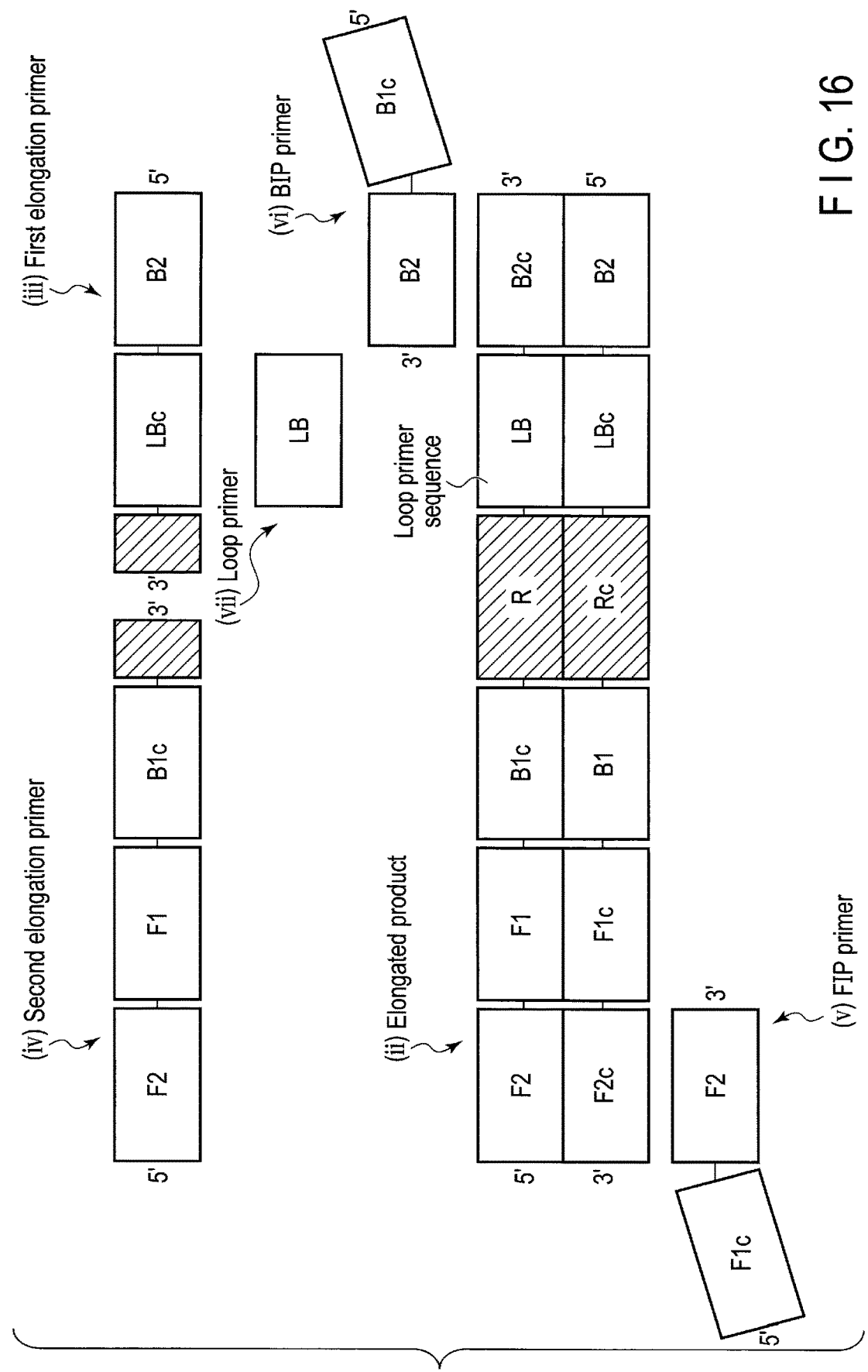
FIG. 16 is a pattern diagram of a short-chain nucleic acid detection primer set I used in Example 1.

A short-chain nucleic acid detection primer set I having a configuration illustrated in FIG. 16 for elongating and amplifying miRNA let7-a (Table 1, SEQ ID NO: 1) was produced. In the FIG. 12, "R" represents the corresponding DNA of miRNA let7-a (SEQ ID NO: 1), and "Rc" represents the complementary sequence thereof. The first elongation primer contains a first elongation primer sequence, an LBc sequence, and a B2 sequence. The second elongation primer contains a second elongation primer sequence, a B1c sequence, an F1 sequence, and an F2 sequence. In the elongated product obtained with this primer set, one chain contains the F2, F1, and B1c sequences, an R sequence, an LB sequence, and a B2c sequence. The FIP primer contains the F2 sequence and an F1c sequence, the BIP primer contains the B2 and B1c sequences, and the loop primer contains the LB sequence.

In the design of the short-chain nucleic acid detection primer set, the sequences of the FIP primer, the BIP primer, and the loop primer (LB primer) were determined to be SEQ ID NOS: 2, 3, and 4 illustrated in Table 1, respectively. Based on the sequences, the sequences of the first elongation primer (SEQ ID NO: 5) and the second elongation primer (SEQ ID NO: 6) were designed.

TABLE 1

| | Type of oligo/ type of primer | Sequence (5' to 3') | SEQ ID NO: |
|---|---|---|---|
| | miRNA let7-a | UGAGGUAGUAGGUUGUAUAGUU | 1 |
| Short-chain nucleic acid detection primer set I | FIP primer | GGCCTACTGTTTATGCTCGGCTCCGGACGACTGGATCCTT | 2 |
| | BIP primer | GATGGGGGAAGCATCTCGGGACTTGCTGACCTGAATGGTG | 3 |
| | LB primer | GGCTTGCAGTTAATTGCGTAC | 4 |
| | First elongation primer | ACTTGCTGACCTGAATGGTGTACGCAATTAACTGCAAGCCAACTATAC | 5 |
| | Second elongation primer | CCGGACGACTGGATCCTTAGCCGAGCATAAACAGTAGGCCGATGGGGGAAGCATCTCGGGGGGTGAGGTAGTAGGTTGT | 6 |
| | Elongated product (positive control) | CCGGACGACTGGATCCTTAGCCGAGCATAAACAGTAGGCCGATGGGGGAAGCATCTCGGGGGGTGAGGTAGTAGGTTGTATAGTTGGCTTGCAGTTAATTGCGTACACCATTCAGGTCAGCAAGT | 7 |

Elongation Reaction

A reaction solution (reaction volume: 20 µL) containing synthetic RNA let7-a having a copy number of 105, 104, 103, $10^2$ or 0, the first elongation primer with a final concentration of 5 nM (SEQ ID NO: 5), 67 U/20 µL of reverse transcriptase (MultiScribe™ Reverse Transcriptase), Tris-HCl with a final concentration of 20 mM (pH 8.0), 50 mM of KCl, 8 mM of $MgSO_4$, 10 mM of $(NH_4)_2SO_4$, 0.1% of Tween™-20 (non-ionic surfactant), 1.4 mM of dNTPs, 1 mM of DTT, and 4 U/20 µL of RNase OUT™ (RNase inhibitor) was used, and a reverse transcription reaction was performed under the following conditions: 16° C. for 30 minutes, 42° C. for 30 minutes, and 85° C. for 5 minutes.

Amplification Reaction

After the completion of the reaction, to the reaction solution, the second elongation primer with a final concentration of 4.4 5 nM (SEQ ID NO: 6) and 0.4 U of Deep-Vent™(exo-) DNA Polymerase (2 µL in total) were added, and the resulting mixture was subjected to elongation reaction at 35 cycles of 95° C. for 20 sec, 55° C. for 30 sec, 72° C. for 30 sec after 95° C. for 2 minutes. Thereafter, the elongation reaction was performed at 72° C. for 5 minutes.

1 µL of the obtained reaction solution was added to a solution containing the FIP primer (SEQ ID NO: 2) with a final concentration of 1.6 µM, 1.6 µM of the BIP primer (SEQ ID NO: 3), 0.8 µM of the LB primer (SEQ ID NO: 4), 8 U/25 µL of Tin exo-DNA polymerase, Tris-HCl (pH 8.0), 50 mM of KCl, 8 mM of $MgSO_4$, 10 mM of $(NH_4)_2SO_4$, 0.1% of Tween-20, 1.4 mM of dNTPs, and 24 µL of 0.8 M betaine mixture, and the resulting mixture was incubated at 65° C. for 90 minutes for LAMP. The amplifying was performed using the LAMP turbidity measuring system (LT-16, manufactured by NIPPON GENE, CO., LTD.) and the time to threshold of turbidity (hereinafter "Tt") was measured.

The amplification reaction was performed similarly to above using an amplification reaction solution obtained by adding $10^7$ copies of an artificially synthesized product (SEQ ID NO: 7) of an elongated product to be obtained by reverse transcription and elongation of miRNA using the first and second elongation primers as the positive control (hereinafter, "PC") to the above-described solution. To a negative control (hereinafter, "NC") to which no template was added, 1 µL of TE was added and the resulting mixture was treated similarly to above. The experiment was performed in duplicate.

Figure 17:
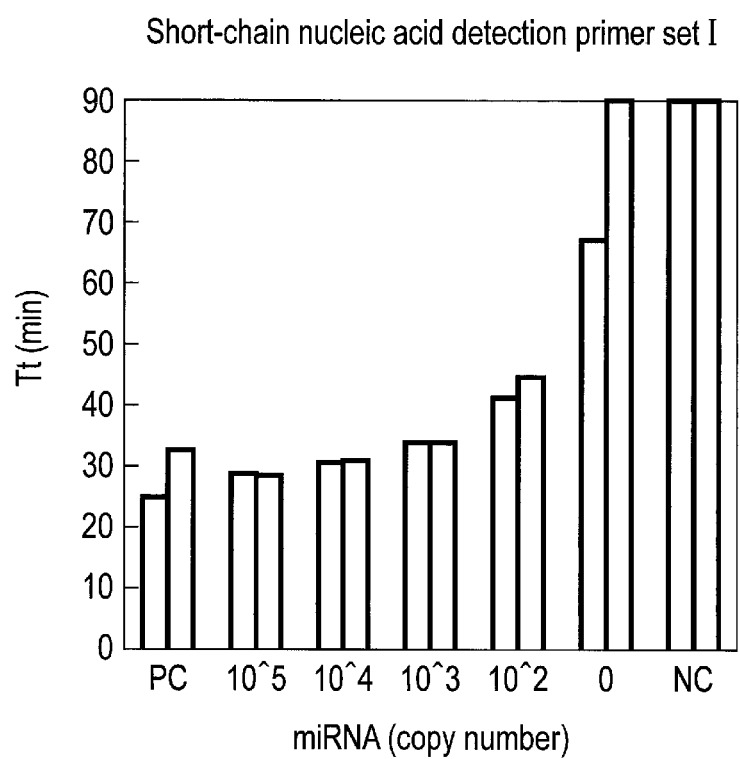
FIG. 17 is a graph showing experimental results in Example 1.

The results were shown in FIG. 17. In the case of $10^6$ to $10^2$ copies, there is a correlation between the abundance of miRNA and the Tt value. As the abundance of miRNA was lower, the Tt value was longer. Therefore, it is suggested that, according to the primer set of the embodiment, the elongated product is stably amplified and it is possible to quantify miRNA.

Further, with respect to the sample not containing miRNA ("0" in the figure), in one of the duplicate results, the turbidity rose in 67.3 minutes, and in the other, no amplification occurred. The former was assumed nonspecific amplification, and the Tt value was slower by 22 minutes than the Tt value in $10^2$ copies (41.2 minutes, 44.8 minutes, specific amplification). Therefore, it is apparent that, according to the primer set of the embodiment, there is an obvious difference between the specific amplification of $10^2$ copies and nonspecific amplification, and it is possible to quantify miRNA even if the abundance of miRNA is low ($10^2$ copies). Consequently, it is suggested that, according to the primer set and the method of the embodiment, it is possible to accurately detect miRNA compared to the conventional method.

Example 2

An example will be provided below, in which using primer sets with different configurations to obtain an elongated product containing six sequences, miRNA was elongated, LAMP was performed, and the presence of quantification and the specificity were compared.

Production of Short-Chain Nucleic Acid Detection Primer Set II (Example)

A short-chain nucleic acid detection primer set II for elongating and amplifying miRNA let7-a (Table 2, SEQ ID NO: 1) was prepared. The short-chain nucleic acid detection primer set II has the same configuration as that illustrated in FIG. 16, and the base sequences of the sequences are different from those of the short-chain nucleic acid detection primer set I and have the base sequences illustrated in Table 2. That is, the FIP primer has a base sequence of SEQ ID NO: 8, the BIP primer has a base sequence of SEQ ID NO: 9, the loop primer (LB primer) has a base sequence of SEQ ID NO: 10, the first elongation primer has a base sequence of SEQ ID NO: 11, and the second elongation primer has a base sequence of SEQ ID NO: 12.

TABLE 2

| | Type of oligo/ type of primer | Sequence (5' to 3') | SEQ ID NO: |
|---|---|---|---|
| | miRNA let7-a | UGAGGUAGUAGGUUGUAUAGUU | 1 |
| Short-chain nucleic acid detection primer set II | FIP primer | CGTCCAGCATATCAAAACCGCGCCTTCGGAGAACCCCTCT | 8 |
| | BIP primer | CGATTCACGATGCATCCGGCAGACGTTCTGGTACGAACTCG | 9 |
| | LB primer | CAACAGCAGCCGGGGAGTTG | 10 |
| | First elongation primer | GACGTTCTGGTACGAACTCGCAACTCCCCGGCTGCTGTTGAACTATAC | 11 |
| | Second elongation primer | CCTTCGGAGAACCCCTCTCGCGGTTTTGATATGCTGGACGCGATTCACGA TGCATCCGGCAGGGTGAGGTAGTAGGTTGT | 12 |
| | Elongated product (positive control) | CCTTCGGAGAACCCCTCTCGCGGTTTTGATATGCTGGACGCGATTCACGA TGCATCCGGCAGGGTGAGGTAGTAGGTTGTATAGTTCAACAGCAGCCGGG GAGTTGCGAGTTCGTACCAGAACGTC | 13 |

Production of Short-Chain Nucleic Acid Detection Primer Set III (Comparative Example)

A short-chain nucleic acid detection primer set III having a configuration illustrated in FIG. 14 for elongating and amplifying miRNA let7-a (Table 3, SEQ ID NO: 1) was prepared. The first elongation primer contains the first elongation primer sequence and the B2 sequence. The second elongation primer contains the second elongation primer sequence and the LB, B1c, F1, and F2 sequences. In the elongated product obtained with this primer set, one chain contains the F2, F1, B1c, LB, R, and B2c sequences. The FIP, BIP, and loop primers are the same as those of the short-chain nucleic acid detection primer set II.

Each of the primers of the short-chain nucleic acid detection primer set III has each base sequence illustrated in Table 3. That is, the FIP primer has a base sequence of SEQ ID NO: 8, the BIP primer has a base sequence of SEQ ID NO: 9, the loop primer (LB primer) has a base sequence of SEQ ID NO: 10, the first elongation primer has a base sequence of SEQ ID NO: 14, and the second elongation primer has a base sequence of SEQ ID NO: 15.

TABLE 3

| | Type of oligo/ type of primer | Sequence (5' to 3') | SEQ ID NO: |
|---|---|---|---|
| | miRNA let7-a | UGAGGUAGUAGGUUGUAUAGUU | 1 |
| Short-chain nucleic acid detection primer set III | FIP primer | CGTCCAGCATATCAAAACCGCGCCTTCGGAGAACCCCTCT | 8 |
| | BIP primer | CGATTCACGATGCATCCGGCAGACGTTCTGGTACGAACTCG | 9 |
| | LB primer | CAACAGCAGCCGGGGAGTTG | 10 |
| | First elongation primer | GACGTTCTGGTACGAACTCGAACTATAC | 14 |
| | Second elongation primer | CCTTCGGAGAACCCCTCTCGCGGTTTTGATATGCTGGACGCGATTCACGA TGCATCCGGCACAACAGCAGCCGGGGAGTTGGGGTGAGGTAGTAGGTTGT | 15 |
| | Elongated product (positive control) | CCTTCGGAGAACCCCTCTCGCGGTTTTGATATGCTGGACGCGATTCACGA TGCATCCGGCACAACAGCAGCCGGGGAGTTGGGGTGAGGTAGTAGGTTGT ATAGTTCGAGTTCGTACCAGAACGTC | 16 |

Elongation Reaction and Amplification Reaction

The elongation and amplification reactions were performed similarly to Example 1 using the short-chain nucleic acid detection primer sets II and III. As positive controls, artificially synthesized elongated products (SEQ ID NOS: 13 and 16, respectively) were used.

The results were shown in FIG. 19. With respect to the short-chain nucleic acid detection primer set II, despite the fact that in one of the duplicate results ($10^2$ copies), no amplification occurred, there was a correlation between the copy number of miRNA and the Tt value. Meanwhile, in the short-chain nucleic acid detection primer set III, the Tt value of all the samples (including the sample not containing miRNA) was approximately 40 minutes. Therefore, it is suggested that it is not possible to quantify miRNA using the short-chain nucleic acid detection primer set III. This result shows that even if the first elongation primer and the second elongation primer are configured to obtain an elongated product containing six sequences, it is not possible to quantify miRNA when the first elongation primer contains two sequences and the second elongation primer contains five sequences.

Example 3

The example shown hereinbelow is an example of in which using a primer set containing a dummy sequence, miRNA was elongated, LAMP was performed, and the presence of quantification and the specificity were evaluated.

Production of Short-Chain Nucleic Acid Detection Primer Set IV

A short-chain nucleic acid detection primer set IV for elongating and amplifying miRNA (miR-1307-3p) (Table 4, SEQ ID NO: 17) was prepared. The short-chain nucleic acid detection primer set IV has the same configuration as that illustrated in FIG. 16, and the base sequences of the sequences are different from those of the short-chain nucleic acid detection primer set I and have the base sequences illustrated in Table 4. That is, the FIP primer has a base sequence of SEQ ID NO: 18, the BIP primer has a base sequence of SEQ ID NO: 19, the loop primer (LB primer) has a base sequence of SEQ ID NO: 20, the first elongation primer has a base sequence of SEQ ID NO: 21, and the second elongation primer has a base sequence of SEQ ID NO: 22.

TABLE 4

| Type of oligo/ type of primer | | Sequence (5' to 3') | SEQ ID NO: |
|---|---|---|---|
| Short-chain nucleic acid detection primer set IV | miR-1307-3p | ACUCGGCGUGGCGUCGGUCGUG | 17 |
| | FIP primer | TGGAATACGTGAGACTGGGCCTAGGGTTGGAGGTTCATGTCA | 18 |
| | BIP primer | CTGACCACCAGTCGCACTGAGCCAGTCCGCCACTGTACT | 19 |
| | LB primer | AACACTGTCAGATAGGGCCTAG | 20 |
| | First elongation primer | CCAGTCCGCCACTGTACTCTAGGCCCTATCTGACAGTGTTCACGACCG | 21 |
| | Second elongation primer | AGGGTTGGAGGTTCATGTCAAGGCCCAGTCTCACGTATTCCACTGACCACC AGTCGCACTGAGGGGACTCGGCGTGGCGT | 22 |
| | Elongated product (positive control) | AGGGTTGGAGGTTCATGTCAAGGCCCAGTCTCACGTATTCCACTGACCACC AGTCGCACTGAGGGGACTCGGCGTGGCGTCGGTCGTGAACACTGTCAGATA GGGCCTAGAGTACAGTGGCGGACTGG | 23 |

Production of Short-Chain Nucleic Acid Detection Primer Set V

A short-chain nucleic acid detection primer set V having a configuration illustrated in FIG. 19 for elongating and amplifying miRNA (miR-1307-3p) (Table 5, SEQ ID NO: 17) was produced. The first elongation primer contains the first elongation primer sequence, the dummy sequence, and the B2 sequence. The second elongation primer contains a second elongation primer sequence, a B1c sequence, an F1 sequence, and an F2 sequence. In the elongated product obtained with this primer set, one chain contains the F2, F1, B1c, R, dummy, and B2c sequences. The FIP primer contains the F2 and F1c sequences, the BIP primer contains the B2 and B1c sequences, and the loop primer contains the R sequence.

Each of the primers of the short-chain nucleic acid detection primer set V has a base sequence illustrated in Table 5. That is, the FIP primer has a base sequence of SEQ ID NO: 18, the BIP primer has a base sequence of SEQ ID NO: 19, the loop primer has a base sequence of SEQ ID NO: 24, the first elongation primer has a base sequence of SEQ ID NO: 21, and the second elongation primer has a base sequence of SEQ ID NO: 22. The elongated product used as a positive control contains a base sequence of SEQ ID NO: 23.

miRNA and the Tt value and it is possible to quantify miRNA using those primer sets with high sensitivity. Further, in the short-chain nucleic acid detection primer set IV, the absolute value of the slope of an increase in the Tt value (in $10^6$ to $10^3$ copies) was 3.08, meanwhile, in the short-chain nucleic acid detection primer set V, the absolute value was 4.80. Therefore, it is apparent that it is possible to quantify miRNA accurately using the short-chain nucleic acid detection primer set IV. Further, in the short-chain nucleic acid detection primer set V, the Tt value in non-specific amplification with no miRNA became significantly slow (average: 38.5 minutes to 66.3 minutes). Consequently, it is suggested that, according to the short-chain nucleic acid detection primer set V, it is possible to achieve much higher specific detection.

Example 4

An example will be provided below, in which using primer sets which do not have a dummy sequence, miRNA was elongated, LAMP was performed, and the presence of quantification and the specificity were compared.

TABLE 5

| Type of oligo/ type of primer | | Sequence (5' to 3') | SEQ ID NO: |
|---|---|---|---|
| Short-chain nucleic acid detection primer set V | miR-1307-3p | ACUCGGCGUGGCGUCGGUCGUG | 17 |
| | FIP primer | TGGAATACGTGAGACTGGGCCTAGGGTTGGAGGTTCATGTCA | 18 |
| | BIP primer | CTGACCACCAGTCGCACTGAGCCAGTCCGCCACTGTACT | 19 |
| | LB primer | CGTGGCGTCGGTCGTG | 24 |
| | First elongation primer | CCAGTCCGCCACTGTACTCTAGGCCCTATCTGACAGTGTTCACGACCG | 21 |
| | Second elongation primer | AGGGTTGGAGGTTCATGTCAAGGCCCAGTCTCACGTATTCCACTGACCACC AGTCGCACTGAGGGGACTCGGCGTGGCGT | 22 |
| | Elongated product (positive control) | AGGGTTGGAGGTTCATGTCAAGGCCCAGTCTCACGTATTCCACTGACCACC AGTCGCACTGAGGGGACTCGGCGTGGCGTCGGTCGTGAACACTGTCAGATA GGGCCTAGAGTACAGTGGCGGACTGG | 23 |

Elongation Reaction and Amplification Reaction

Synthetic RNA miR-1307-3p having a copy number of $10^6$, $10^5$, $10^4$, $10^3$ or 0 was elongated and amplified similarly to Example 1 using the short-chain nucleic acid detection primer sets IV and V. As a positive control, an artificially synthesized elongated product (SEQ ID NO: 23) was used.

The results were shown in FIG. 21. It is suggested that, in both the short-chain nucleic acid detection primer sets IV and V, there was a correlation between the copy number of Production of Short-Chain Nucleic Acid Detection Primer Sets VI (Example) and VII (Example)

Short chain nucleic acid detection primer sets VI and VII for elongating and amplifying miRNA (miR-423-5p) (Table 6, SEQ ID NO: 25) were prepared.

The structure of each primer of the short chain nucleic acid detection primer set VI is the same as that shown in FIG. 20, but the base sequence has that shown in Table 6.

That is, the FIP primer contains SEQ ID NO: 26, the BIP primer contains SEQ ID NO: 27, the loop primer (LB sequence) contains SEQ ID NO: 28, the first elongation primer contains SEQ ID NO: 29, the second primer contains SEQ ID NO: 30 and the elongated product of the positive control contains a base sequence of SEQ ID NO: 31.

Figure 22:
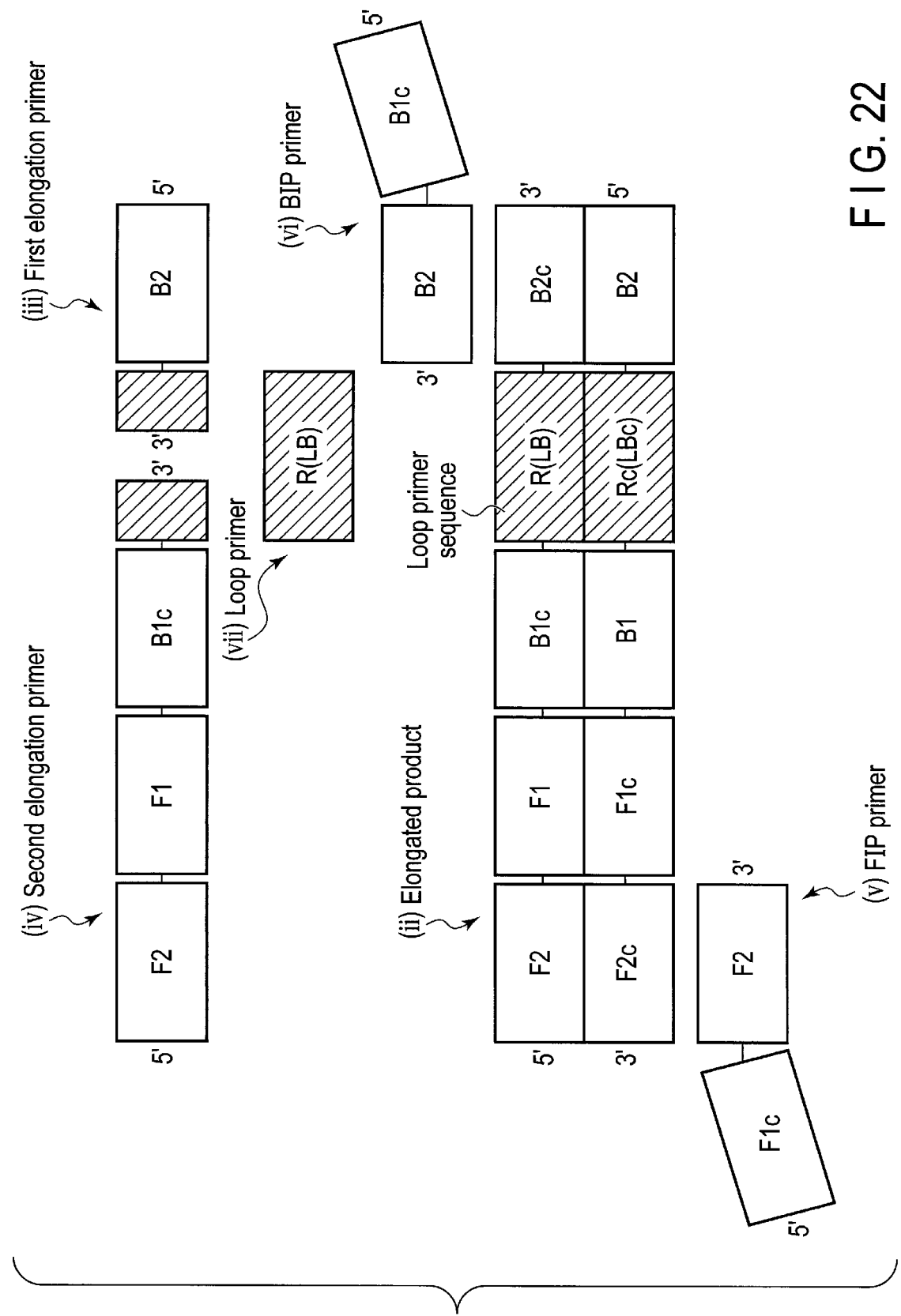
FIG. 22 is a pattern diagram of a short-chain nucleic acid detection primer set VI used in Example 4.

The short chain nucleic acid detection primer set VII has the structure shown in FIG. 22 and contains a base sequence shown in Table 6. That is, the first elongation primer contains a first elongation primer sequence, a B2 sequence and contains a base sequence of SEQ ID NO: 32. The second elongation primer contains a second elongation primer sequence, a B1c sequence, an F1 sequence and an F2 sequence and contains a base sequence of SEQ ID NO: 30. As to the elongated product used as a positive control, one chain contains an F2 sequence, an F1 sequence, a B1c sequence, an R sequence (LB sequence) and a B2c sequence and contains a base sequence of SEQ ID NO: 33.

The FIP primer, BIP primer and loop primer are the same as those contained in the short chain nucleic acid detection primer set VI.

after 95° C. for 2 minutes. Thereafter, the elongation reaction was carried out at 72° C. for 5 minutes.

1 µL of each of the obtained reaction mixtures was added to a solution containing the FIP primer (SEQ ID NO: 26) (final concentration: 1.6 µM), 1.6 µM of the BIP primer (SEQ ID NO: 27), 0.8 µM of the LB primer (SEQ ID NO: 28), 8 U/25 µL of Tin exo-DNA polymerase, Tris-HCl (pH 8.0), 50 mM of KCl, 8 mM of MgSO4, 10 mM of $(NH_4)_2SO_4$ and 0.1% of Tween™-20, 1.4 mM of dNTPs and 24 µL of betaine mixed-solution (0.8 M), and the mixture was subjected to the LAMP under the conditions of 65° C. for 90 minutes. The amplification was carried out using the endpoint turbidity measuring system (LT-16, manufactured by NIPPON GENE, CO., LTD.) and the Tt value was measured. As positive controls, artificially synthesized elongated products (SEQ ID NOS: 31 and 33) were used.

The results are shown in FIG. 23. In both short chain nucleic acid detection primer sets VI and VII, a correlation

TABLE 6

| Type of oligo/ type of primer | | Sequence (5' to 3') | SEQ ID NO: |
|---|---|---|---|
| | miR-423-5p | UGAGGGGCAGAGAGCGAGACUUU | 25 |
| Short-chain nucleic acid detection primer set VI | FIP primer | CCGCGTGTCGTACAACTGCTACGAACACTCCGGATGGT | 26 |
| | BIP primer | AGGTAACGGTTCGACCTCGAGGGGAGGTCCCTCTTTTAAGCG | 27 |
| | LB primer | GGGGCAGAGAGCGAGACTTT | 28 |
| | First elongation primer | GGAGGTCCCTCTTTTAAGCGCTGTTGGATCCGCCGCAAAGTCTCG | 29 |
| | Second elongation primer | ACGAACACTCCGGATGGTAGCAGTTGTACGACACGCGGAGGTAAC GGTTCGACCTCGAGGGGGTGAGGGGCAGAGAG | 30 |
| | Elongated product (positive control) | ACGAACACTCCGGATGGTAGCAGTTGTACGACACGCGGAGGTAAC GGTTCGACCTCGAGGGGGTGAGGGGCAGAGAGCGAGACTTTGCGG CGGATCCAACAGCGCTTAAAAGAGGGACCTCC | 31 |
| Short-chain nucleic acid detection primer set VII | FIP primer | CCGCGTGTCGTACAACTGCTACGAACACTCCGGATGGT | 26 |
| | BIP primer | AGGTAACGGTTCGACCTCGAGGGGAGGTCCCTCTTTTAAGCG | 27 |
| | LB primer | GGGGCAGAGAGCGAGACTTT | 28 |
| | First elongation primer | GGAGGTCCCTCTTTTAAGCGAAAGTCTCG | 32 |
| | Second elongation primer | ACGAACACTCCGGATGGTAGCAGTTGTACGACACGCGGAGGTAAC GGTTCGACCTCGAGGGGGTGAGGGGCAGAGAG | 30 |
| | Elongated product (positive control) | ACGAACACTCCGGATGGTAGCAGTTGTACGACACGCGGAGGTAAC GGTTCGACCTCGAGGGGGTGAGGGGCAGAGAGCGAGACTTTCGCTT AAAAGAGGGACCTCC | 33 |

Elongation Reaction

Using the short chain nucleic acid detection primer sets VI and VII, a copy number of $10^6$, $10^5$, $10^4$, $10^3$ or 0 of synthetic RNA miR-423-5p were elongated and amplified. Then, using a reaction mixture (reaction volume: 20 µL) containing the first elongation primer (SEQ ID NOS: 29 and 32) (final concentration: 10 nM), 67 U/20 µL of reverse transcriptase (MultiScribe™ Reverse Transcriptase), RT buffer (1×) in Hight-Capacity cDNA Reverse Transcription Kit, dNTPs (final concentration: 0.1 mM) and 4 U/20 µL of RNase OUT™, the reverse transcription reactions were carried out under the following conditions: 16° C. for 10 minutes, 42° C. for 5 minutes and 85° C. for 5 minutes.

Amplification Reaction

After the completion of each reaction, the second amplification primer (SEQ ID NO: 30) (final concentration: 10 nM) and 0.4 U of DeepVent™(exo-) DNA Polymerase (a total of 5 µL) were added to the reaction mixture, and the mixture was subjected to the elongation reaction at 20 cycles of 95° C. for 20 sec, 55° C. for 30 sec, and 72° C. for 30 sec was found between the copy number of miRNA and the Tt value. In the short chain nucleic acid detection primer set VII, non-specific amplification which does not contain miRNA was observed in one of two series, which was acceptable since it was sufficiently later than that of the specific amplification. Thus, it was suggested that even with use of the primer set VII which does not contain a dummy sequence, miRNA can be quantified with high sensitivity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A primer set comprising:
a short-chain nucleic acid elongation primer set and an amplification primer set,
wherein
the short-chain nucleic acid elongation primer set is configured to yield an elongated product from a target short-chain RNA containing a first sequence,
the elongated product is a mutually complementary double-stranded nucleic acid, one chain contains a second sequence, a third sequence, a fourth sequence, a complementary sequence of cDNA of the first sequence (hereinafter, "cDNA of the first sequence" referred to as "1'-th sequence"), and a sixth sequence in this order in a 3' to 5' direction,
the short-chain nucleic acid elongation primer set comprises:
a first elongation primer comprising a first elongation primer sequence which hybridizes with the first sequence and a complementary sequence of the sixth sequence in this order in the 3' to 5' direction; and
a second elongation primer comprising a second elongation primer sequence which hybridizes with the 1'-th sequence, the fourth sequence, the third sequence, and the second sequence in this order in the 3' to 5' direction, and
the amplification primer set is configured to amplify the elongated product by LAMP method which comprises:
the FIP primer comprising the second sequence and a complementary sequence of the third sequence in this order in the 3' to 5' direction,
the BIP primer comprising the complementary sequence of the sixth sequence and the fourth sequence in this order in the 3' to 5' direction, and
the loop primer comprising the complementary sequence of the 1'-th sequence.

2. The primer set of claim 1, wherein:
the second sequence is an F2 sequence,
the third sequence is an F1 sequence,
the fourth sequence is a B1c sequence,
the sixth sequence is a B2c sequence,
the first elongation primer comprises the first elongation primer sequence and a B2 sequence in this order in the 3' to 5' direction,
the second elongation primer comprises the second elongation primer sequence, the B1c sequence, the F1 sequence, and the F2 sequence in this order in the 3' to 5' direction,
the FIP primer comprises the F2 sequence and an F1c sequence in this order in the 3' to 5' direction,
the BIP primer comprises the B2 sequence and the B1c sequence in this order in the 3' to 5' direction,
the loop primer comprising the complementary sequence of the 1'-th sequence, and
the F1 sequence is complementary to the F1c sequence, the B2 sequence is complementary to the B2c sequence.

3. A primer set comprising:
a short-chain nucleic acid elongation primer set and an amplification primer set,
wherein
the short-chain nucleic acid elongation primer set is configured to yield an elongated product from a target short-chain RNA containing a first sequence,
the elongated product is a mutually complementary double-stranded nucleic acid, one chain contains a second sequence, a third sequence, a fourth sequence, a complementary sequence of cDNA of the first sequence (hereinafter, "cDNA of the first sequence" referred to as "1'-th sequence"), fifth sequence and a sixth sequence in this order in a 3' to 5' direction,
the short-chain nucleic acid elongation primer set comprises:
a first elongation primer comprising a first elongation primer sequence which hybridizes with the first sequence, a complementary sequence of the fifth sequence and a complementary sequence of the sixth sequence in this order in the 3' to 5' direction; and
a second elongation primer comprising a second elongation primer sequence which hybridizes with the 1'-th sequence, the fourth sequence, the third sequence, and the second sequence in this order in the 3' to 5' direction, and the amplification primer set is configured to amplify the elongated product by LAMP method which comprises;

the FIP primer comprising the second sequence and a complementary sequence of the third sequence in this order in the 3' to 5' direction, the BIP primer comprising the complementary sequence of the sixth sequence and the fourth sequence in this order in the 3' to 5' direction, and the loop primer comprising the fifth sequence.

4. The primer set of claim 3, wherein:
the second sequence is an F2 sequence,
the third sequence is an F1 sequence,
the fourth sequence is a B1c sequence,
the fifth sequence is an LB sequence,
the sixth sequence is a B2c sequence,
the first elongation primer comprises the first elongation primer sequence, an LBc sequence, and a B2 sequence in this order in the 3' to 5' direction,
the second elongation primer comprises the second elongation primer sequence, the B1c sequence, the F1 sequence, and the F2 sequence in this order in the 3' to 5' direction,
the FIP primer containing the F2 sequence and an F1c sequence in this order in the 3' to 5' direction,
the BIP primer containing the B2 sequence and the B1c sequence in this order in the 3' to 5' direction,
the loop primer containing the LB sequence, and
the LB sequence is complementary to the LBc sequence, the F1 sequence is complementary to the F1c sequence, the B2 sequence is complementary to the B2c sequence.

5. A primer set comprising:
a short-chain nucleic acid elongation primer set and
an amplification primer set,
wherein
the short-chain nucleic acid elongation primer set is configured to yield an elongated product from a target short-chain RNA containing a first sequence,
the elongated product is a mutually complementary double-stranded nucleic acid, one chain contains a second sequence, a third sequence, a fourth sequence, a complementary sequence of cDNA of the first sequence (hereinafter, "cDNA of the first sequence" referred to as "1'-th sequence"), fifth sequence and a sixth sequence in this order in a 3' to 5' direction,
the short-chain nucleic acid elongation primer set comprises:
a first elongation primer comprising a first elongation primer sequence which hybridizes with the first sequence, a complementary sequence of the fifth sequence and a complementary sequence of the sixth sequence in this order in the 3' to 5' direction; and
a second elongation primer comprising a second elongation primer sequence which hybridizes with the 1'-th sequence, the fourth sequence, the third sequence, and the second sequence in this order in the 3' to 5' direction, and
the amplification primer set is configured to amplify the elongated product by LAMP method which comprises;
the FIP primer comprising the second sequence and a complementary sequence of the forth sequence in this order in the 3' to 5' direction, the BIP primer comprising the complementary sequence of the sixth sequence and the fifth sequence in this order in the 3' to 5' direction, and the loop primer comprising the complementary sequence of the third sequence.

6. The primer set of claim 5, wherein:
the second sequence is an F2 sequence,
the third sequence is an LFc sequence,
the fourth sequence is an F1 sequence,
the fifth sequence is a B1c sequence,
the sixth sequence is a B2c sequence,
the first elongation primer comprises the first elongation primer sequence, a B1 sequence, and a B2 sequence in this order in the 3' to 5' direction,
the second elongation primer comprises the second elongation primer sequence, the F1 sequence, the LFc sequence, and the F2 sequence in this order in the 3' to 5' direction,
the FIP primer containing the F2 sequence and an F1c sequence in this order in the 3' to 5' direction,
the BIP primer containing the B2 sequence and the B1c sequence in this order in the 3' to 5' direction,
the loop primer containing an LF sequence, and
the F1 sequence is complementary to the F1c sequence, the B1 sequence is complementary to the B1c sequence, the B2 sequence is complementary to the B2c sequence, the LF sequence is complementary to the LFc sequence.

7. An assay kit, comprising:
the primer set of claim 1,
a nucleic acid elongation reagent, and
a LAMP reagent.

8. The assay kit of claim 7, wherein the short-chain nucleic acid elongation primer set and the amplification primer set in the short-chain nucleic acid detection primer set are accommodated in seperate containers.

9. The assay kit of claim 7, further comprising:
a marker substance generating an electrical signal which changes with an increase in the amplification product; and
an electrochemical detection device for detecting the electrical signal.

10. A short-chain nucleic acid detection method for detecting a target short-chain nucleic acid containing a first sequence in a sample using the primer set of claim 1, the method comprising:
hybridizing the first elongation primer with the first sequence and elongating the first sequence to obtain an elongated intermediate product containing the 1'-th sequence;
dissociating the elongated intermediate product from the target short-chain nucleic acid;
hybridizing the secon elongation primer with the 1'-th sequence of the elongated intermediate product and elongating the second elongation primer and the elongated intermediate product to obtain the elongated product;
maintaining an amplification reaction solution containing the elongated product, the amplification primer set, and a strand displacement DNA polymerasse under isothermal amplification reaction conditions, thereby amplifying the 1'-th sequence and/or the complementary sequence thereof using the elongated product as a template to obtain an amplification product; and
detecting the amplification product during maintaining under the isothermal amplification reaction conditions.

11. The method of claim 10, wherein the amplification reaction solution comprises the marker substance generating an electrochemical signal which changes with an increase in the amplification product, and the detecting is performed by detecting the electrochemical signal.

12. The method of claim 10, wherein
the second sequence is an F2 sequence,
the third sequence is an F1 sequence,
the fourth sequence is a B1c sequence,
the sixth sequence is a B2 c sequence,
the first elongation primer comprises the first elongation primer sequence and a B2 sequence in this order in the 3' to 5' direction,
the second elongation primer comprises the second elongation primer sequence, the B1c sequence, the F1 sequence, and the F2 sequence in this order in the 3' to 5' direction,
the FIP primer comprises the F2 sequence and the B1c sequence in this order in the 3' 5' direction,
the BIP primer comprises the B2 sequence and and the B1c sequence in this order in the 3' 5' direction,
the loop primer comprising the complementary sequence of the 1'-th sequence, and the F1 sequence is complementary to the F1c sequence, the B2 sequence is complementary to the B2c sequence, and
the method further comprising amplifying the elongated product to obtain a amplification product with a LAMP primer set comprising the FIP primer containing an F2 sequence and an F1c in this order in the 3' to 5' direction, the BIP primer comprising a B2 sequence and a B1c sequence in this order in the 3' to 5' direction, and
the loop primer comprising g the complementary sequence of the 1'-th sequence, and
the F1c sequence is complementary to the F1 sequence and the B1c sequence is complementary to the B1 sequence.

13. A primer set comprising:
a short-chain nucleic acid elongation primer set and
an amplification primer set,
wherein
the short-chain nucleic acid elongation primer set is configured to yield an elongated product from a target short-chain RNA containing a first sequence,
the elongated product is a mutually complementary double-standard nucleic acid, one chain contains a second sequence, a third sequence, a fourth sequence, a complementary sequence of cDNA of the first sequence (hereinafter, "cDNA of the first sequence" referred to a "1-th sequence"), and a sixth sequence in this order in a 3' to 5' direction,
the short-chain nucleic acid elongation primer set comprises:
a first elongation primer comprising a first elongation primer sequence which hybridizes with the first sequence and a complementary sequence of the sixth sequence in this order in the 3' to 5' direction; and
a second elongation primer comprising a second elongation primer sequence which hybridizes with the 1'-th sequence, the fourth sequence, the third sequence, and the second in this order in the 3' to 5' direction, and
the amplification primer set is configured to amplify the elongated product by LAMP method which comprises;
the FIP primer comprising the second sequence and a complementary sequence of the third sequence in this order 3' to 5' direction, and the BIP primer comprising the complementary sequence of the sixth sequence and the complementary sequence of the 1'-th in this order in the 3' to 5' direction, and
the loop primer comprising the complementary sequence of the third sequence.

14. The primer set of claim 13, wherein:
the second sequence is an F2 sequence,
third sequence is an LFc sequence,
the fourth sequence is an F1 sequence,
the sixth sequence is a B2c sequence,
the first elongation primer comprises the first elongation primer sequence and a B2 sequence in this order in the 3' to 5' direction,
the second elongation primer comprises the second elongation primer sequence, the F1 sequence, the LFc sequence, and the F2 sequence in this order in the 3' to 5' direction, p1 the FIP primer comprises the F2 sequence and an F1c sequence in this order in the 3' to 5' direction,
the BIP primer comprises the B2 sequence and a complementary sequence of the 1'-th sequence in this order in the 3' to 5' direction,
the loop primer comprising an LF sequence, and
the LFc sequence is complementary to the LF sequence, the F1c sequence is complementary to the F1 sequence and the B2c sequence is complementary to the B2 sequence.

15. A primer set comprising:
a short-chain nucleic acid elongation primer set and
an amplification primer set,
wherein
the short-chain nucleic acid elongation primer set is configured to yield an elongated product from a target short-chain RNA containing a first sequence,
the elongated product is mutually complementary double-stranded nucleic acid, one chain contains a second sequence, a third sequence, a complementary sequence of cDNA of the first sequence (hereinafter, "cDNA of the first sequence" referred to a "1'-th sequence"), a fifth sequence, , and a sixth sequence in this order in the 3' to 5' direction,
the short-chain nucleic elongation primer set comprises:
a first elongation primer comprising a first elongation primer sequence which hybridizes with the first sequence, a complementary sequence of the fifth sequence and a complementary sequence of the sixth sequence in this order in the 3' to 5' direction; and
a second elongation primer comprising a second elongation primer sequence which hybridizes with the 1- th sequence, the third sequence, and the second sequence in this order in the 3' to 5' direction, and
the amplification primer set is configured to amplify the elongated product by LAMP method which comprises;
the FIP primer comprising the second sequence and a complementary sequence of the third sequence in this order in the 3' to 5' direction,
the BIP primer comprising the complementary sequence of the sixth sequence and thee complementary sequence of the 1'-th sequence in this order in the 3' to 5' direction, and
the loop primer comprising the complementary sequence of the fifth sequence.

16. The primer set of claim 15, wherein:
the second sequence is an F2 sequence,
the third sequence is an F1 sequence,
the fifth sequence is a LB sequence,
the sixth sequence is a B2c sequence, the first elongation primer comprises the first elongation primer sequence, a LBc sequence and a B2 sequence in this order in the 3' to 5' direction, the second elongation primer comprises the second elongation primer sequence, the F1 sequence and the F2 in this order in the 3' to 5' direction, the FIP primer comprises the F2 sequence and an F1c sequence in this order in the 3' to 5' direction, the BIP primer comprises the B2 sequence and a complementary sequence of the 1'-th sequence in this order in the 3' to 5' direction, the loop primer comprising the LB sequence, and LBc sequence is complementary to the LB sequence, the B2c sequence is complementary to the B2 sequence and the F1c sequence is complementary to the F1 sequence.

17. A primer set comprising:

a short-chain nucleic acid elongation primer set and an amplification primer set, wherein the short-chain nucleic acid elongation primer set is configured to yield an elongated product from a target short-chain RNA containing a first sequence, the elongated product is a mutually complementary double-standard nucleic acid, one chain contains a second sequence, a third sequence, a complementary sequence of cDNA of the first sequence (hereinafter, "cDNA of the first sequence" referred to as "1'-th sequence"), a fifth sequence, and a sixth sequence in this order in the 3' to 5' direction, the short-chain nucleic acid elongation primer set comprises:

a first elongation primer comprising a first elongation primer sequence which hybridizes with the first sequence, a complementary sequence of the fifth sequence and a complementary sequence of the sixth sequence in this order in the 3' to 5' direction; and a second elongation primer comprising a second elongation primer sequence which hybridizes with the 1'-th sequence, the third sequence, and the second sequence in this order in the 3' to 5' direction; and the amplification primer set if configured to amplify the elongated product by LAMP method which comprises;

the FIP primer comprising the second sequence and the 1'-th sequence in this order in the 3' to 5' direction, the BIP primer comprising the complementary sequence of the sixth sequence and the forth sequence in this order in the 3' to 5' direction, and the loop primer comprising the complementary sequence of the third sequence.

18. The primer set of claim 17, wherein:

the second sequence is an F2 sequence, the third sequence is an LFc sequence, the fifth sequence is a B1c sequence, the sixth sequence is a B2c sequence, the first elongation primer comprises the first elongation primer sequence, a B1 sequence and a B2 sequence in this order in the 3' to 5' direction, the second elongation primer comprises the second elongation primer sequence, the LFc sequence and the F2 sequence in this order in the 3' to 5' direction, the FIP primer comprises the F2 sequence and the 1'-th sequence in this order in the 3' to 5' direction, the BIP primer comprises the B2 sequence and the B1c sequence in this order in the 3' to 5' direction, the loop primer comprising an LF sequence, and LFc sequence is complementary to the LF sequence, the B1c sequence is complementary to the B1 sequence, and the B2c sequence is complementary to the B2 sequence.

* * * * *

UNITED STATES PATENT AND TRADEMARK OFFICE
CERTIFICATE OF CORRECTION

PATENT NO. : 10,975,433 B2
APPLICATION NO. : 16/017367
DATED : April 13, 2021
INVENTOR(S) : Keiko Ito et al.

Page 1 of 2

It is certified that error appears in the above-identified patent and that said Letters Patent is hereby corrected as shown below:

In the Drawings

Delete FIG. 13A:

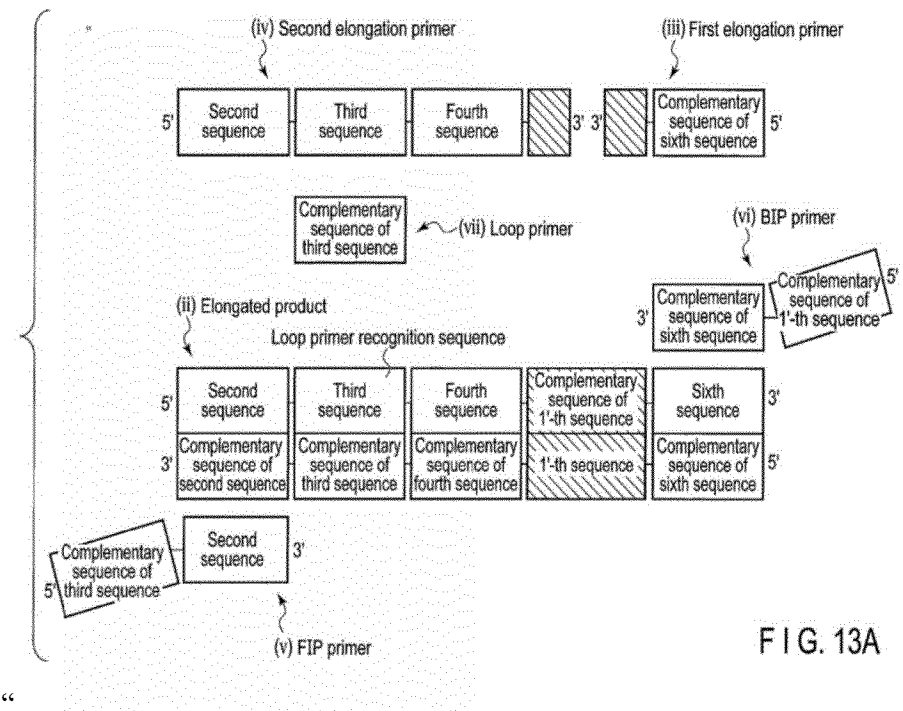

"                                                                    "

Signed and Sealed this
Twenty-sixth Day of April, 2022

Katherine Kelly Vidal
*Director of the United States Patent and Trademark Office*

CERTIFICATE OF CORRECTION (continued)
U.S. Pat. No. 10,975,433 B2

And insert:

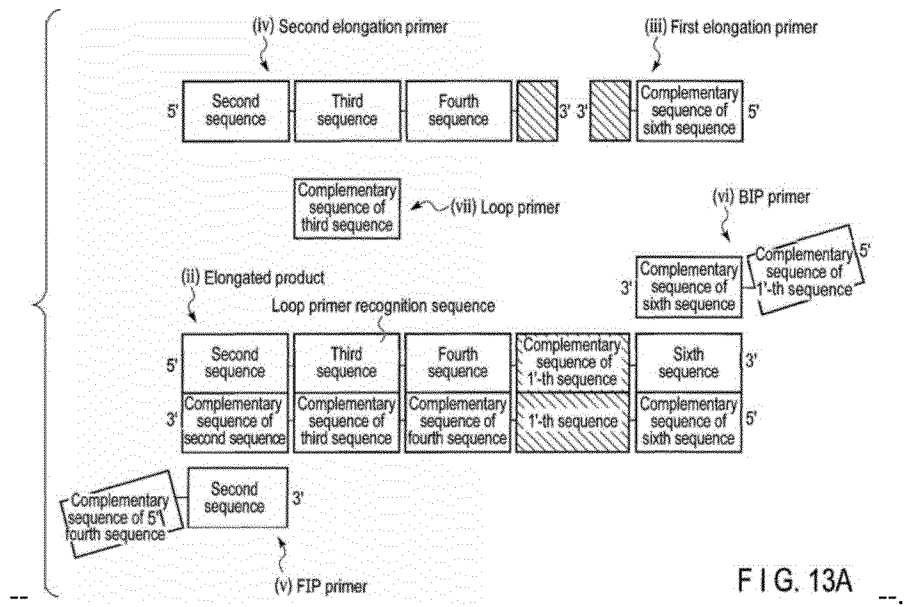

In the Claims

Column 51, Claim 13, Line 66, "third" should read -- fourth --.

Column 52, Claim 15, Line 61, delete "the complementary sequence".

SEQUENCE LISTING

<160> NUMBER OF SEQ ID NOS: 33

<210> SEQ ID NO 1
<211> LENGTH: 22
<212> TYPE: RNA
<213> ORGANISM: Homo sapiens

<400> SEQUENCE: 1
ugagguagua gguuguauag uu                                            22

<210> SEQ ID NO 2
<211> LENGTH: 40
<212> TYPE: DNA
<213> ORGANISM: Artificial Sequence
<220> FEATURE:
<223> OTHER INFORMATION: FIP primer

<400> SEQUENCE: 2
ggcctactgt ttatgctcgg ctccggacga ctggatcctt                         40

<210> SEQ ID NO 3
<211> LENGTH: 40
<212> TYPE: DNA
<213> ORGANISM: Artificial Sequence
<220> FEATURE:
<223> OTHER INFORMATION: BIP primer

<400> SEQUENCE: 3 gatggggaa gcatctcggg acttgctgac ctgaatggtg                          40

<210> SEQ ID NO 4
<211> LENGTH: 21
<212> TYPE: DNA
<213> ORGANISM: Artificial Sequence
<220> FEATURE:
<223> OTHER INFORMATION: LB primer

<400> SEQUENCE: 4
ggcttgcagt taattgcgta c                                             21

<210> SEQ ID NO 5
<211> LENGTH: 48
<212> TYPE: DNA
<213> ORGANISM: Artificial Sequence
<220> FEATURE:
<223> OTHER INFORMATION: first elongation primer

<400> SEQUENCE: 5
acttgctgac ctgaatggtg tacgcaatta actgcaagcc aactatac                48

<210> SEQ ID NO 6
<211> LENGTH: 79
<212> TYPE: DNA
<213> ORGANISM: Artificial Sequence
<220> FEATURE:
<223> OTHER INFORMATION: second elongation primer

<400> SEQUENCE: 6
ccggacgact ggatccttag ccgagcataa acagtaggcc gatggggaa gcatctcggg    60 gggtgaggta gtaggttgt                                                79

<210> SEQ ID NO 7
<211> LENGTH: 125
<212> TYPE: DNA
<213> ORGANISM: Artificial Sequence

```
<220> FEATURE:
<223> OTHER INFORMATION: elongation product

<400> SEQUENCE: 7
ccggacgact ggatccttag ccgagcataa acagtaggcc gatgggggaa gcatctcggg    60
gggtgaggta gtaggttgta tagttggctt gcagttaatt gcgtacacca ttcaggtcag   120
caagt                                                               125

<210> SEQ ID NO 8
<211> LENGTH: 40
<212> TYPE: DNA
<213> ORGANISM: Artificial Sequence
<220> FEATURE:
<223> OTHER INFORMATION: FIP primer

<400> SEQUENCE: 8
cgtccagcat atcaaaaccg cgccttcgga gaacccctct                          40

<210> SEQ ID NO 9
<211> LENGTH: 41
<212> TYPE: DNA
<213> ORGANISM: Artificial Sequence
<220> FEATURE:
<223> OTHER INFORMATION: BIP primer

<400> SEQUENCE: 9
cgattcacga tgcatccggc agacgttctg gtacgaactc g                        41

<210> SEQ ID NO 10
<211> LENGTH: 20
<212> TYPE: DNA
<213> ORGANISM: Artificial Sequence
<220> FEATURE:
<223> OTHER INFORMATION: LB primer

<400> SEQUENCE: 10
caacagcagc cggggagttg                                                20

<210> SEQ ID NO 11
<211> LENGTH: 48
<212> TYPE: DNA
<213> ORGANISM: Artificial Sequence
<220> FEATURE:
<223> OTHER INFORMATION: first elongation primer

<400> SEQUENCE: 11
gacgttctgg tacgaactcg caactccccg gctgctgttg aactatac                 48

<210> SEQ ID NO 12
<211> LENGTH: 80
<212> TYPE: DNA
<213> ORGANISM: Artificial Sequence
<220> FEATURE:
<223> OTHER INFORMATION: second elongation primer

<400> SEQUENCE: 12
ccttcggaga accccctctcg cggttttgat atgctggacg cgattcacga tgcatccggc   60
agggtgaggt agtaggttgt                                                80

<210> SEQ ID NO 13
<211> LENGTH: 126
<212> TYPE: DNA
<213> ORGANISM: Artificial Sequence
<220> FEATURE:
```

<223> OTHER INFORMATION: elongation product

<400> SEQUENCE: 13
ccttcggaga accccctctcg cggttttgat atgctggacg cgattcacga tgcatccggc    60
agggtgaggt agtaggttgt atagttcaac agcagccggg gagttgcgag ttcgtaccag   120
aacgtc                                                              126

<210> SEQ ID NO 14
<211> LENGTH: 28
<212> TYPE: DNA
<213> ORGANISM: Artificial Sequence
<220> FEATURE:
<223> OTHER INFORMATION: first elongation primer

<400> SEQUENCE: 14
gacgttctgg tacgaactcg aactatac                                       28

<210> SEQ ID NO 15
<211> LENGTH: 100
<212> TYPE: DNA
<213> ORGANISM: Artificial Sequence
<220> FEATURE:
<223> OTHER INFORMATION: second elongation primer

<400> SEQUENCE: 15
ccttcggaga accccctctcg cggttttgat atgctggacg cgattcacga tgcatccggc    60
acaacagcag ccggggagtt ggggtgaggt agtaggttgt                          100

<210> SEQ ID NO 16
<211> LENGTH: 126
<212> TYPE: DNA
<213> ORGANISM: Artificial Sequence
<220> FEATURE:
<223> OTHER INFORMATION: elongation product

<400> SEQUENCE: 16
ccttcggaga accccctctcg cggttttgat atgctggacg cgattcacga tgcatccggc    60
acaacagcag ccggggagtt ggggtgaggt agtaggttgt atagttcgag ttcgtaccag   120
aacgtc                                                              126

<210> SEQ ID NO 17
<211> LENGTH: 22
<212> TYPE: RNA
<213> ORGANISM: Homo sapiens

<400> SEQUENCE: 17
acucggcgug gcgucggucg ug                                             22

<210> SEQ ID NO 18
<211> LENGTH: 42
<212> TYPE: DNA
<213> ORGANISM: Artificial Sequence
<220> FEATURE:
<223> OTHER INFORMATION: FIP primer

<400> SEQUENCE: 18
tggaatacgt gagactgggc ctagggttgg aggttcatgt ca                       42

<210> SEQ ID NO 19
<211> LENGTH: 39
<212> TYPE: DNA
<213> ORGANISM: Artificial Sequence

```
<220> FEATURE:
<223> OTHER INFORMATION: BIP primer

<400> SEQUENCE: 19
ctgaccacca gtcgcactga gccagtccgc cactgtact                                39

<210> SEQ ID NO 20
<211> LENGTH: 22
<212> TYPE: DNA
<213> ORGANISM: Artificial Sequence
<220> FEATURE:
<223> OTHER INFORMATION: LB primer

<400> SEQUENCE: 20
aacactgtca gatagggcct ag                                                  22

<210> SEQ ID NO 21
<211> LENGTH: 48
<212> TYPE: DNA
<213> ORGANISM: Artificial Sequence
<220> FEATURE:
<223> OTHER INFORMATION: first elongation primer

<400> SEQUENCE: 21
ccagtccgcc actgtactct aggccctatc tgacagtgtt cacgaccg                      48

<210> SEQ ID NO 22
<211> LENGTH: 80
<212> TYPE: DNA
<213> ORGANISM: Artificial Sequence
<220> FEATURE:
<223> OTHER INFORMATION: second elongation primer

<400> SEQUENCE: 22
agggttggag gttcatgtca aggcccagtc tcacgtattc cactgaccac cagtcgcact         60
gaggggactc ggcgtggcgt                                                     80

<210> SEQ ID NO 23
<211> LENGTH: 128
<212> TYPE: DNA
<213> ORGANISM: Artificial Sequence
<220> FEATURE:
<223> OTHER INFORMATION: elongation product

<400> SEQUENCE: 23
agggttggag gttcatgtca aggcccagtc tcacgtattc cactgaccac cagtcgcact         60
gaggggactc ggcgtggcgt cggtcgtgaa cactgtcaga tagggcctag agtacagtgg        120
cggactgg                                                                 128

<210> SEQ ID NO 24
<211> LENGTH: 16
<212> TYPE: DNA
<213> ORGANISM: Artificial Sequence
<220> FEATURE:
<223> OTHER INFORMATION: LB primer

<400> SEQUENCE: 24
cgtggcgtcg gtcgtg                                                         16

<210> SEQ ID NO 25
<211> LENGTH: 23
<212> TYPE: RNA
<213> ORGANISM: Homo sapiens
```

```
<400> SEQUENCE: 25
ugaggggcag agagcgagac uuu                                             23

<210> SEQ ID NO 26
<211> LENGTH: 38
<212> TYPE: DNA
<213> ORGANISM: Artificial Sequence
<220> FEATURE:
<223> OTHER INFORMATION: FIP primer

<400> SEQUENCE: 26
ccgcgtgtcg tacaactgct acgaacactc cggatggt                             38

<210> SEQ ID NO 27
<211> LENGTH: 42
<212> TYPE: DNA
<213> ORGANISM: Artificial Sequence
<220> FEATURE:
<223> OTHER INFORMATION: BIP primer

<400> SEQUENCE: 27
aggtaacggt tcgacctcga ggggaggtcc ctcttttaag cg                        42

<210> SEQ ID NO 28
<211> LENGTH: 20
<212> TYPE: DNA
<213> ORGANISM: Artificial Sequence
<220> FEATURE:
<223> OTHER INFORMATION: LB primer

<400> SEQUENCE: 28
ggggcagaga gcgagacttt                                                 20

<210> SEQ ID NO 29
<211> LENGTH: 45
<212> TYPE: DNA
<213> ORGANISM: Artificial Sequence
<220> FEATURE:
<223> OTHER INFORMATION: first elongation primer

<400> SEQUENCE: 29
ggaggtccct cttttaagcg ctgttggatc cgccgcaaag tctcg                     45

<210> SEQ ID NO 30
<211> LENGTH: 77
<212> TYPE: DNA
<213> ORGANISM: Artificial Sequence
<220> FEATURE:
<223> OTHER INFORMATION: second elongation primer

<400> SEQUENCE: 30
acgaacactc cggatggtag cagttgtacg acacgcggag gtaacggttc gacctcgagg     60
gggtgagggg cagagag                                                    77

<210> SEQ ID NO 31
<211> LENGTH: 122
<212> TYPE: DNA
<213> ORGANISM: Artificial Sequence
<220> FEATURE:
<223> OTHER INFORMATION: elongation product

<400> SEQUENCE: 31
acgaacactc cggatggtag cagttgtacg acacgcggag gtaacggttc gacctcgagg     60
gggtgagggg cagagagcga gactttgcgg cggatccaac agcgcttaaa agagggacct    120
```

-continued cc                                                                    122

<210> SEQ ID NO 32
<211> LENGTH: 29
<212> TYPE: DNA
<213> ORGANISM: Artificial Sequence
<220> FEATURE:
<223> OTHER INFORMATION: first elongation primer

<400> SEQUENCE: 32
ggaggtccct cttttaagcg aaagtctcg                                        29

<210> SEQ ID NO 33
<211> LENGTH: 106
<212> TYPE: DNA
<213> ORGANISM: Artificial Sequence
<220> FEATURE:
<223> OTHER INFORMATION: elongation product

<400> SEQUENCE: 33
acgaacactc cggatggtag cagttgtacg acacgcggag gtaacggttc gacctcgagg       60
gggtgagggg cagagagcga gactttcgct taaaagaggg acctcc                     106